(12) United States Patent
Suh et al.

(10) Patent No.: US 11,165,025 B2
(45) Date of Patent: Nov. 2, 2021

(54) COMPOUND AND ORGANIC ELECTRONIC ELEMENT COMPRISING SAME

(71) Applicant: LG Chem, Ltd., Seoul (KR)

(72) Inventors: Sang Duk Suh, Daejeon (KR); Yongbum Cha, Daejeon (KR); Sung Kil Hong, Daejeon (KR); Dongheon Kim, Daejeon (KR)

(73) Assignee: LG Chem, Ltd.

( * ) Notice: Subject to any disclaimer, the term of this patent is extended or adjusted under 35 U.S.C. 154(b) by 369 days.

(21) Appl. No.: 15/775,607

(22) PCT Filed: Nov. 17, 2016

(86) PCT No.: PCT/KR2016/013273
§ 371 (c)(1),
(2) Date: May 11, 2018

(87) PCT Pub. No.: WO2017/086713
PCT Pub. Date: May 26, 2017

(65) Prior Publication Data
US 2018/0331297 A1    Nov. 15, 2018

(30) Foreign Application Priority Data

Nov. 17, 2015 (KR) .................. 10-2015-0161034

(51) Int. Cl.
*H01L 51/00*       (2006.01)
*H01L 51/50*       (2006.01)
(Continued)

(52) U.S. Cl.
CPC .......... *H01L 51/0052* (2013.01); *C07C 25/13* (2013.01); *C07C 25/22* (2013.01);
(Continued)

(58) Field of Classification Search
CPC . H01L 51/0085; H01L 51/5056; H01L 51/50; H01L 51/0052; H01L 51/0072; H01L 51/5088; H01L 51/5278
See application file for complete search history.

(56) References Cited

U.S. PATENT DOCUMENTS

| 3,752,668 A | 8/1973 | Baltazzi et al. |
| 2002/0127428 A1* | 9/2002 | Swanson ............. H01L 51/0061 428/690 |

(Continued)

FOREIGN PATENT DOCUMENTS

| GB | 001222252 A | 2/1971 |
| GB | 001245008 A | 9/1971 |

(Continued)

OTHER PUBLICATIONS

KR 10-2013-0023071 A online machine translaiton as provided by "Patent Translate: Powered by EPO and Google", translated on Jul. 2, 2020.*

(Continued)

*Primary Examiner* — Golam Mowla
(74) *Attorney, Agent, or Firm* — Lerner, David, Littenberg, Krumholz & Mentlik, LLP

(57) ABSTRACT

The present application relates to a compound and an organic electronic device including the same.

14 Claims, 2 Drawing Sheets

| 4 |
| 7 |
| 3 |
| 6 |
| 5 |
| 2 |
| 1 |

(51) Int. Cl.
  *H01L 51/52* (2006.01)
  *C07C 255/52* (2006.01)
  *C09K 11/06* (2006.01)
  *C07C 255/51* (2006.01)
  *C07C 25/22* (2006.01)
  *C07C 25/13* (2006.01)
  *C07C 255/54* (2006.01)
  *C07C 255/61* (2006.01)

(52) U.S. Cl.
  CPC .......... *C07C 255/51* (2013.01); *C07C 255/52* (2013.01); *C07C 255/54* (2013.01); *C07C 255/61* (2013.01); *C09K 11/06* (2013.01); *H01L 51/00* (2013.01); *H01L 51/50* (2013.01); *C07C 2603/18* (2017.05); *C09K 2211/1007* (2013.01); *C09K 2211/1011* (2013.01); *C09K 2211/1029* (2013.01); *C09K 2211/185* (2013.01); *H01L 51/0072* (2013.01); *H01L 51/0085* (2013.01); *H01L 51/5056* (2013.01); *H01L 51/5088* (2013.01); *H01L 51/5278* (2013.01)

(56) References Cited

U.S. PATENT DOCUMENTS

| | | |
|---|---|---|
| 2002/0158242 A1 | 10/2002 | Son et al. |
| 2006/0035109 A1* | 2/2006 | Arakane ................ C09K 11/06 428/690 |
| 2009/0315022 A1* | 12/2009 | Morishita ............ C07D 409/14 257/40 |
| 2010/0044686 A1 | 2/2010 | Morishita |
| 2013/0146850 A1* | 6/2013 | Pieh .................... H01L 51/5203 257/40 |
| 2015/0034923 A1 | 2/2015 | Kim et al. |

FOREIGN PATENT DOCUMENTS

| | | |
|---|---|---|
| JP | H04338762 A | 11/1992 |
| JP | H07056369 A | 3/1995 |
| KR | 100377321 B1 | 3/2003 |
| KR | 20090088902 A | 8/2009 |
| KR | 20130023071 A | 3/2013 |
| KR | 20150015647 A | 2/2015 |

OTHER PUBLICATIONS

Search report from International Application No. PCT/KR2016/013273, dated Feb. 27, 2017.

Perepichka, I. F., et al., "Electron Acceptors of the Fluorene Series. 7.1 2,7-Dicyano-4,5-dinitro-9-X-fluorenes: Synthesis, Cyclic Voltammetry, Charge Transfer Complexation with N-Propylcarbazole in Solution, and X-ray Crystal Structures of Two Tetrathiafulvalene Complexes." Journal of Orgqanic Chemistry, Received Feb. 24, 1998, vol. 53, pp. 6484-6493.

* cited by examiner

[Figure 1]
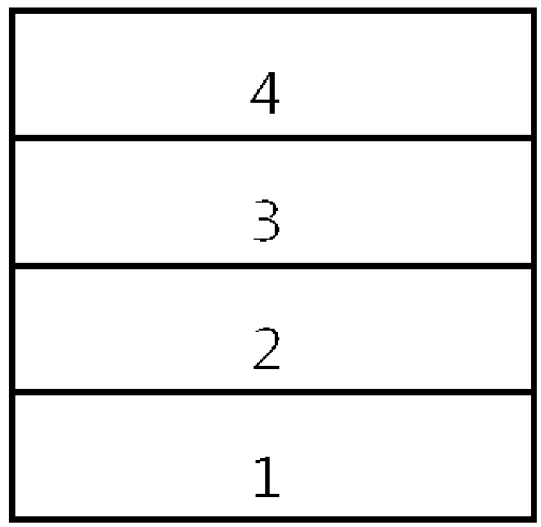
[Figure 2]
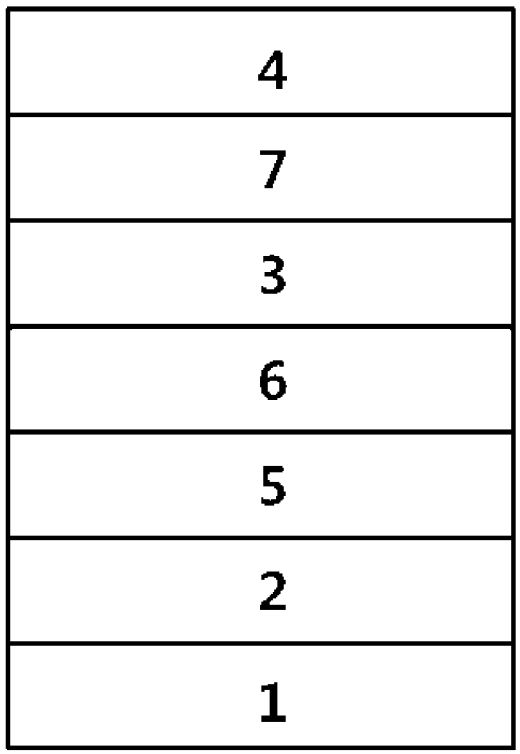

[Figure 3]
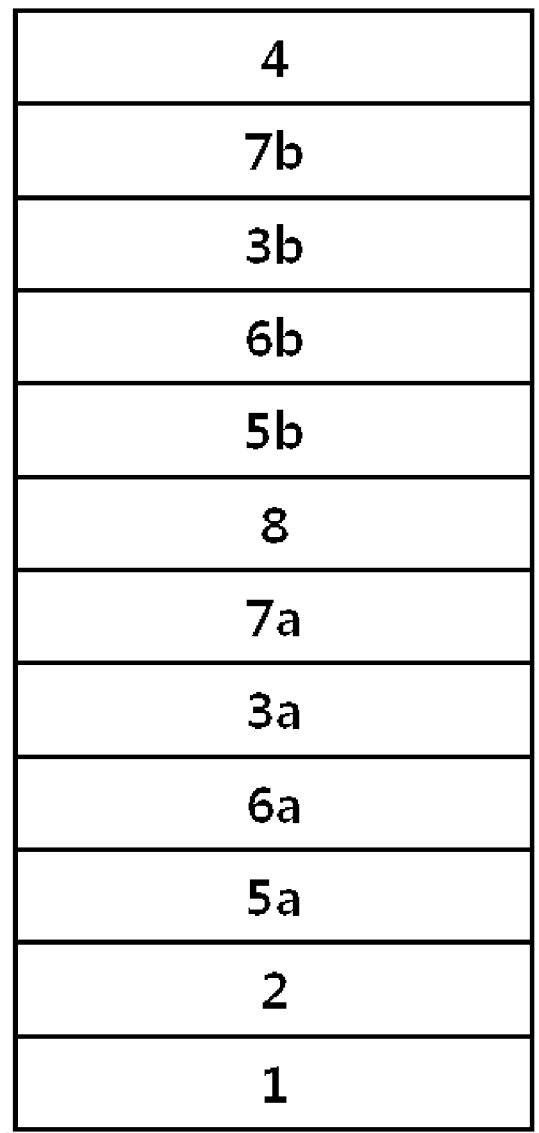

COMPOUND AND ORGANIC ELECTRONIC ELEMENT COMPRISING SAME

CROSS-REFERENCE TO RELATED APPLICATIONS

The present application is a national phase entry under 35 U.S.C. § 371 of International Application No. PCT/KR2016/013273 filed Nov. 17, 2016, which claims priority from Korean Patent Application No. 10-2015-0161034 filed Nov. 17, 2015, all of which are incorporated herein by reference.

TECHNICAL FIELD

The present application relates to a compound and an organic electronic device including the same.

BACKGROUND ART

Representative examples of an organic electronic device include an organic light emitting device. In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

DETAILED DESCRIPTION OF THE INVENTION

Technical Problem

The present invention has been made in an effort to provide a compound which may improve the power consumption and lower the driving voltage in an organic electronic device, and an organic electronic device including the same.

Technical Solution

An exemplary embodiment of the present specification provides a compound represented by the following Chemical Formula 1:

[Chemical Formula 1]

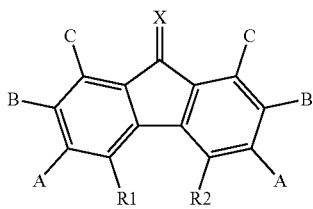

in Chemical Formula 1,

X is represented by any one of the following (a) to (d),

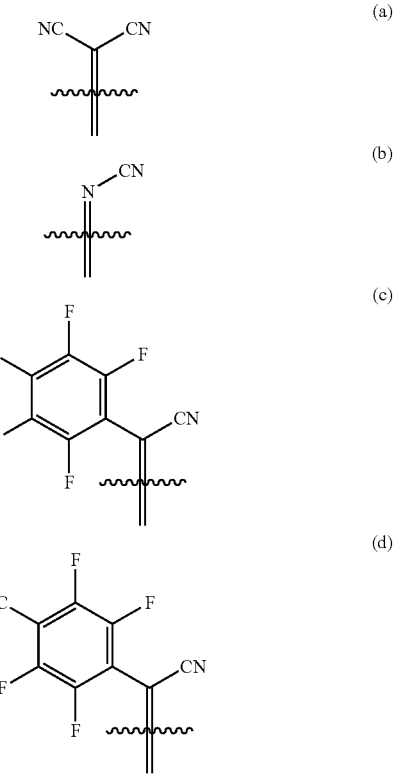

A to C are the same as or different from each other, and are each independently hydrogen; deuterium; a cyano group; a fluoroalkyl group; a fluoroalkoxy group; a substituted or unsubstituted aryl group; or a substituted or unsubstituted heteroaryl group, at least one of A and B is a cyano group; a fluoroalkyl group; or a fluoroalkoxy group, and R1 and R2 are the same as or different from each other, and are each independently hydrogen; deuterium; a halogen group; a cyano group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

Further, an exemplary embodiment of the present specification provides an organic electronic device including: a first electrode; a second electrode provided to face the first electrode; and one or more organic material layers provided between the first electrode and the second electrode, in which one or more layers of the organic material layers include the compound of Chemical Formula 1.

Advantageous Effects

An organic compound of the present invention is applied to a hole injection layer, a hole transport layer, and a P-type charge generation layer to have excellent electron receiving capability and thus induce an increase in power efficiency, thereby having an advantage in that it is possible to provide an organic electronic device which may improve the power consumption and lower the driving voltage.

DESCRIPTION OF DRAWINGS

FIG. 1 illustrates an example of an organic electronic device in which a substrate 1, a positive electrode 2, a light emitting layer 3, and a negative electrode 4 are sequentially stacked.

FIG. 2 illustrates an example of an organic electronic device in which a substrate 1, a positive electrode 2, a hole injection layer 5, a hole transport layer 6, a light emitting layer 3, an electron transport layer 7, and a negative electrode 4 are sequentially stacked.

FIG. 3 illustrates an example of an organic electronic device including a substrate 1, a positive electrode 2, and a negative electrode 4, and including two units including hole injection layers 5a and 5b, hole transport layers 6a and 6b, light emitting layers 3a and 3b, and electron transport layers 7a and 7b between the positive electrode and the negative electrode, in which a charge generation layer 8 is provided between the units.

BEST MODE

Hereinafter, the present specification will be described in more detail.

An exemplary embodiment of the present specification provides the compound represented by Chemical Formula 1. Examples of the substituents will be described below, but are not limited thereto.

When one part "includes" one constituent element in the present specification, unless otherwise specifically described, this does not mean that another constituent element is excluded, but means that another constituent element may be further included.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a nitro group; an imide group; an amide group; a carbonyl group; an ester group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heteroaryl group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In the present specification, ⌇ means a moiety bonded to another substituent or a bonding portion.

In the present specification, a halogen group may be fluorine, chlorine, bromine, or iodine.

In the present specification, the number of carbon atoms of an imide group is not particularly limited, but is preferably 1 to 30. Specifically, the imide group may be a compound having the following structures, but is not limited thereto.

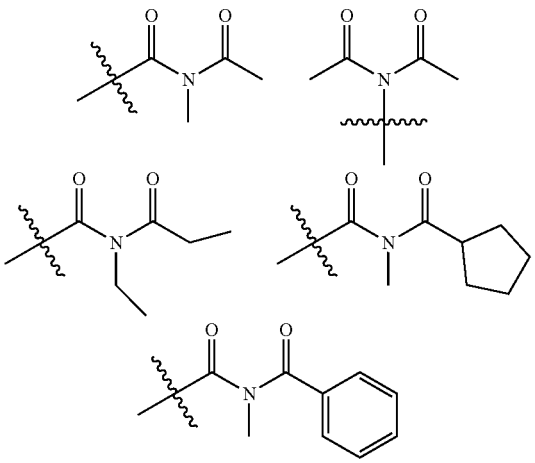

In the present specification, for an amide group, the nitrogen of the amide group may be substituted with hydrogen, a straight-chained, branch-chained, or cyclic alkyl group having 1 to 30 carbon atoms, or an aryl group having 6 to 30 carbon atoms. Specifically, the amide group may be a compound having the following structural formulae, but is not limited thereto.

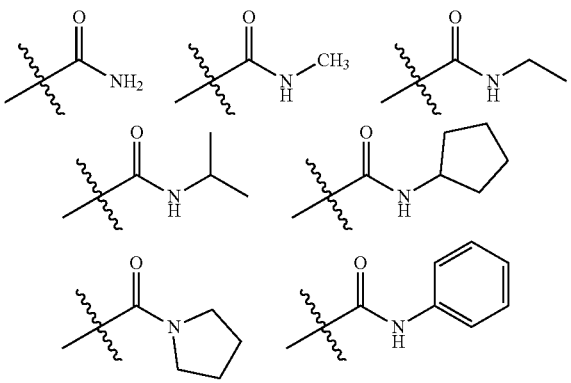

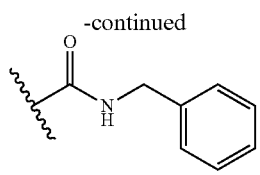

In the present specification, the number of carbon atoms of a carbonyl group is not particularly limited, but is preferably 1 to 30. Specifically, the carbonyl group may be a compound having the following structures, but is not limited thereto.

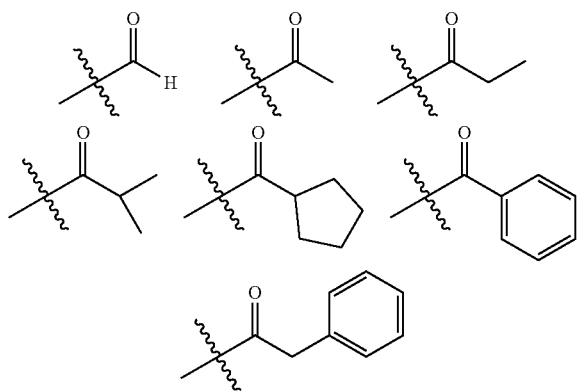

In the present specification, for an ester group, the oxygen of the ester group may be substituted with a straight-chained, branch-chained, or cyclic alkyl group having 1 to 25 carbon atoms, or an aryl group having 6 to 30 carbon atoms. Specifically, the ester group may be a compound having the following structural formulae, but is not limited thereto.

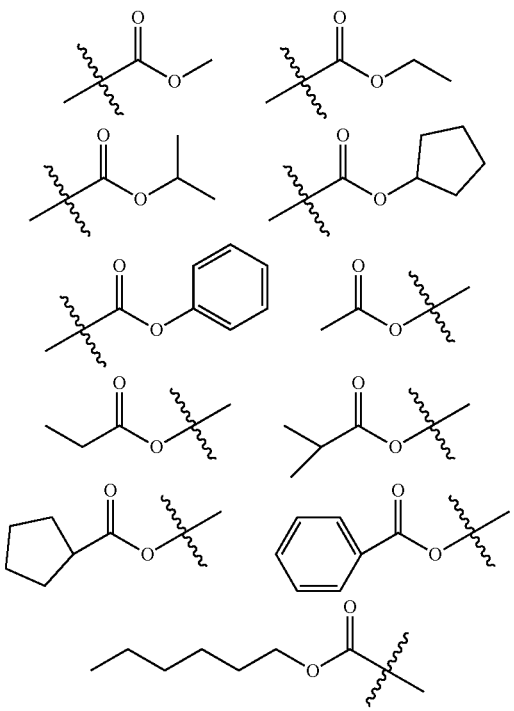

In the present specification, the alkyl group may be straight-chained or branch-chained, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branch-chained, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group may be selected from the group consisting of —NH$_2$; a monoalkylamine group; a dialkylamine group; an N-alkylarylamine group; a monoarylamine group; a diarylamine group; an N-arylheteroarylamine group; an N-alkylheteroarylamine group, a monoheteroarylamine group, and a diheteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenyl terphenylamine group; an N-phenanthrenylfluorenylamine group; an N-biphenylfluorenylamine group, and the like, but are not limited thereto.

In the present specification, the N-alkylarylamine group means an amine group in which an alkyl group and an aryl group are substituted with N of the amine group. In the present specification, an N-arylheteroarylamine group means an amine group in which an aryl group and a heteroaryl group are substituted with N of the amine group.

In the present specification, an N-alkylheteroarylamine group means an amine group in which an alkyl group and a heteroaryl group are substituted with N of the amine group.

In the present specification, the alkyl group in the alkylamine group, the N-alkylarylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but the examples are not limited thereto.

In the present specification, the alkenyl group may be straight-chained or branch-chained, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be —$BR_{100}R_{101}$, and $R_{100}$ and $R_{101}$ are the same as or different from each other, and may be each independently selected from the group consisting of hydrogen; deuterium; halogen; a cyano group; a substituted or unsubstituted monocyclic or polycyclic cycloalkyl group having 3 to 30 carbon atoms; a substituted or unsubstituted straight-chained or branch-chained alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of a phosphine oxide group include a diphenylphosphine oxide group, dinaphthylphosphine oxide group, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a perylenyl group, a chrysenyl group, a fluorenyl group, and the like, but are not limited thereto.

In the present specification, the fluorenyl group may be substituted, and adjacent substituents may combine) with each other to form a ring.

When the fluorenyl group is substituted, the fluorenyl group may be

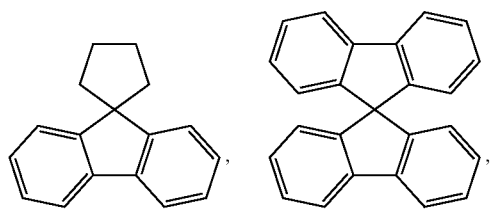

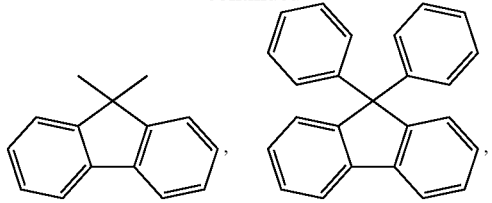

and the like. However, the fluorenyl group is not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, a heteroaryl group includes one or more of an atom other than carbon, that is, a heteroatom, and specifically, the heteroatom may include one or more atoms selected from the group consisting of O, N, Se, and S, and the like. The number of carbon atoms thereof is not particularly limited, but is preferably 2 to 30, and the heteroaryl group may be monocyclic or polycyclic. Examples of the heteroaryl group include a thiophene group, a furanyl group, a pyrrole group, an imidazolyl group, a triazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, examples of the heteroaryl group in the N-arylheteroarylamine group and the N-alkylheteroarylamine group are the same as the above-described examples of the heteroaryl group.

In the present specification, the heteroaryl group may be monocyclic or polycyclic, may be an aromatic ring, an aliphatic ring, or a fused ring of the aromatic ring and the aliphatic ring, and may be selected from the examples of the heteroaryl group.

In the present specification, an aromatic ring group may be monocyclic or polycyclic, and may be selected from the examples of the aryl group.

In the present specification, a divalent to tetravalent aromatic ring group may be monocyclic or polycyclic, and means a group having 2 to 4 bonding positions in the aryl group, that is, a divalent to tetravalent group. The above-described description on the aryl group may be applied to the aromatic ring group, except for a divalent to tetravalent aromatic ring group.

In the present specification, the alkylene group means a group having two bonding positions in an alkyl group, that is, a divalent group. The above-described description on the alkyl group may be applied to the alkylene group, except for a divalent alkylene group.

In the present specification, the cycloalkylene group means a group having two bonding positions in a cycloalkyl group, that is, a divalent group. The above-described description on the cycloalkyl group may be applied to the cycloalkylene groups, except for a divalent cycloalkylene group.

In the present specification, the arylene group means a group having two bonding positions in an aryl group, that is, a divalent group. The above-described description on the aryl group may be applied to the arylene group, except for a divalent arylene group.

In the present specification, the heteroarylene group means a group having two bonding positions in a heteroaryl group, that is, a divalent group. The above-described description on the heteroaryl group may be applied to the heteroarylene group, except for a divalent heteroarylene group.

In the present specification, the meaning of "two adjacent substituents combine with each other to form a ring" among the substituents is that a substituent combines with an adjacent group to form a substituted or unsubstituted hydrocarbon ring; or a substituted or unsubstituted heteroaryl.

In the present specification, a ring means a substituted or unsubstituted hydrocarbon ring; or a substituted or unsubstituted heteroaryl.

In the present specification, a hydrocarbon ring may be an aromatic ring, an aliphatic ring, or a fused ring of the aromatic ring and the aliphatic ring, and may be selected from the examples of the cycloalkyl group or the aryl group, except for the hydrocarbon ring which is not monovalent.

In the present specification, an aromatic ring may be monocyclic or polycyclic, and may be selected from the examples of the aryl group, except for the aromatic ring which is not monovalent.

In the present specification, a heteroaryl includes one or more of an atom other than carbon, that is, a heteroatom, and specifically, the heteroatom may include one or more atoms selected from the group consisting of O, N, Se, and S, and the like. The heteroaryl may be monocyclic or polycyclic, may be an aromatic ring, an aliphatic ring, or a fused ring of the aromatic ring and the aliphatic ring, and may be selected from the examples of the heteroaryl group, except for the hetero ring which is not monovalent.

In the present specification, in a substituted or unsubstituted ring formed by combining adjacent groups, the "ring" means a substituted or unsubstituted hydrocarbon ring; or a substituted or unsubstituted heteroaryl group.

In the present specification, a divalent to tetravalent aromatic ring group may be monocyclic or polycyclic, and means a group having 2 to 4 bonding positions in the aryl group, that is, a divalent to tetravalent group. The above-described description on the aryl group may be applied to the aromatic ring group, except for a divalent to tetravalent aromatic ring group.

According to an exemplary embodiment of the present specification, As are the same as each other.

According to an exemplary embodiment of the present specification, Bs are the same as each other.

According to an exemplary embodiment of the present specification, Cs are the same as each other.

According to an exemplary embodiment of the present specification, A and B is —CN, —$C_nF_{2n+1}$, or —O—$C_nF_{2n+1}$, and n is 1 or 2.

According to an exemplary embodiment of the present specification, A is —CN.

According to an exemplary embodiment of the present specification, A is —$CF_3$.

According to an exemplary embodiment of the present specification, A is —$C_2F_5$.

According to an exemplary embodiment of the present specification, A is —$OCF_3$.

According to an exemplary embodiment of the present specification, A is —$OC_2F_5$.

In an exemplary embodiment of the present specification, A is a substituted or unsubstituted aryl group.

According to an exemplary embodiment of the present specification, A is a substituted or unsubstituted phenyl group; or a substituted or unsubstituted biphenyl group; or a substituted or unsubstituted naphthalene group.

According to an exemplary embodiment of the present specification, A is a phenyl group which is unsubstituted or substituted with at least one or more substituents selected from the group consisting of fluorine; —CN; —$CF_3$; —$OCF_3$; —$OCHF_2$; —$OC_2F_5$; —$OCH_2C_2F_5$; —$OCH(CF_3)_2$; —$C_8F_{17}$, and —$Si(CH_3)_3$.

According to an exemplary embodiment of the present specification, A is a biphenyl group which is unsubstituted or substituted with at least one or more substituents selected from the group consisting of fluorine; —CN, and —$CF_3$.

According to an exemplary embodiment of the present specification, A is a substituted or unsubstituted heteroaryl group.

According to an exemplary embodiment of the present specification, A is a substituted or unsubstituted pyridine group; a substituted or unsubstituted quinoline group; a substituted or unsubstituted quinazoline group; or a substituted or unsubstituted quinoxaline group.

According to an exemplary embodiment of the present specification, A is a pyridine group.

According to an exemplary embodiment of the present specification, A is a pyridine group substituted with fluorine.

According to an exemplary embodiment of the present specification, A is a quinoxaline group.

According to an exemplary embodiment of the present specification, A is a quinoxaline group substituted with a cyano group.

According to an exemplary embodiment of the present specification, A is a quinazoline group.

According to an exemplary embodiment of the present specification, A is a quinazoline group substituted with a cyano group.

According to an exemplary embodiment of the present specification, A is a quinoline group.

According to an exemplary embodiment of the present specification, A is a quinoline group.

According to an exemplary embodiment of the present specification, B is —CN.

According to an exemplary embodiment of the present specification, B is —CF$_3$.

According to an exemplary embodiment of the present specification, B is —C$_2$F$_5$.

According to an exemplary embodiment of the present specification, B is —OCF$_3$.

According to an exemplary embodiment of the present specification, B is —OC$_2$F$_5$.

According to an exemplary embodiment of the present specification, B is a substituted or unsubstituted aryl group.

According to an exemplary embodiment of the present specification, B is a substituted or unsubstituted phenyl group; or a substituted or unsubstituted biphenyl group; or a substituted or unsubstituted naphthalene group.

According to an exemplary embodiment of the present specification, B is a phenyl group which is unsubstituted or substituted with at least one or more substituents selected from the group consisting of fluorine; —CN; —CF$_3$; —OCF$_3$; —OCHF$_2$; —OC$_2$F$_5$; —OCH$_2$C$_2$F$_5$; —OCH(CF$_3$)$_2$; —C$_8$F$_{17}$, and —Si(CH$_3$)$_3$.

According to an exemplary embodiment of the present specification, B is a biphenyl group which is unsubstituted or substituted with at least one or more substituents selected from the group consisting of fluorine; —CN, and —CF$_3$.

According to an exemplary embodiment of the present specification, B is a substituted or unsubstituted heteroaryl group.

According to an exemplary embodiment of the present specification, B is a substituted or unsubstituted pyridine group; a substituted or unsubstituted quinoline group; a substituted or unsubstituted quinazoline group; or a substituted or unsubstituted quinoxazoline group.

According to an exemplary embodiment of the present specification, B is a pyridine group.

According to an exemplary embodiment of the present specification, B is a pyridine group substituted with fluorine.

According to an exemplary embodiment of the present specification, B is a quinoxaline group.

According to an exemplary embodiment of the present specification, B is a quinoxaline group substituted with a cyano group.

According to an exemplary embodiment of the present specification, B is a quinazoline group.

According to an exemplary embodiment of the present specification, B is a quinazoline group substituted with a cyano group.

According to an exemplary embodiment of the present specification, B is a quinoline group.

According to an exemplary embodiment of the present specification, C is hydrogen.

According to an exemplary embodiment of the present specification, C is —CN.

According to an exemplary embodiment of the present specification, R1 and R2 are hydrogen.

According to an exemplary embodiment of the present invention, the compound of Chemical Formula 1 may be selected from the following structural formulae.

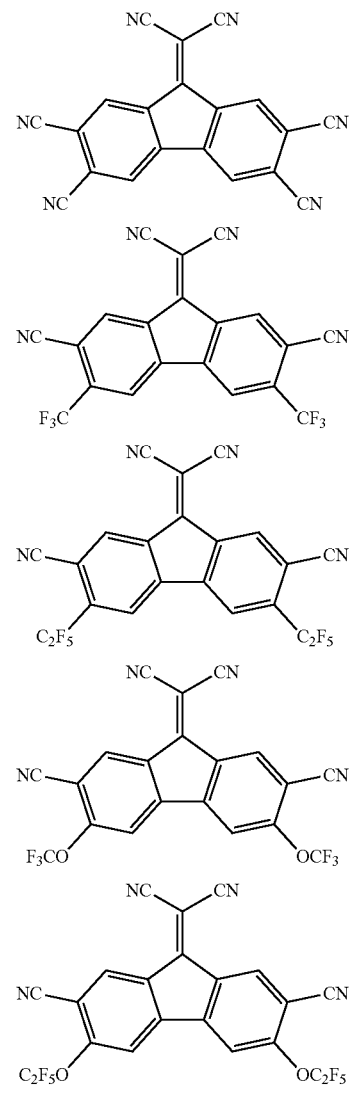

-continued
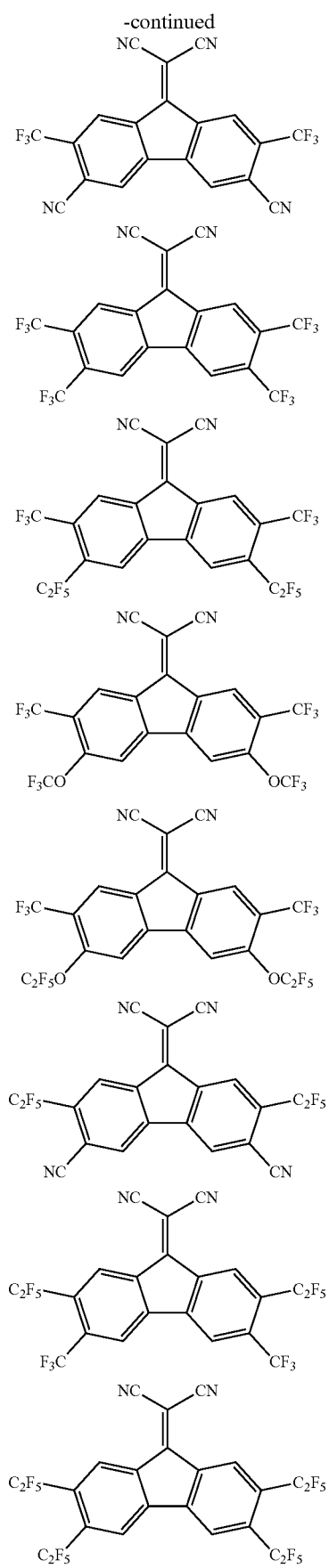
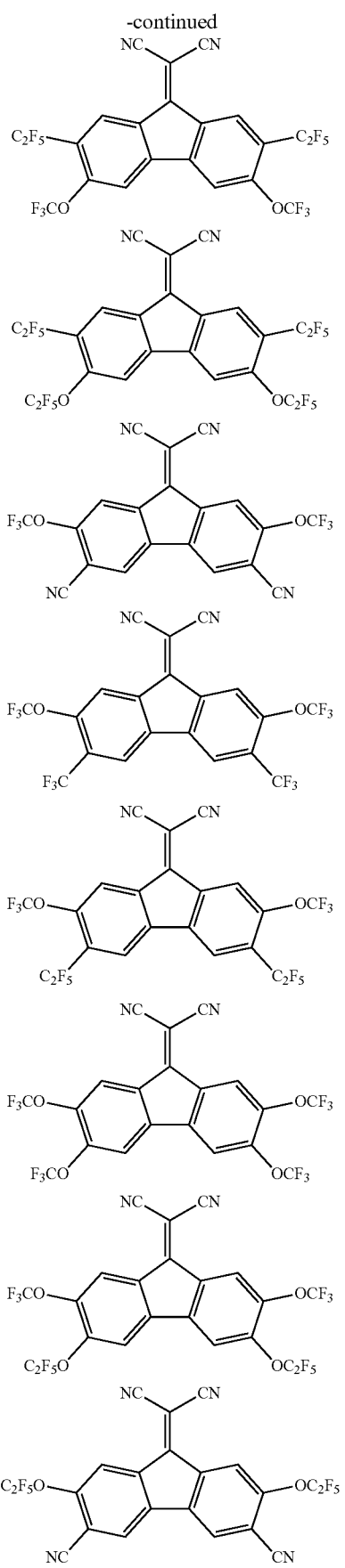

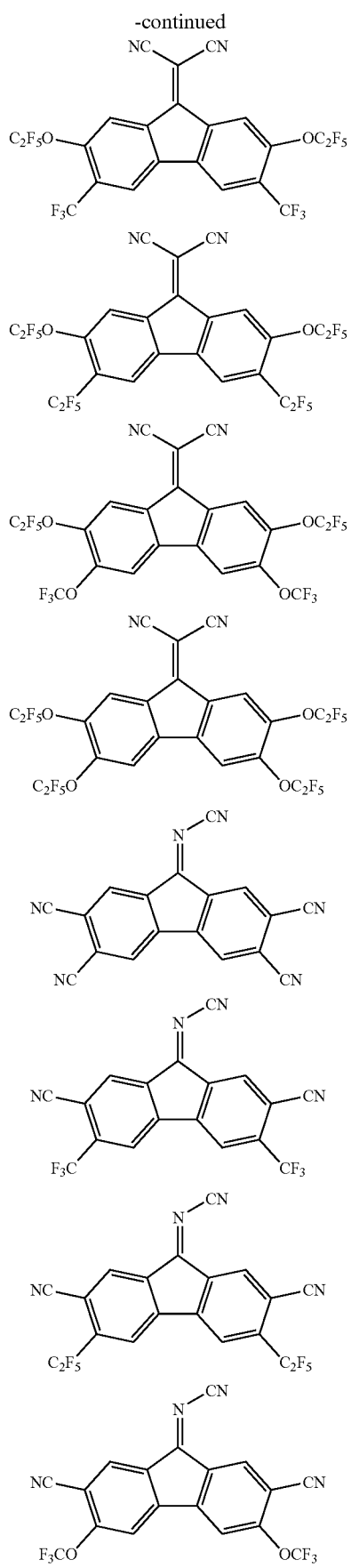
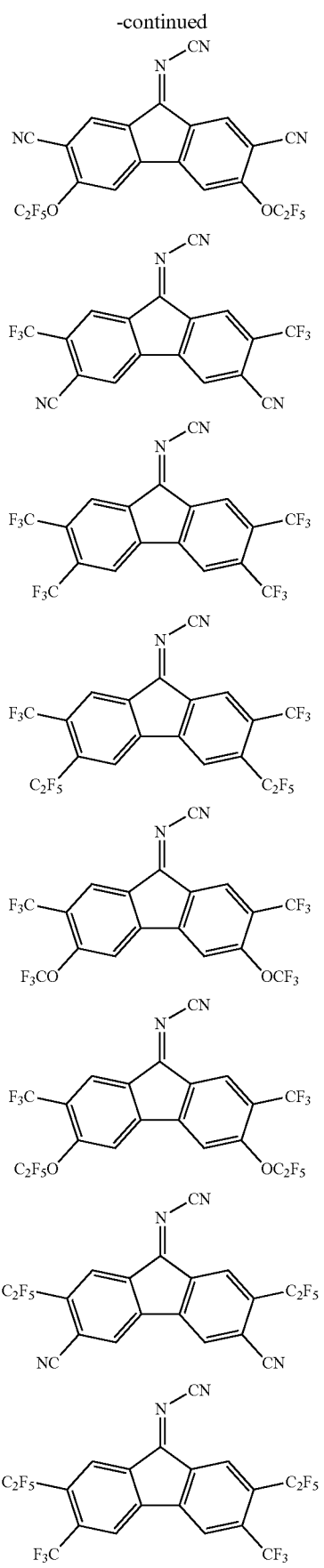

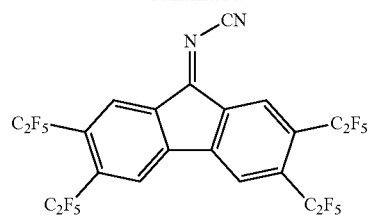
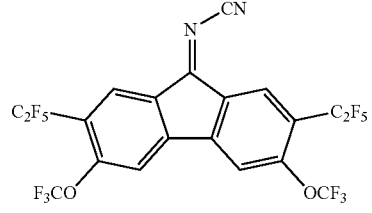
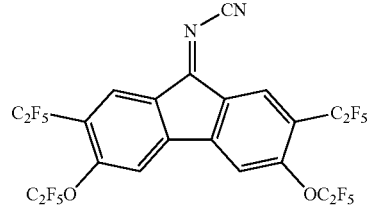
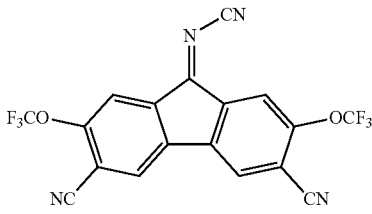
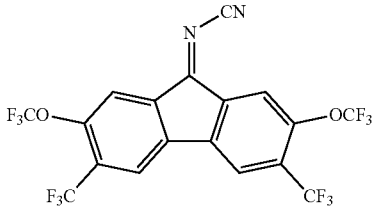
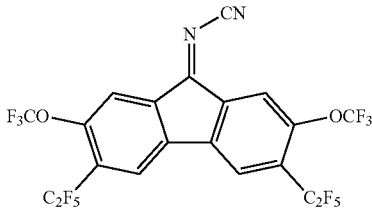
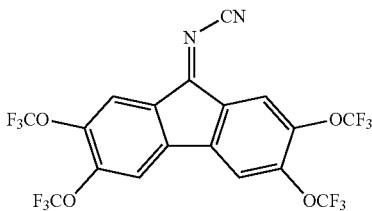
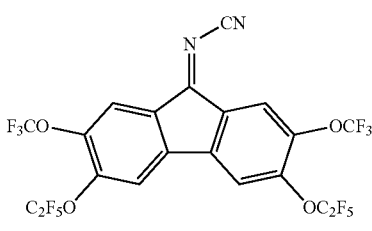
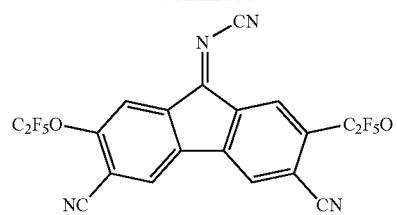
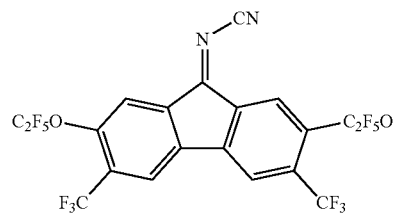
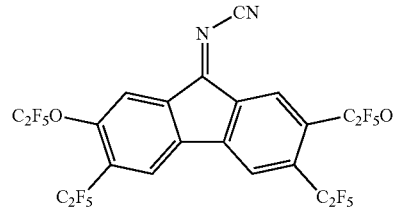
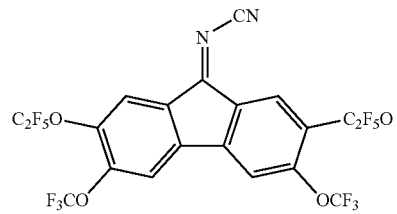
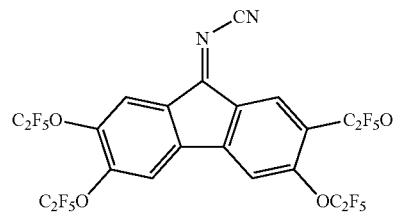
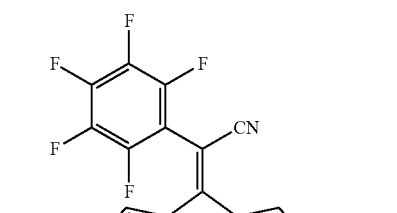
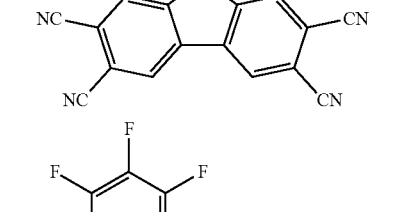
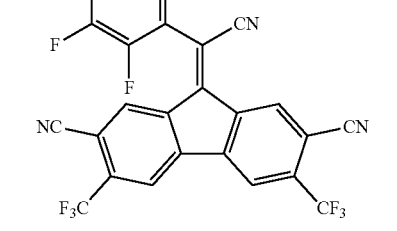

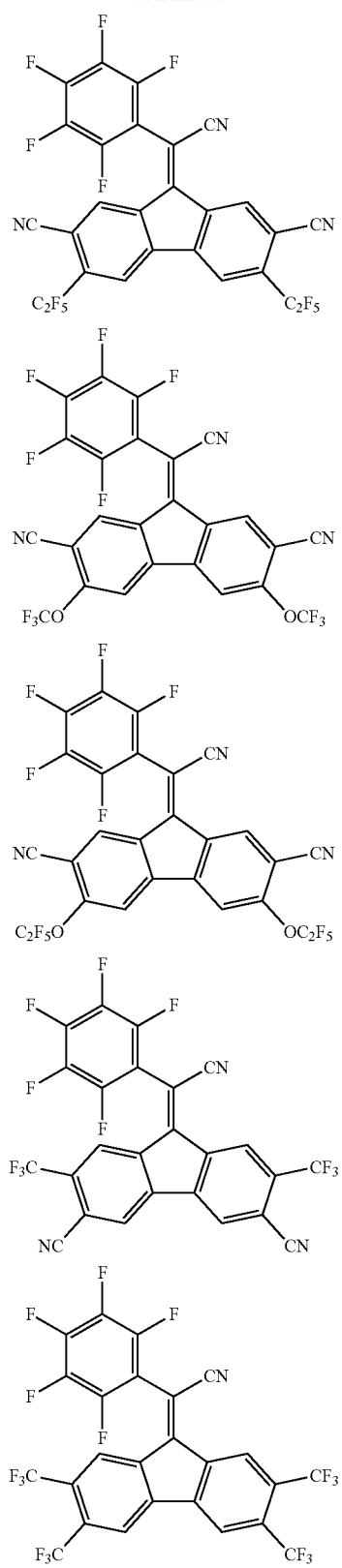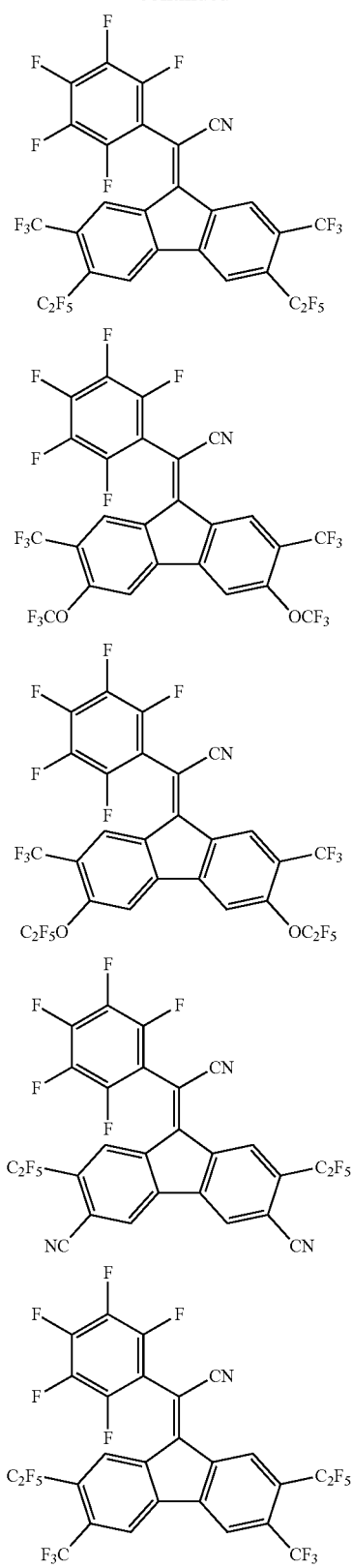

-continued
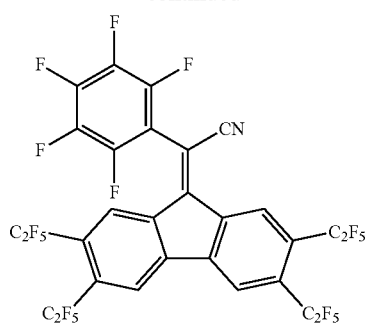
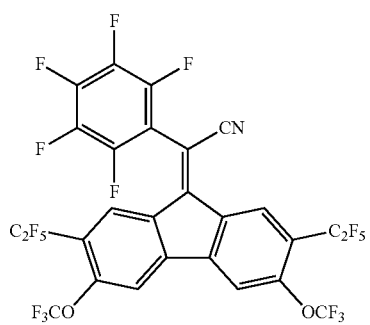
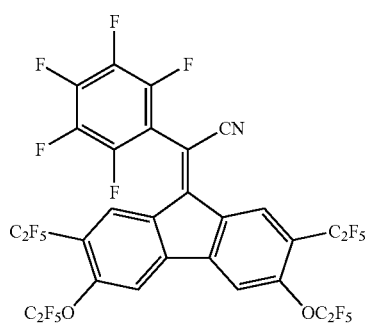
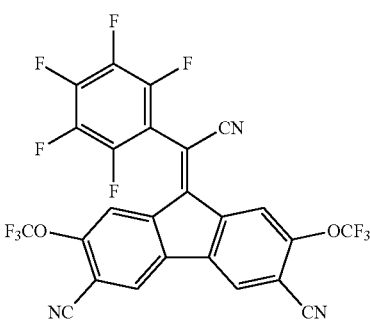
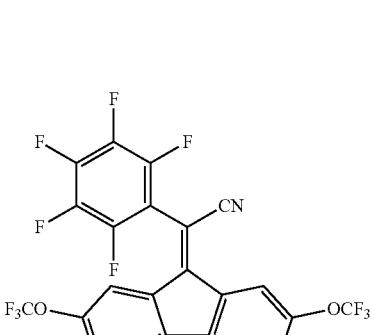
-continued
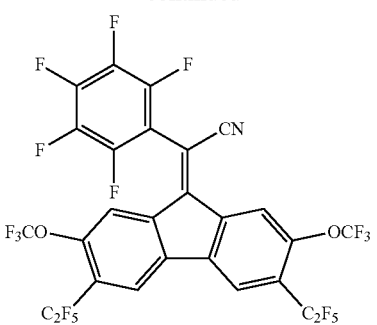
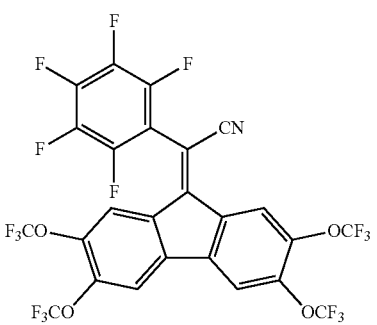
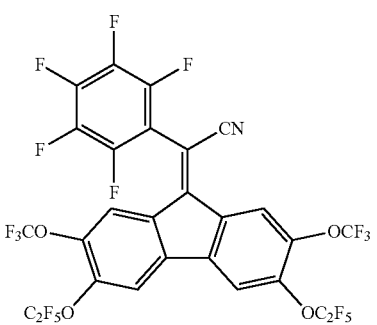
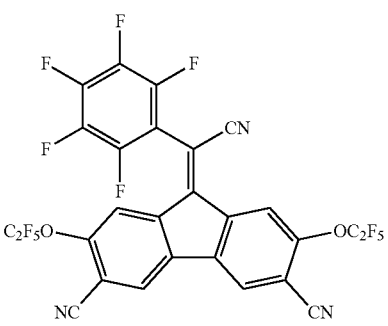
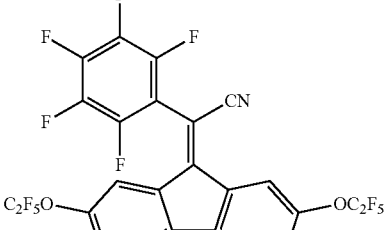

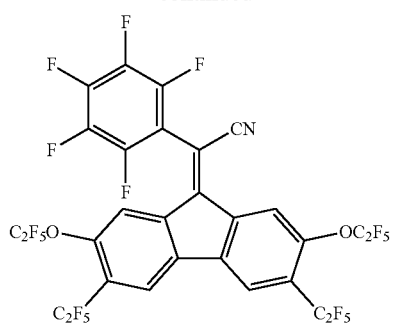
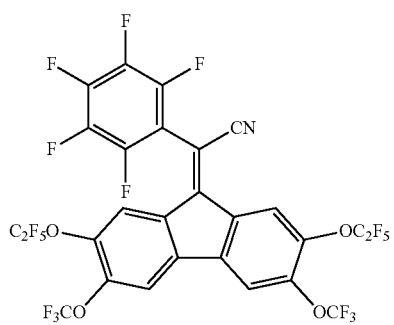
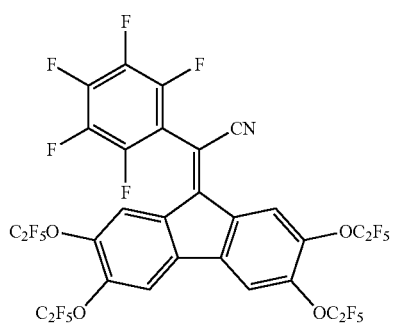
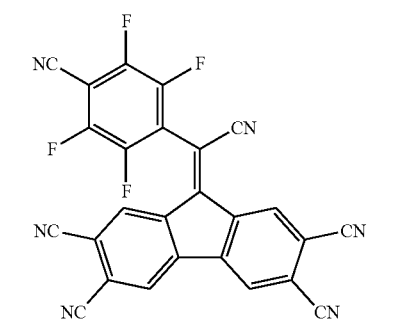
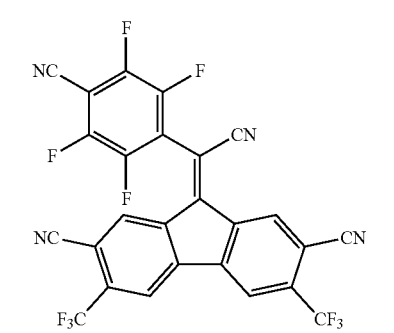
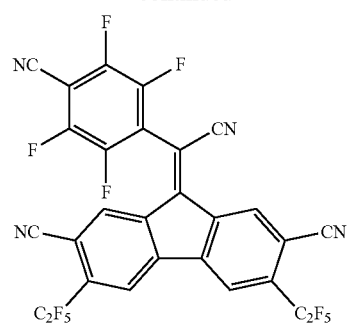
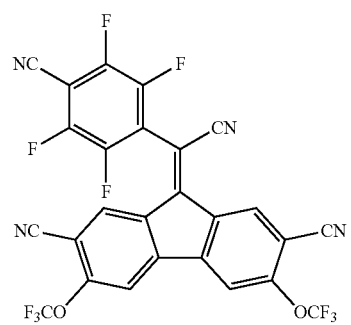
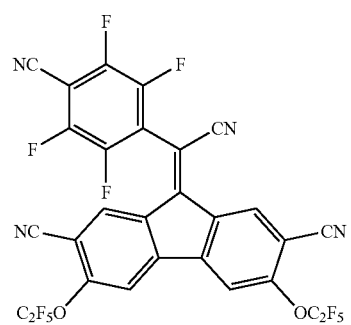
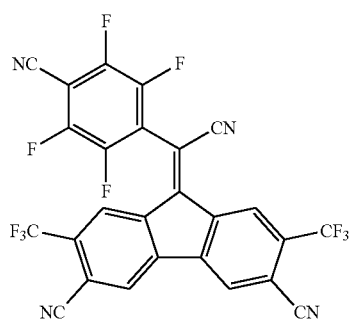
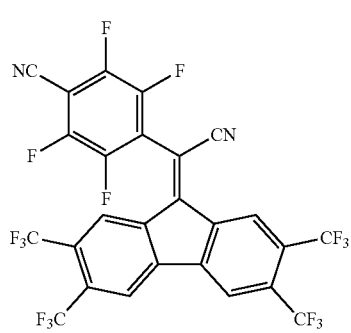

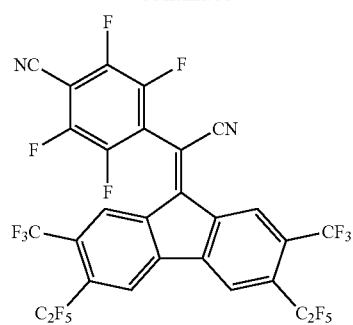
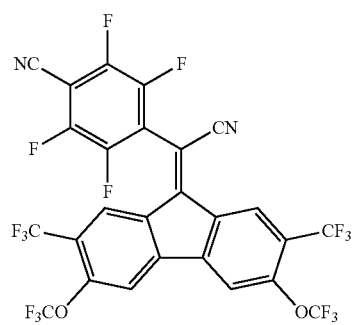
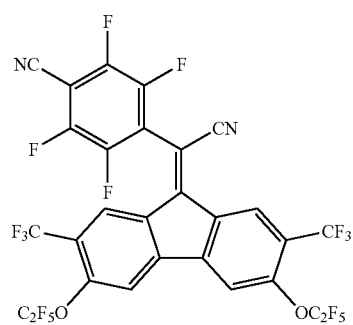
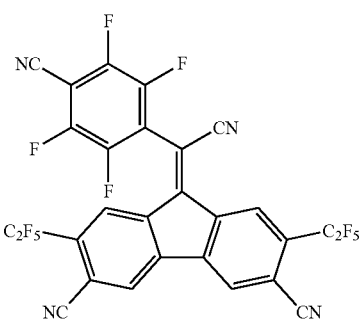
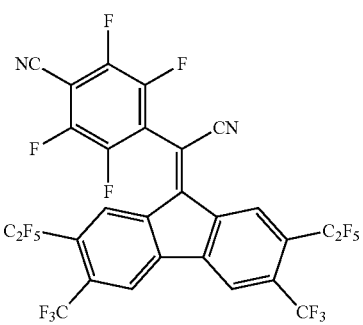
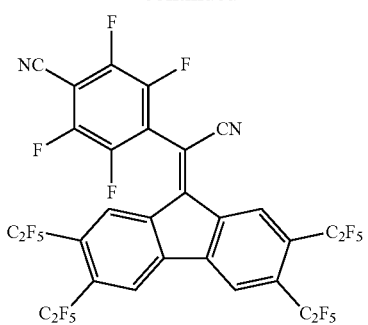
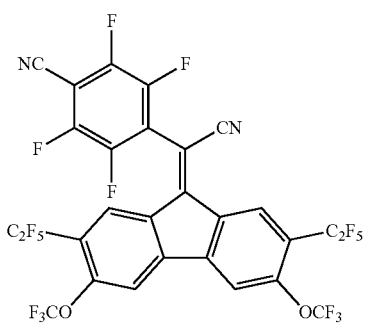
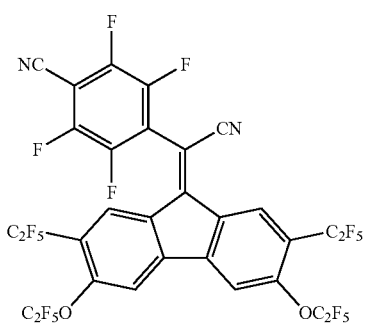
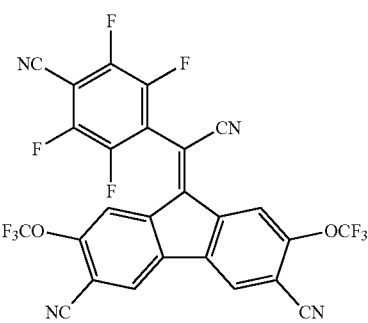
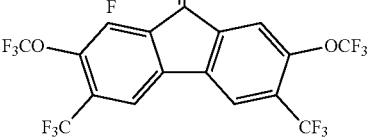

-continued
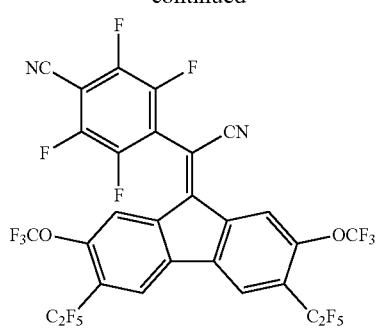
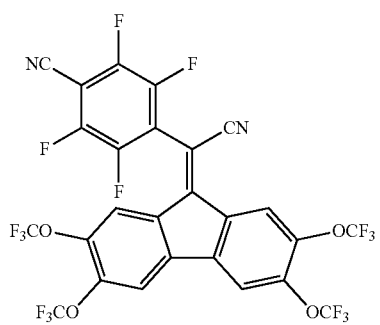
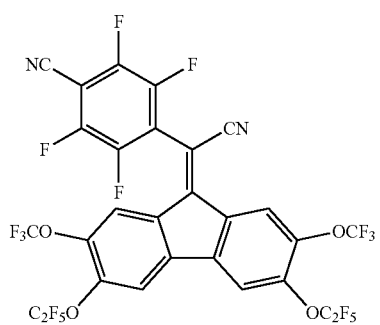
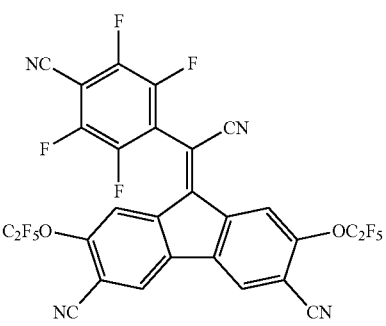
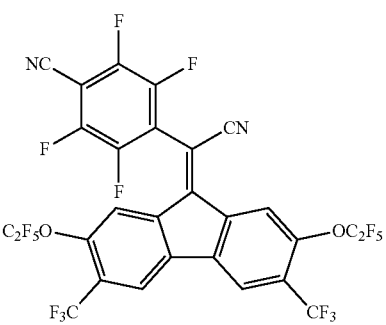
-continued
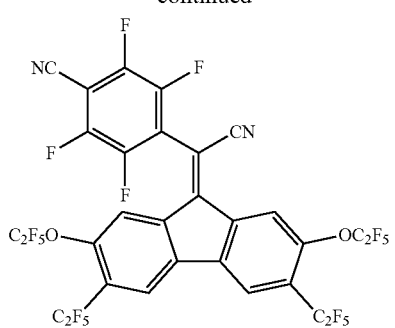
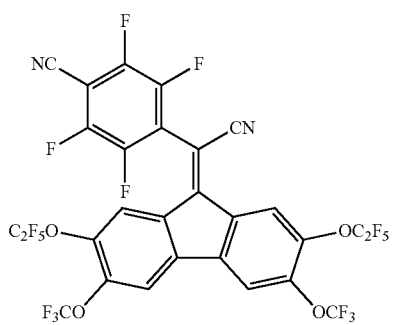
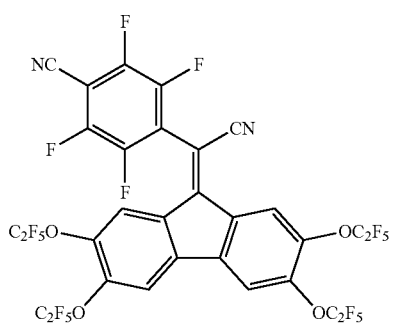
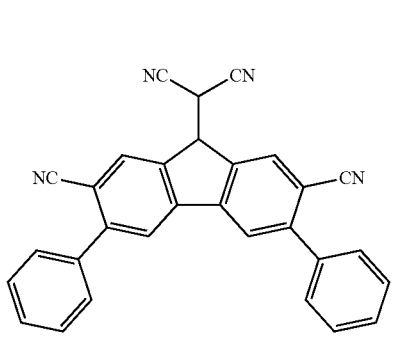
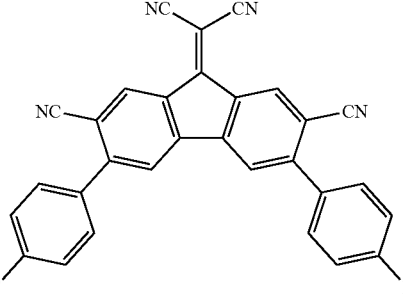

-continued
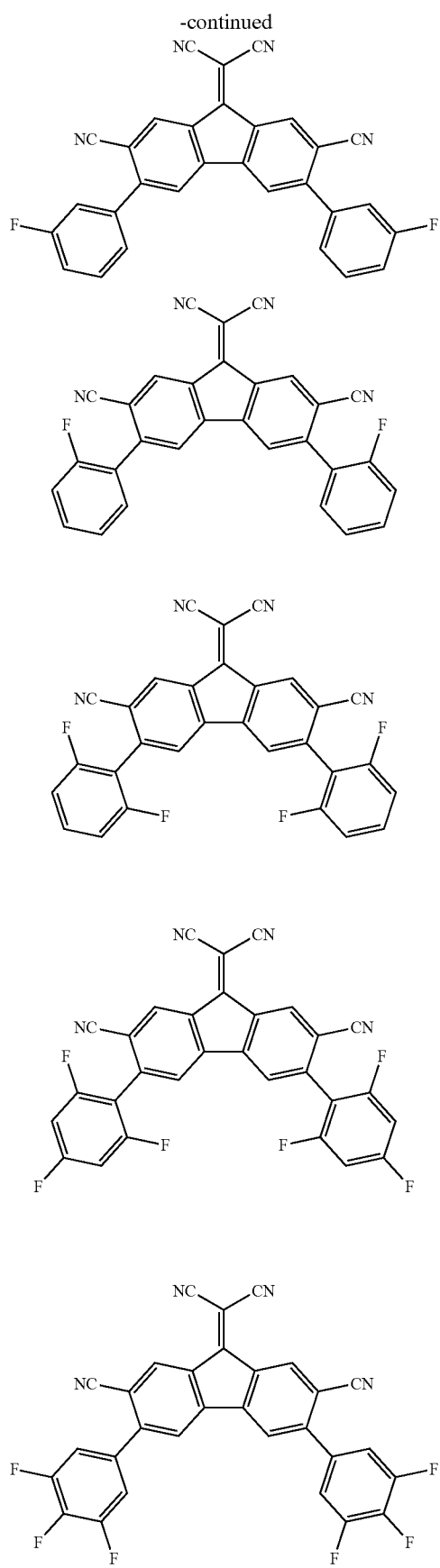
-continued
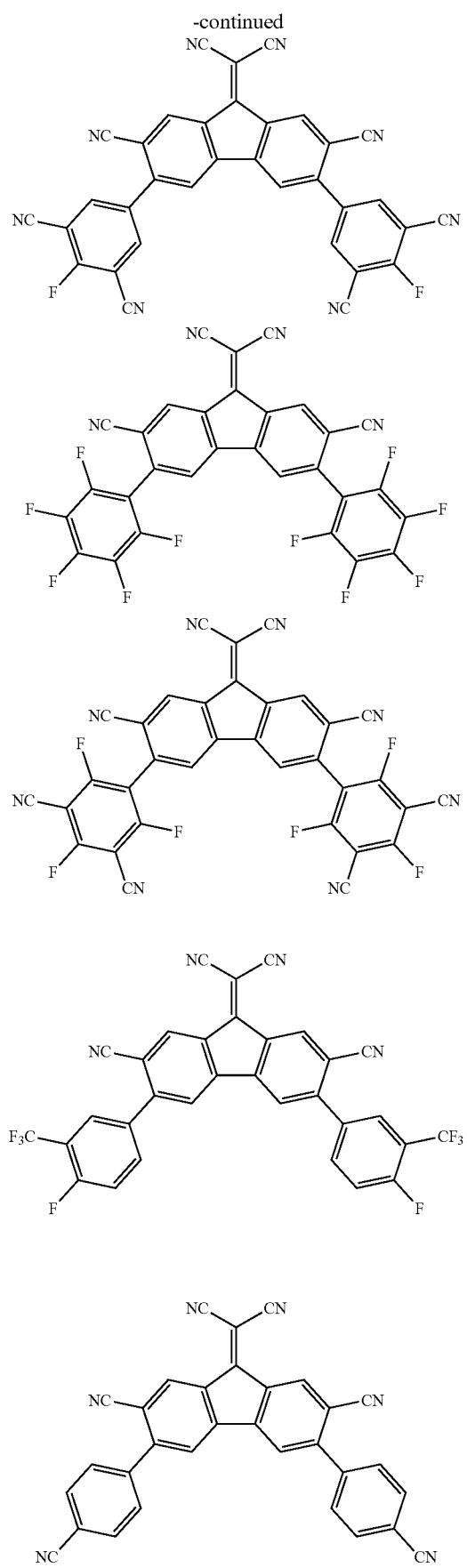

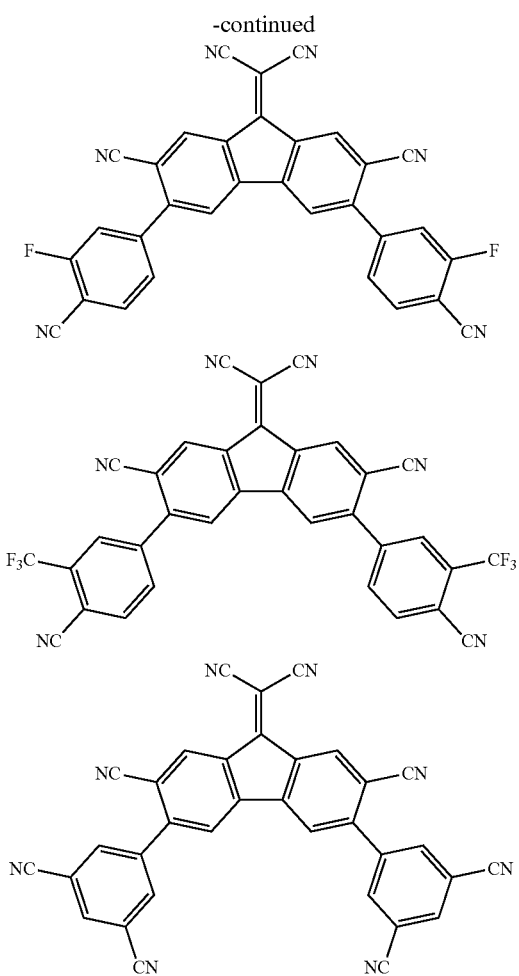
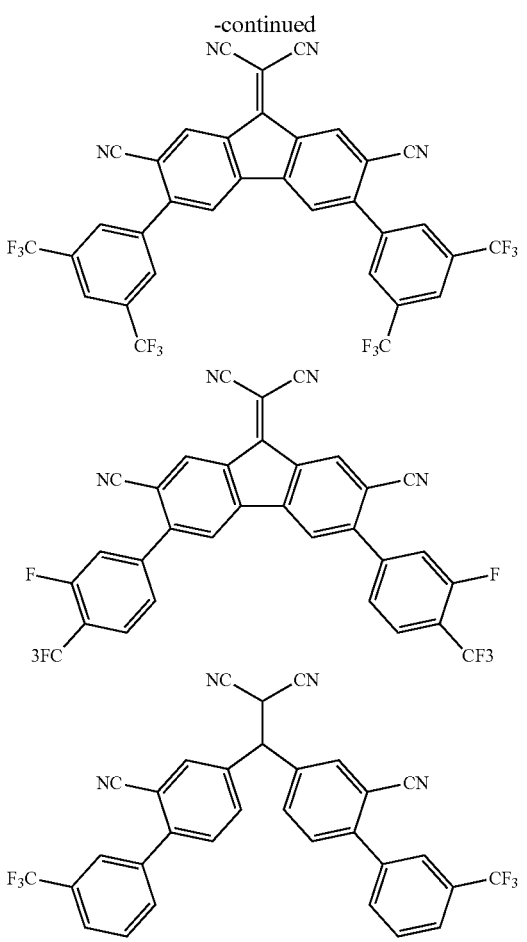
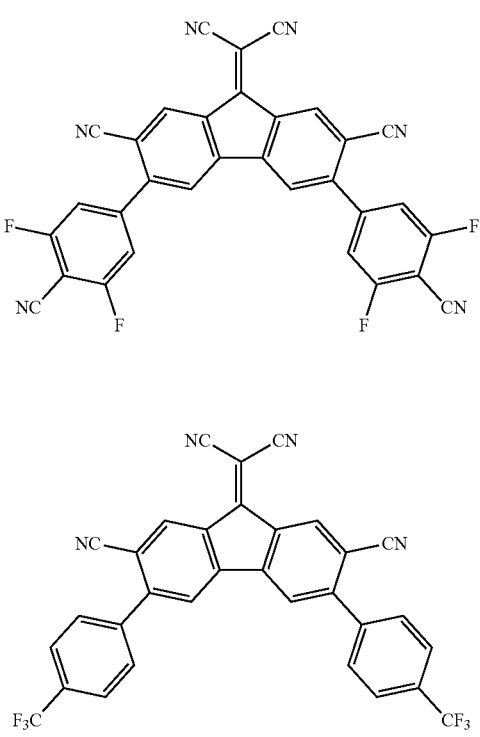
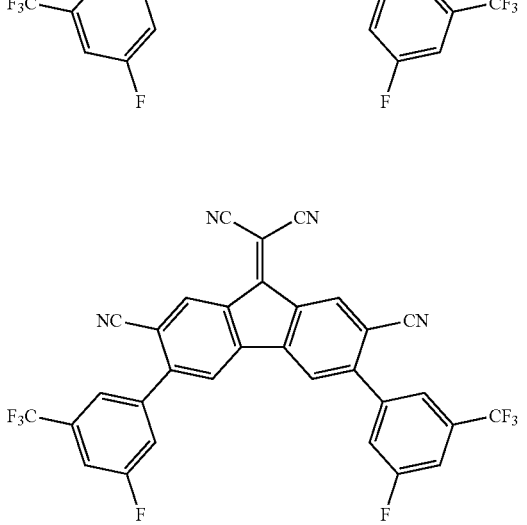

-continued
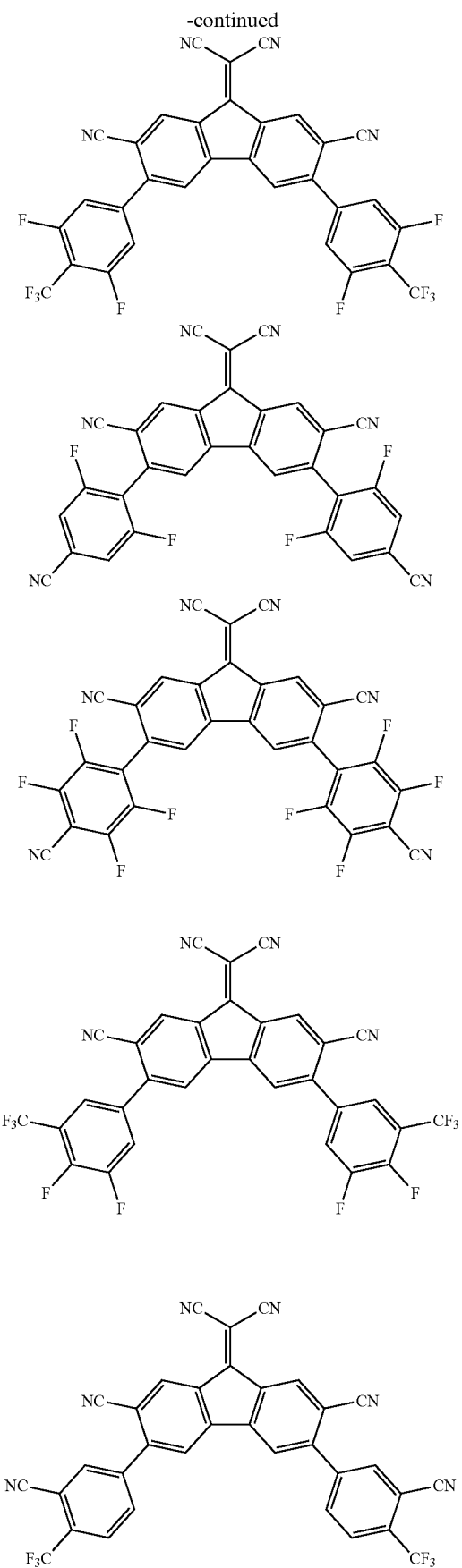
-continued
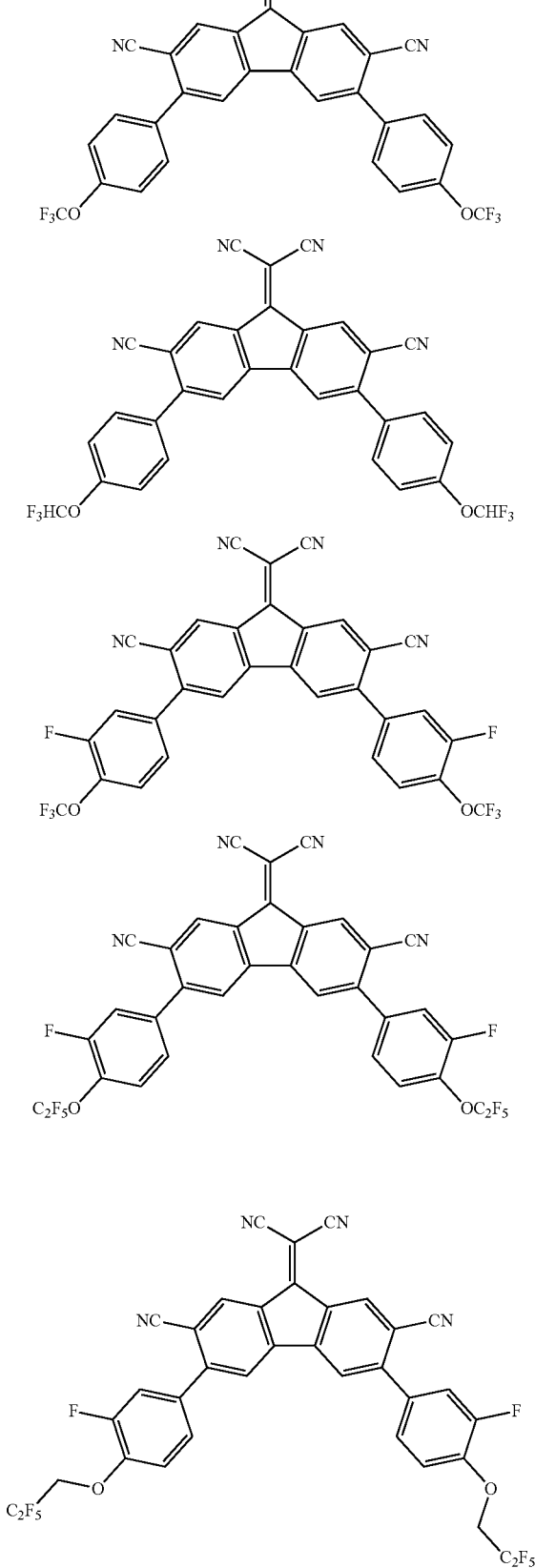

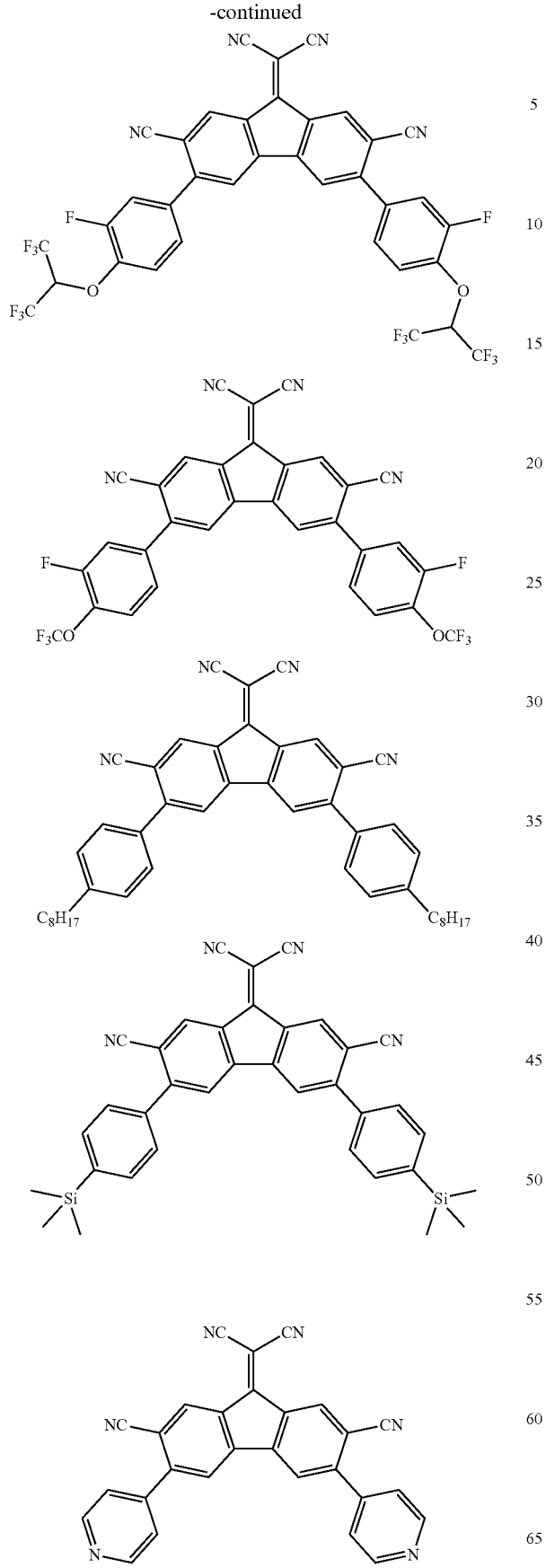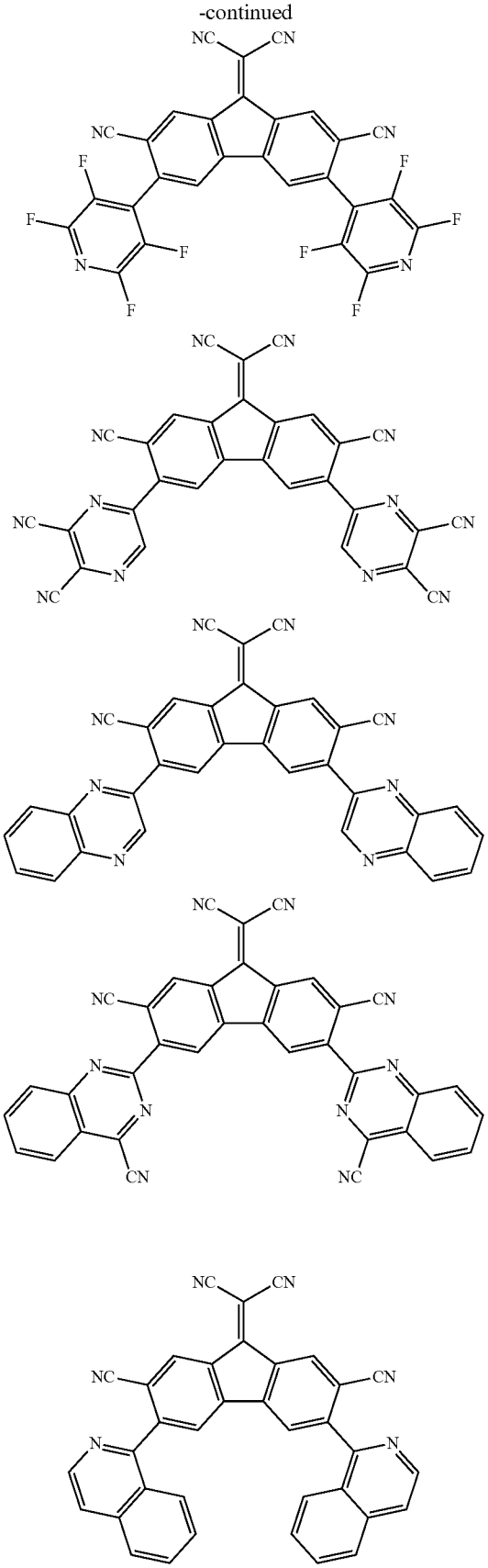

-continued
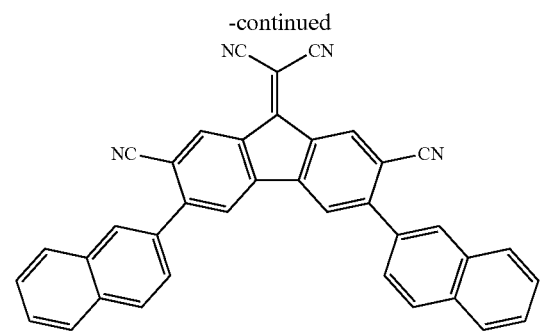
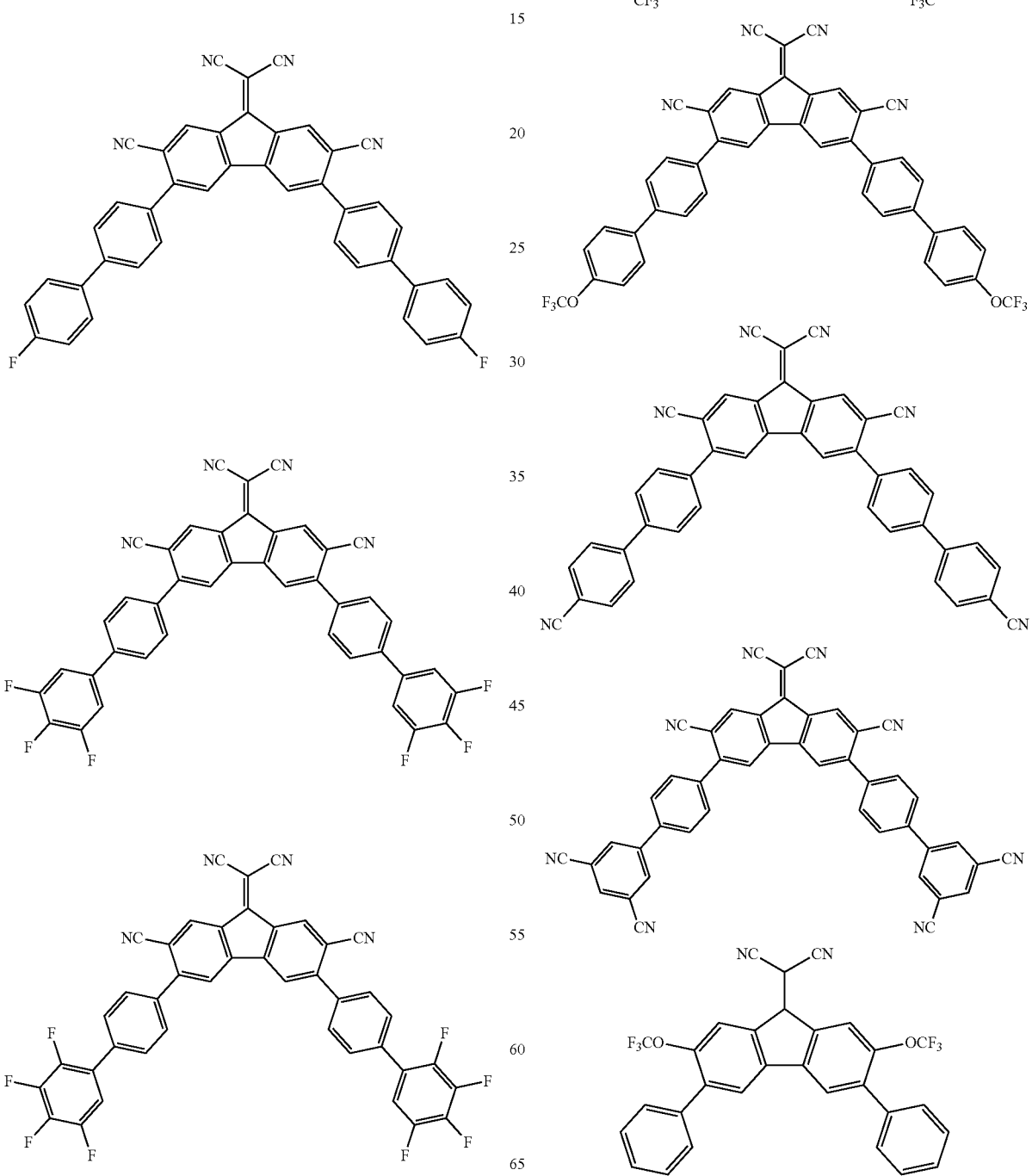

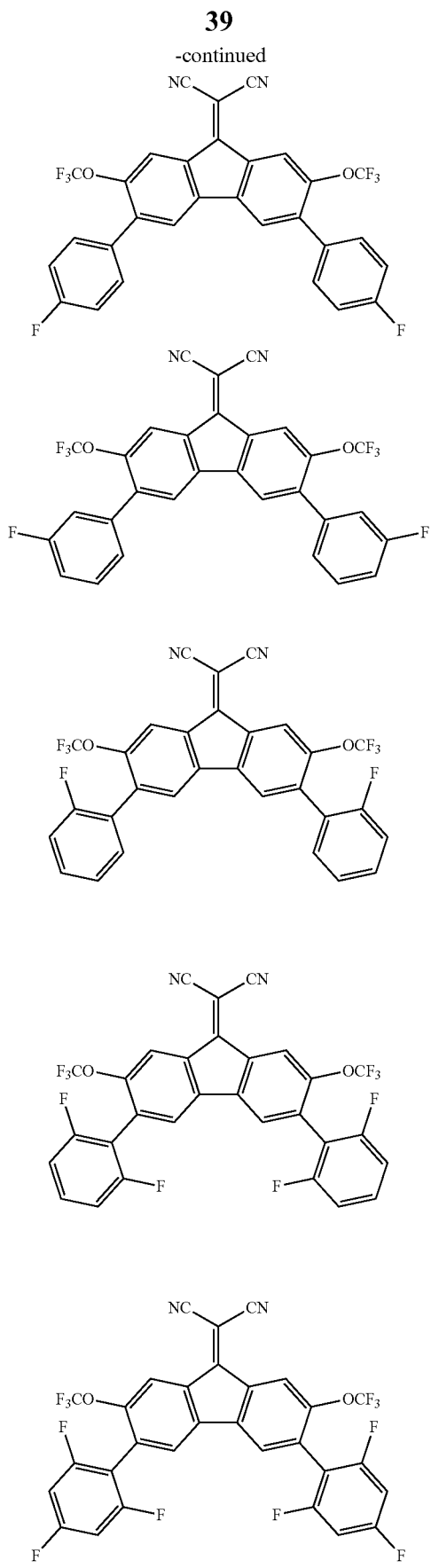

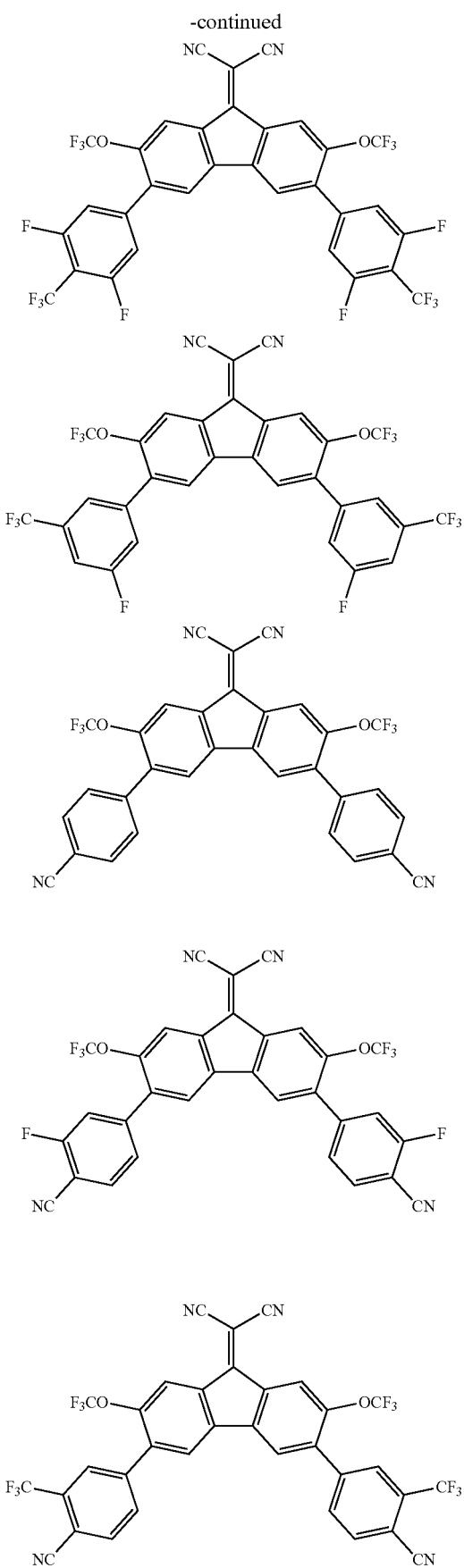
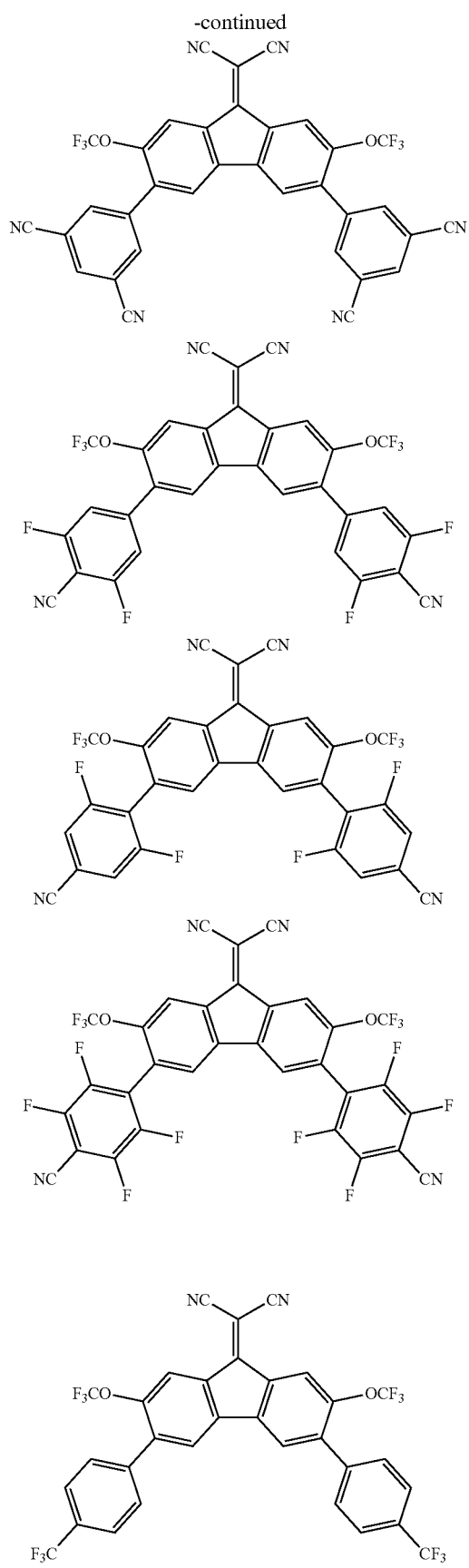

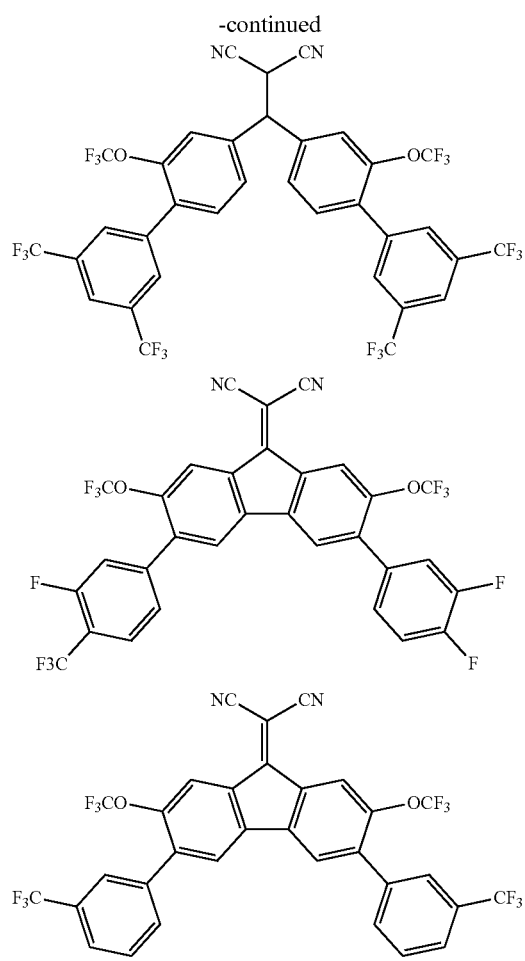
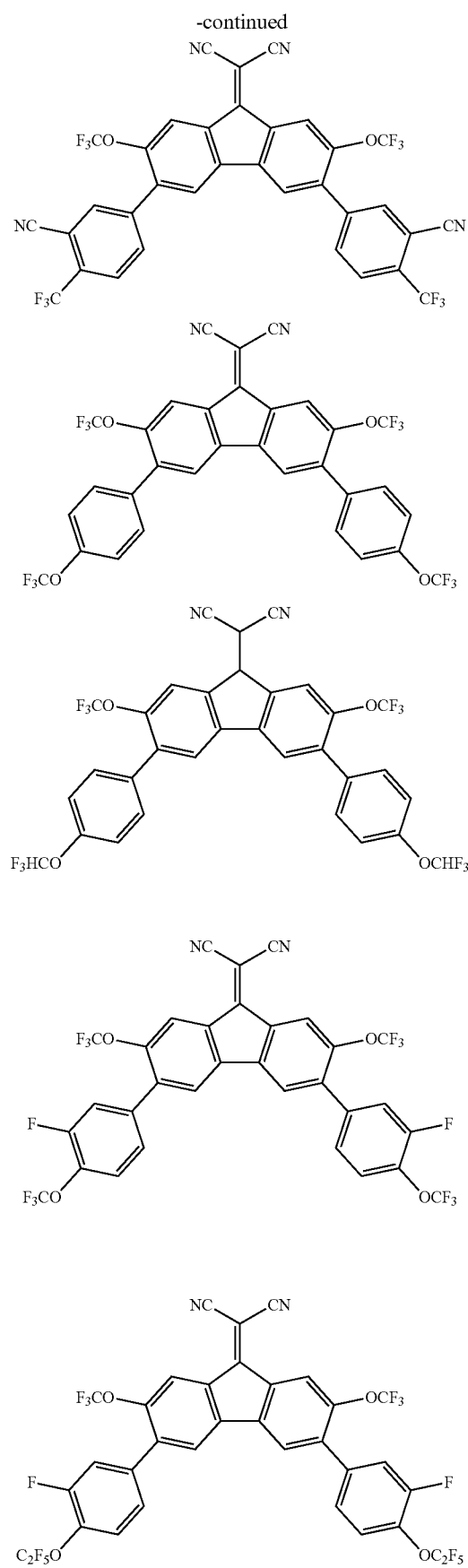

-continued
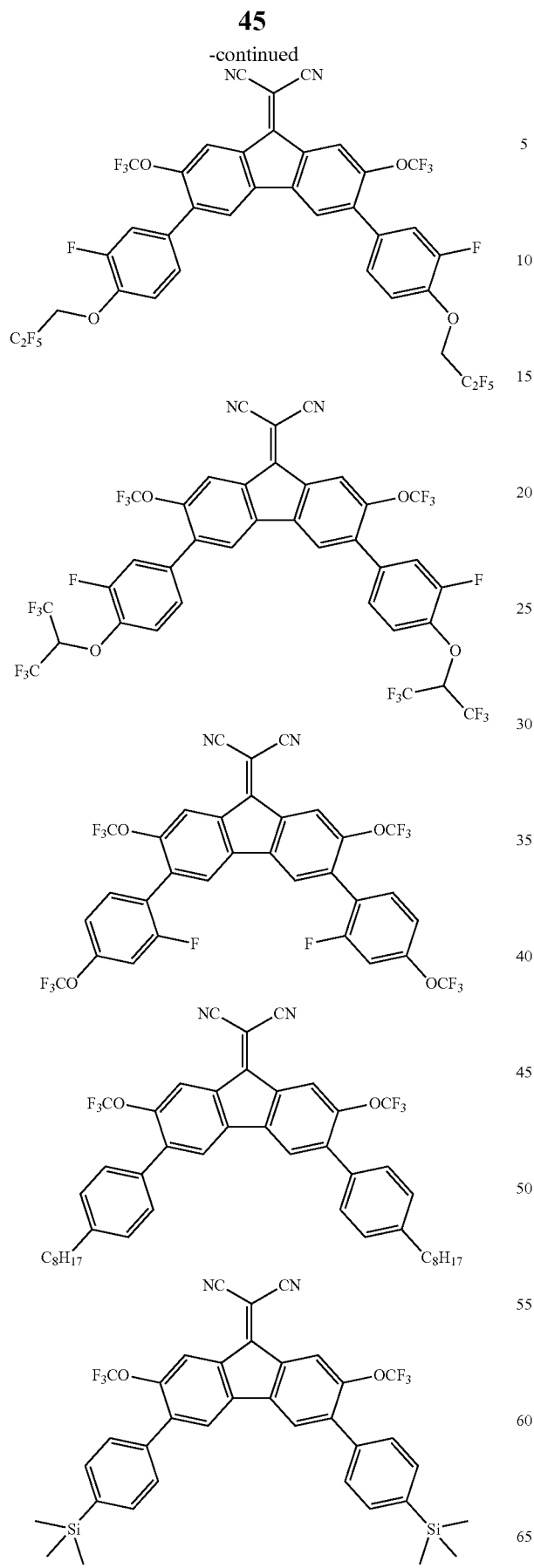
-continued
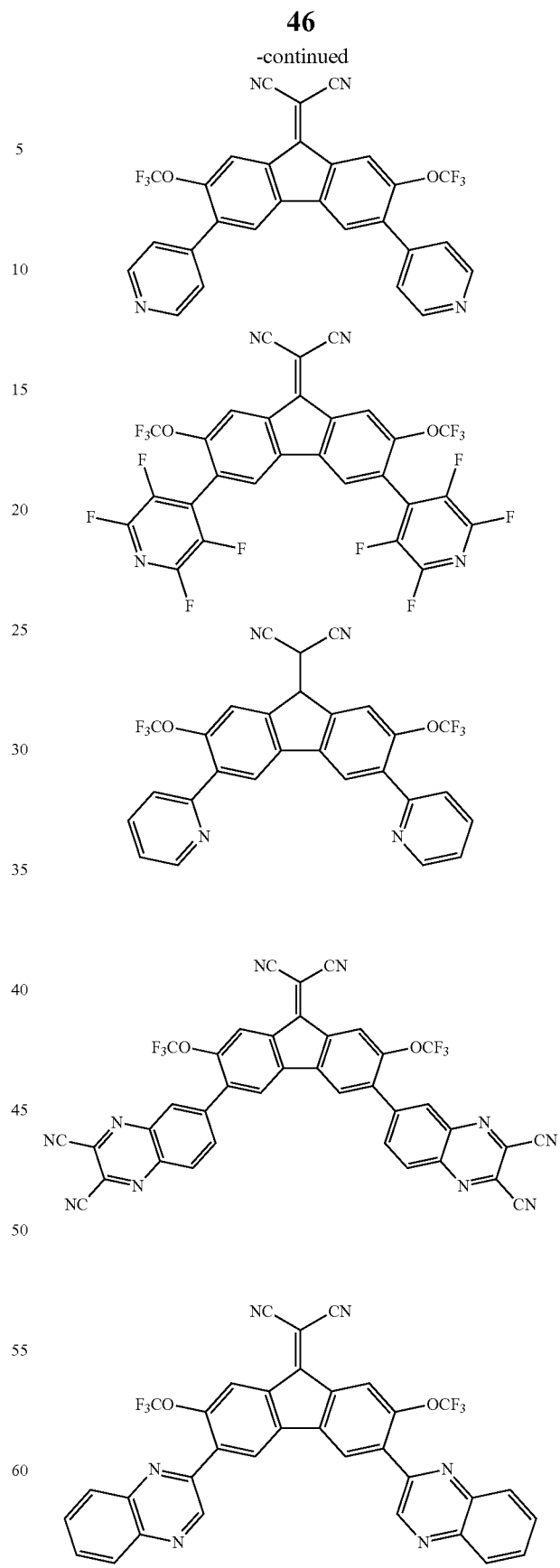

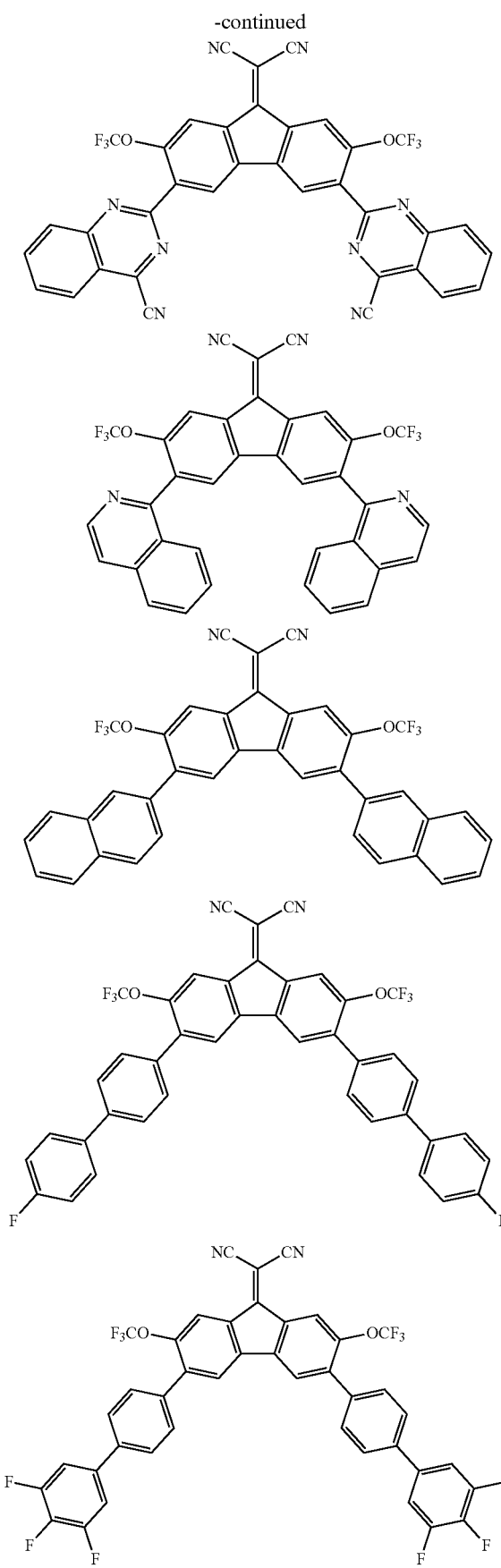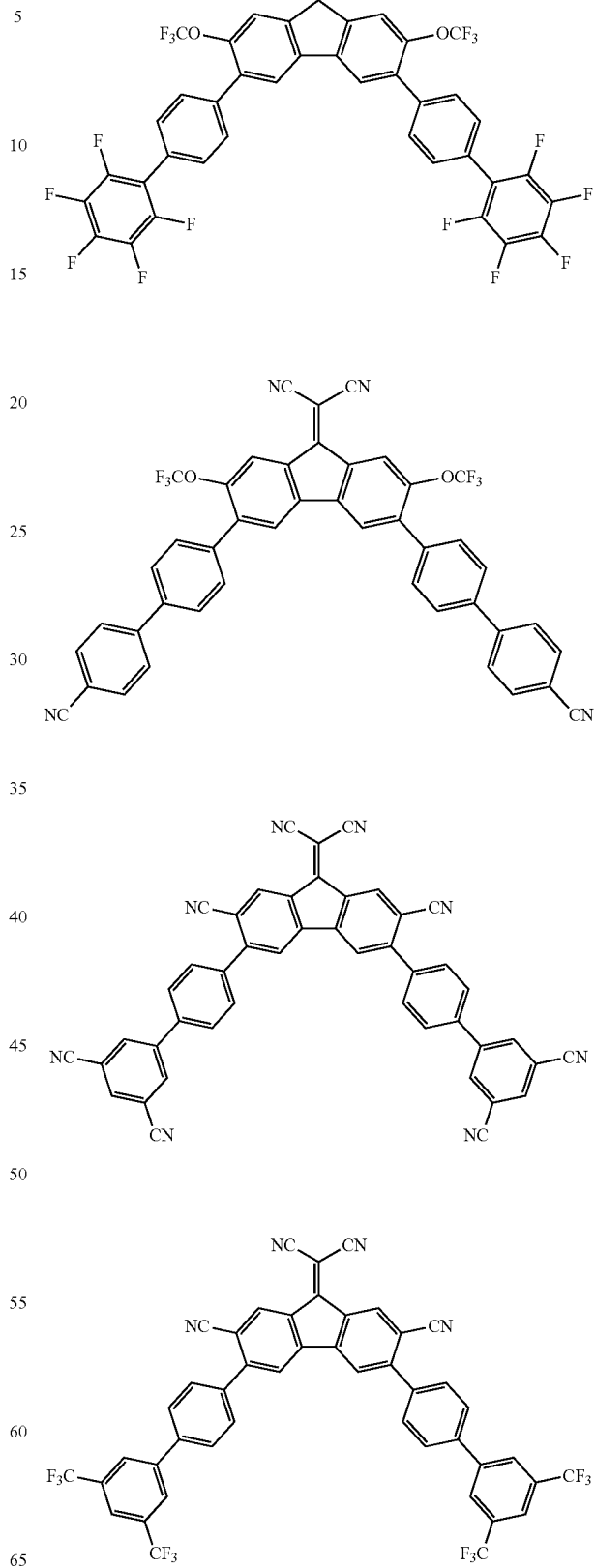

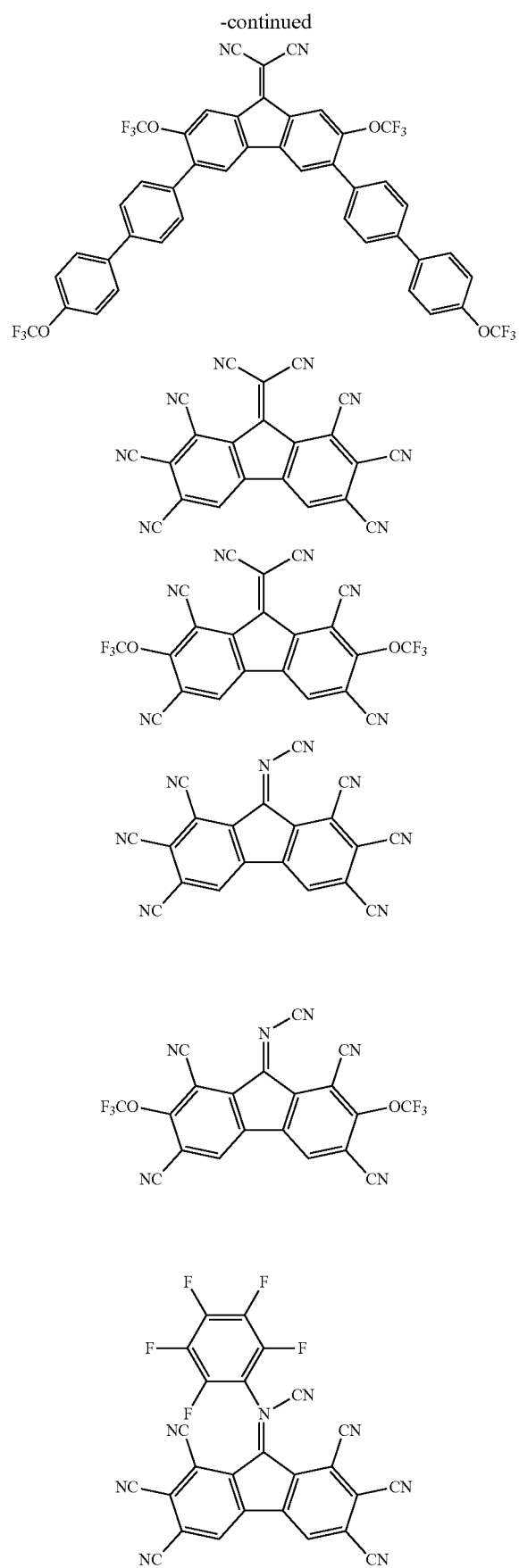
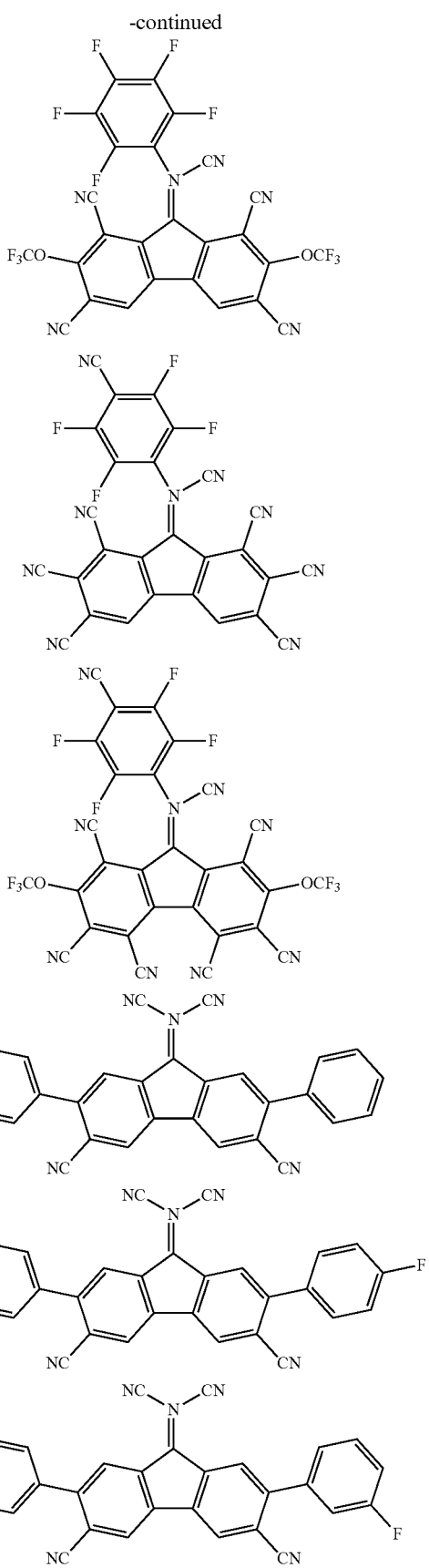

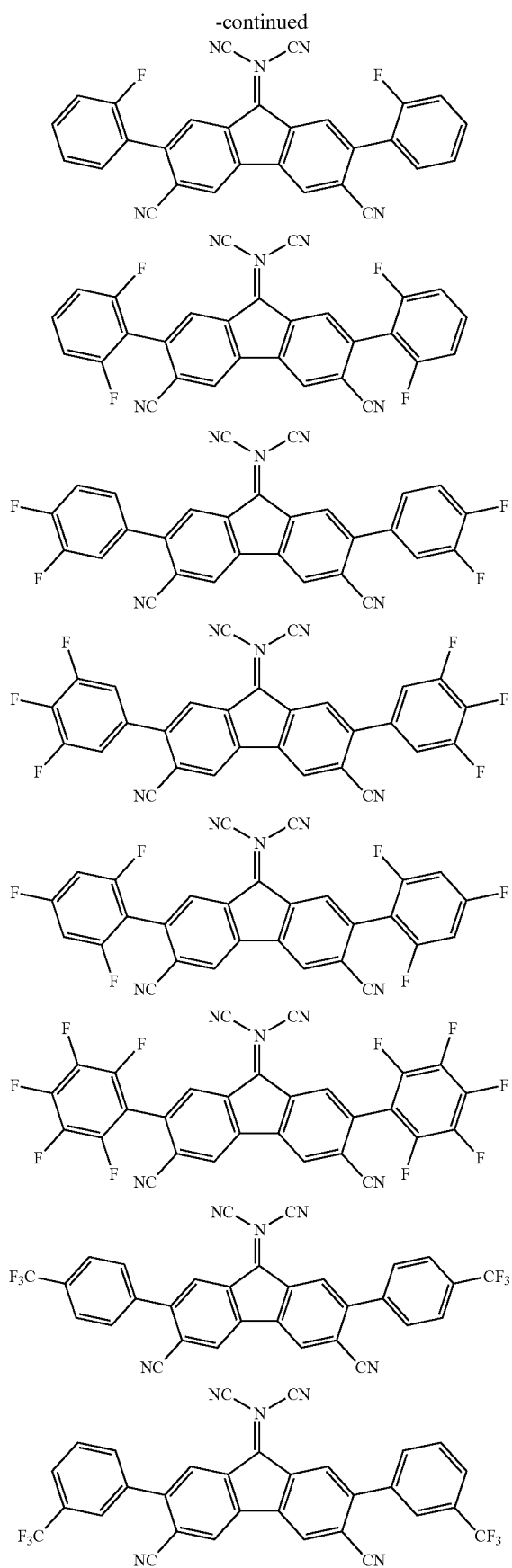
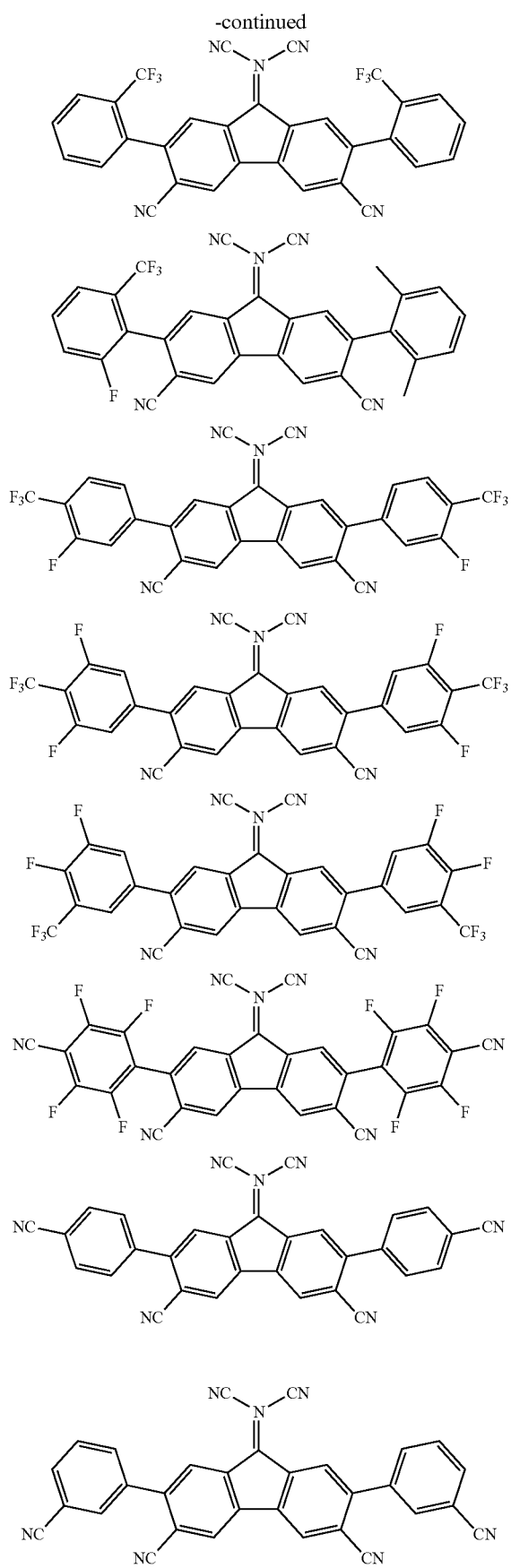

-continued
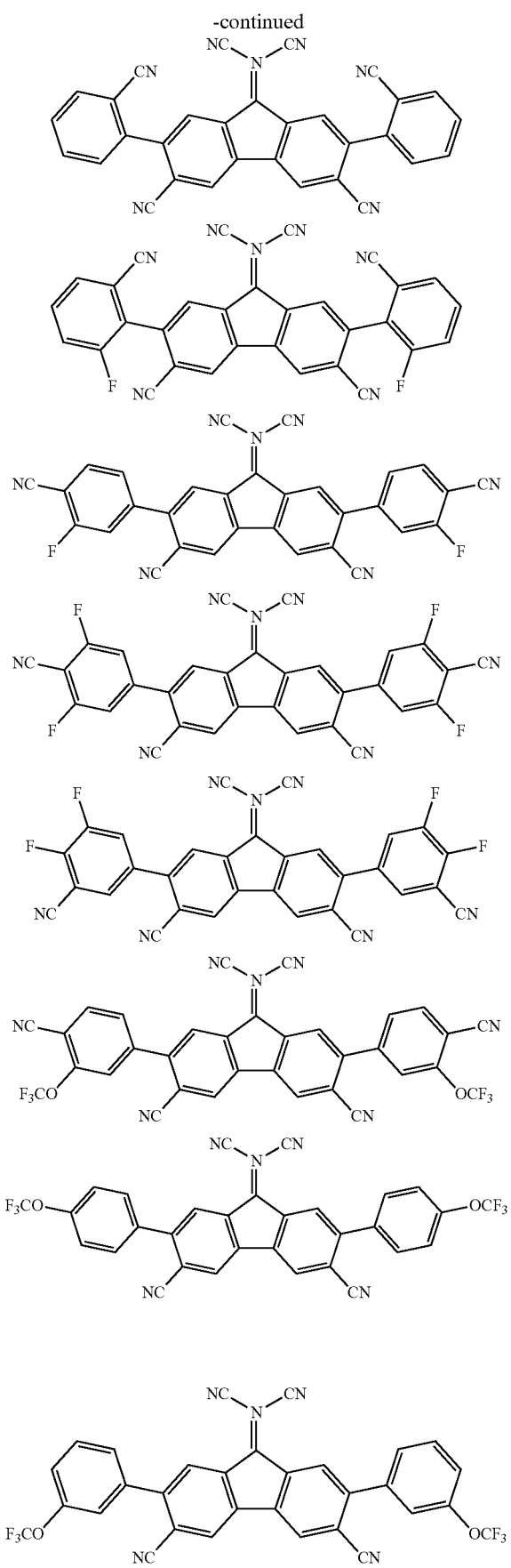
-continued
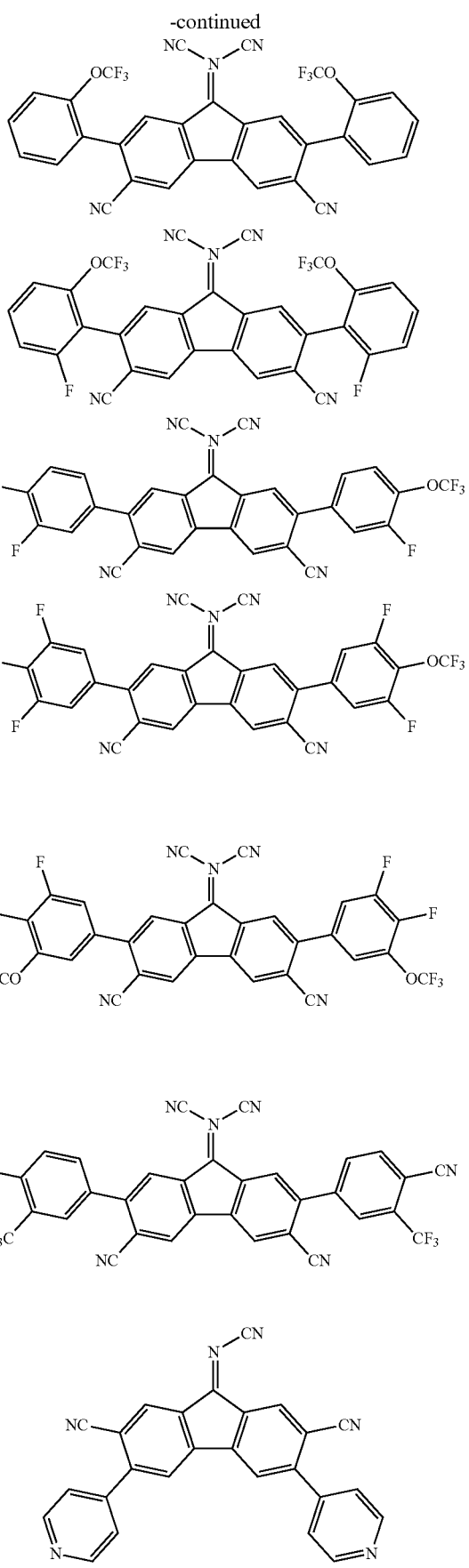

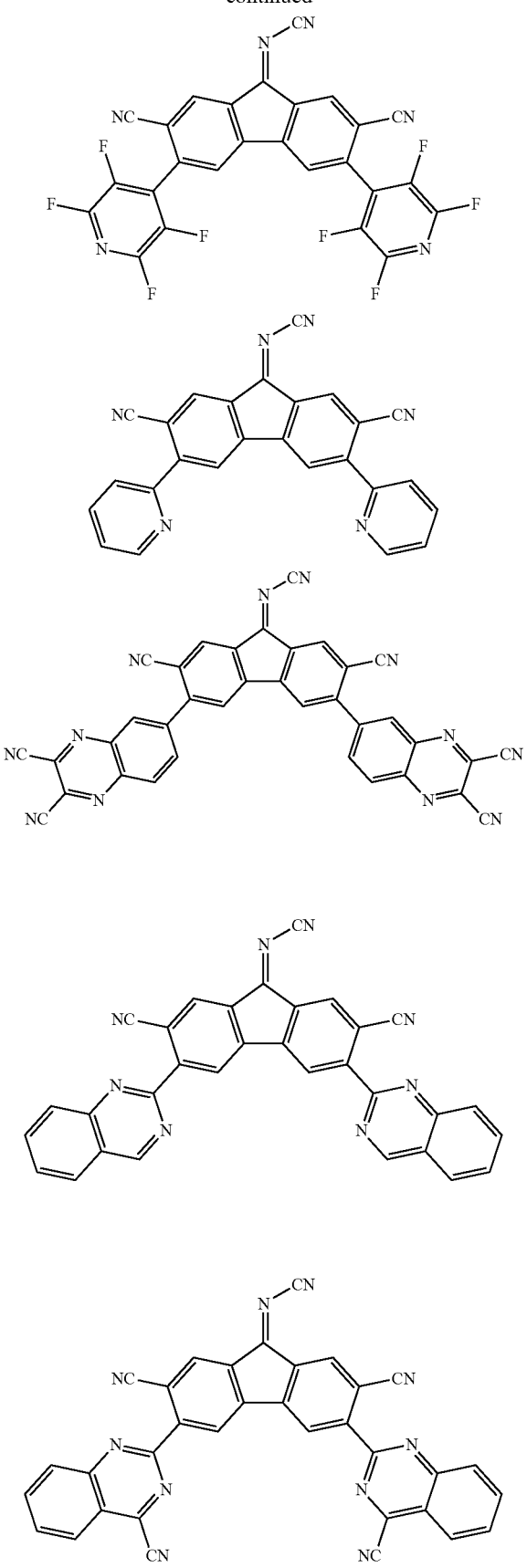
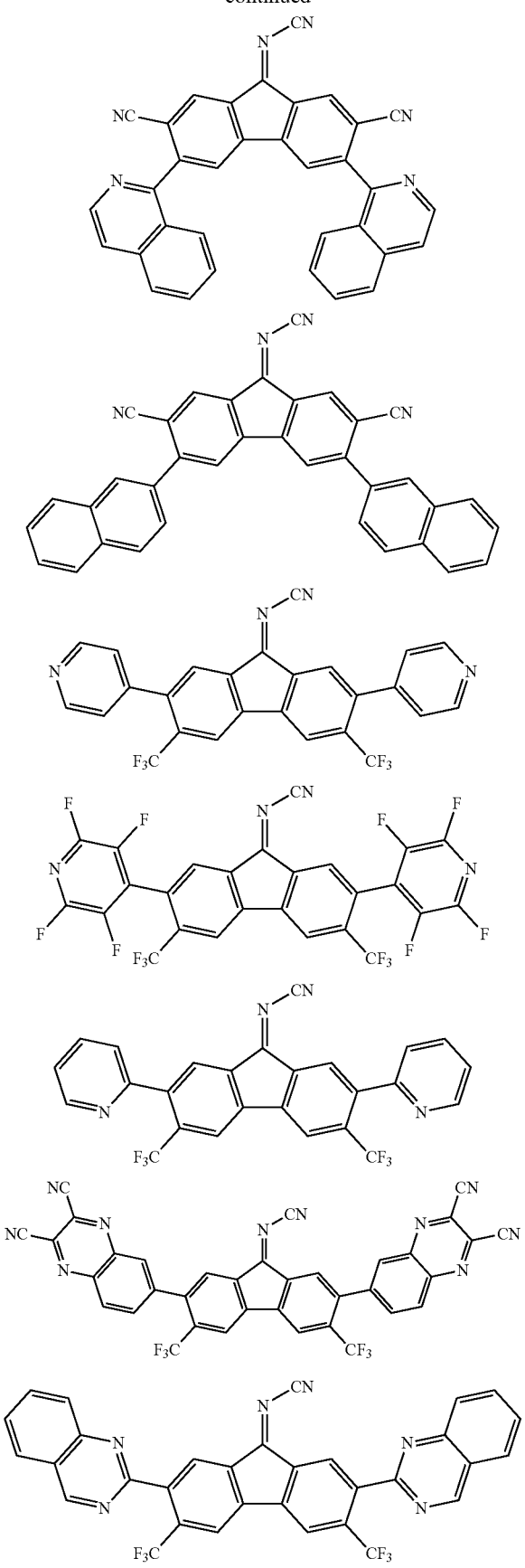

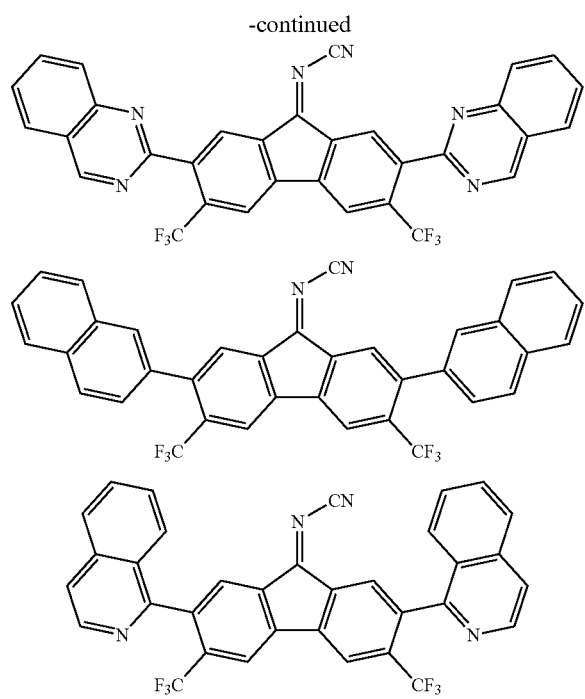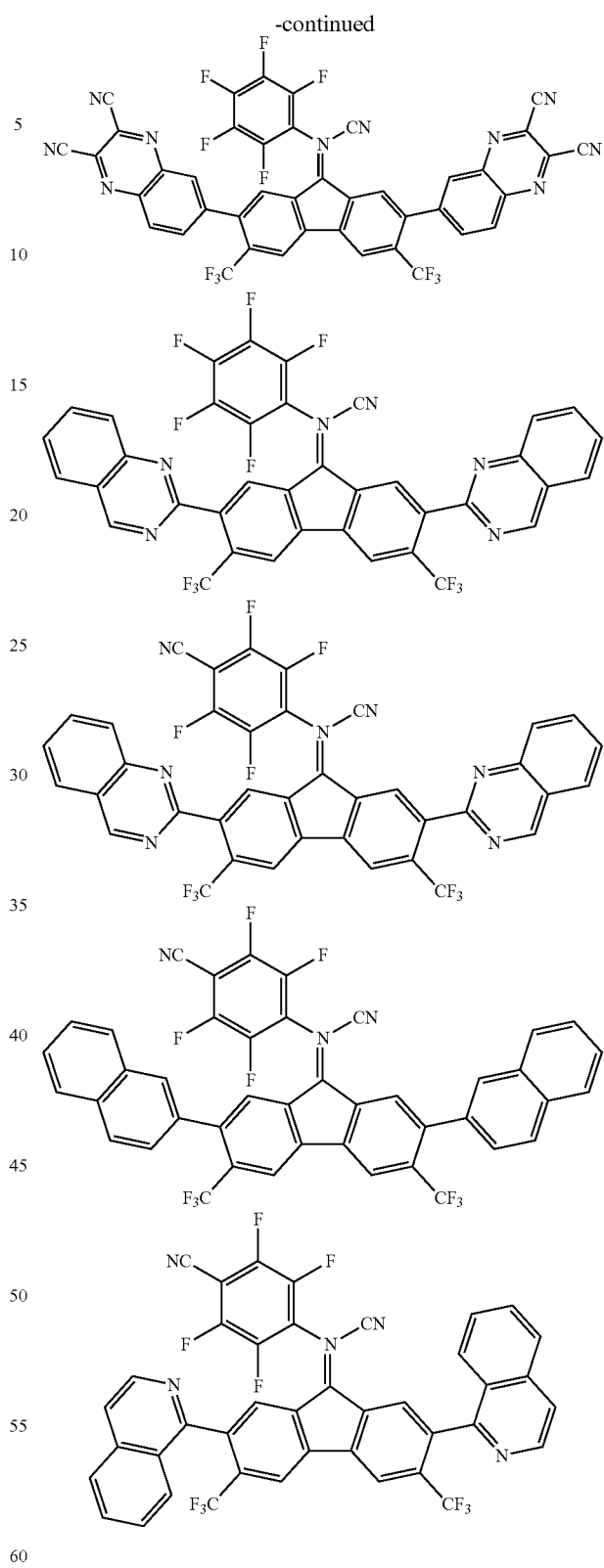
Further, the present specification provides an organic electronic device including the above-described compound.
An exemplary embodiment of the present application provides an organic electronic device including: a first electrode; a second electrode provided to face the first electrode; and one or more organic material layers provided between the first electrode and the second electrode, in which one or more layers of the organic material layers include the compound.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

The term "adjacent" in the present specification means being relatively closely disposed. In this case, the term "adjacent" may include a case of being in physical contact with each other, and may also include a case where an additional organic material layer is provided between adjacent organic material layers.

The organic material layer of the organic electronic device of the present application may also be composed of a single-layered structure, but may be composed of a multi-layered structure in which two or more organic material layers are stacked. For example, as a representative example of the organic electronic device of the present invention, an organic electronic device may have a structure including a hole injection layer, a hole transport layer, a light emitting layer, an electron transport layer, an electron injection layer, and the like as organic material layers. However, the structure of the organic electronic device is not limited thereto, and may include a fewer number of organic layers.

According to an exemplary embodiment of the present application, the organic electronic device may be selected from the group consisting of an organic light emitting device, an organic solar cell, an organic photoconductor (OPC), and an organic transistor.

In an exemplary embodiment of the present application, the organic material layer includes a hole injection layer, and the hole injection layer includes the compound of Chemical Formula 1.

In an exemplary embodiment of the present application, the organic material layer includes a hole injection layer, and the hole injection layer is formed of the compound alone or formed of the compound of Chemical Formula 1 subjected to doping.

In an exemplary embodiment of the present application, the organic material layer includes a doped hole transport layer, and the doped hole transport layer is formed of a hole transport material doped with the compound of Chemical Formula 1.

In an exemplary embodiment of the present application, the organic material layer includes a doped hole transport layer, and the doped hole transport layer is doped with a mixture obtained by mixing the compound of Chemical Formula 1 and a hole transport material.

In an exemplary embodiment of the present application, the organic material layer includes a doped hole transport layer, and the doped hole transport layer is doped with a mixture obtained by mixing the compound of Chemical Formula 1 and a hole transport material, and when a part by weight of the mixture is set to 100, a part by weight of the compound of Chemical Formula 1 is 0.1 to 50 parts by weight.

In an exemplary embodiment of the present application, a first stack which emits light of a first color and a second stack which emits light of a second color are formed between the first electrode and the second electrode, and a charge generation layer which adjust charges so as to establish a charge balance is formed between the first stack and the second stack, the charge generation layer is composed of an N-type charge generation layer disposed adjacently to the first stack and a P-type charge generation layer disposed adjacently to the second stack, and the organic material layer constitutes the P-type charge generation layer, and the P-type charge generation layer is formed of the compound of Chemical Formula 1 alone or formed of the compound of Chemical Formula 1 subjected to doping.

In an exemplary embodiment of the present application, a first stack which emits light of a first color and a second stack which emits light of a second color are formed between the first electrode and the second electrode, and a charge generation layer which adjust charges so as to establish a charge balance is formed between the first stack and the second stack, the charge generation layer is composed of an N-type charge generation layer disposed adjacently to the first stack and a P-type charge generation layer disposed adjacently to the second stack, and the organic material layer constitutes the P-type charge generation layer, and the P-type charge generation layer is formed of a hole transport material doped with the compound of Chemical Formula 1.

In an exemplary embodiment of the present application, the P-type charge generation layer is doped with a mixture obtained by mixing the compound of Chemical Formula 1 and a hole transport material.

In an exemplary embodiment of the present application, the P-type charge generation layer is doped with a mixture obtained by mixing the compound of Chemical Formula 1 and a hole transport material, and when a part by weight of the mixture is set to 100, a part by weight of the compound of Chemical Formula 1 is 0.1 to 50 parts by weight.

In an exemplary embodiment of the present application, the first stack and the second stack are each an organic material layer including a light emitting layer, and the organic material layer may further include one or more organic material layers such as a hole injection layer, a hole buffer layer, a hole transport layer, an electron blocking layer, a hole blocking layer, an electron transport layer, and an electron injection layer in addition to a light emitting layer.

In an exemplary embodiment of the present application, the organic material layer includes a hole injection layer or a hole transport layer, and the hole injection layer or the hole transport layer includes the compound.

In another exemplary embodiment, the organic material layer includes a charge generation layer, which generates charges, between the first electrode and the second electrode, and the charge generation layer includes the compound.

In an exemplary embodiment of the present application, the organic electronic device includes two or more stacks provided between a first electrode and a second electrode and including a light emitting layer, and includes a charge generation layer provided between the stacks.

In another exemplary embodiment, the organic electronic device includes a light emitting layer provided between a first electrode and a second electrode, and includes a charge generation layer provided between an electrode which serves as a negative electrode in the first electrode and the second electrode, and the light emitting layer.

In still another exemplary embodiment, the organic material layer includes two or more light emitting layers, and may include a charge generation layer including the compound of Chemical Formula 1 and provided between the two or more light emitting layers. In this case, an organic electronic device which emits a white light may be manufactured by allowing one of the light emitting layers to emit a blue color and the other to emit a yellow color. The above-described one or more organic material layers such as a hole injection layer, a hole buffer layer, a hole transport layer, an electron blocking layer, a hole blocking layer, an electron transport layer, and an electron injection layer may be further included between the light emitting layer and the positive electrode or the negative electrode or between the light emitting layer and the charge generation layer.

In an exemplary embodiment of the present application, the organic material layer includes a light emitting layer, and the light emitting layer includes the compound.

According to an exemplary embodiment of the present specification, the organic material layer includes a light emitting layer, and the light emitting layer includes a compound represented by the following Chemical Formula A-1.

[Chemical Formula A-1]

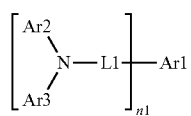

In Chemical Formula A-1, n1 is an integer of 1 or more,

Ar1 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L1 is a direct bond; a substituted or unsubstituted arylene group; or a substituted or unsubstituted heteroarylene group, Ar2 and Ar3 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may combine with each other to form a substituted or unsubstituted ring, and when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula A-1 as a dopant of the light emitting layer.

According to an exemplary embodiment of the present specification, L1 is a direct bond.

According to an exemplary embodiment of the present specification, n1 is 2.

In an exemplary embodiment of the present specification, Ar1 is a divalent pyrene group which is unsubstituted or substituted with deuterium, a methyl group, an ethyl group, or a tert-butyl group.

According to an exemplary embodiment of the present specification, Ar2 and Ar3 are the same as or different from each other, and are each independently a substituted or unsubstituted aryl group having 6 to 30 carbon atoms.

According to an exemplary embodiment of the present specification, Ar2 and Ar3 are the same as or different from each other, and are each independently an aryl group which is unsubstituted or substituted with a germanium group substituted with an alkyl group.

According to an exemplary embodiment of the present specification, Ar2 and Ar3 are the same as or different from each other, and are each independently an aryl group which is unsubstituted or substituted with a trimethylgermanium group.

According to an exemplary embodiment of the present specification, Ar2 and Ar3 are the same as or different from each other, and are each independently a substituted or unsubstituted phenyl group.

According to an exemplary embodiment of the present specification, Ar2 and Ar3 are a phenyl group which is unsubstituted or substituted with a trimethylgermanium group.

According to an exemplary embodiment of the present specification, Chemical Formula A-1 is represented by the following compound.

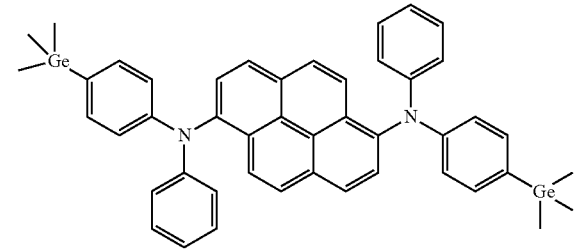

According to an exemplary embodiment of the present specification, the organic material layer includes a light emitting layer, and the light emitting layer includes a compound represented by the following Chemical Formula A-2.

[Chemical Formula A-2]

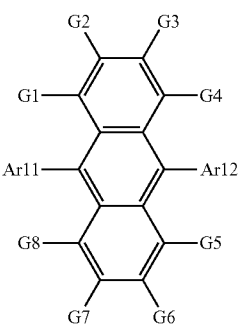

In Chemical Formula A-2,

Ar11 and Ar12 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted alkyl group; a substituted or unsubstituted monocyclic aryl group; or a substituted or unsubstituted polycyclic aryl group.

According to an exemplary embodiment of the present specification, the organic material layer includes a light emitting layer, and the light emitting layer includes the compound represented by Chemical Formula A-2 as a host of the light emitting layer.

According to an exemplary embodiment of the present specification, Ar11 and Ar12 are the same as or different from each other, and are each independently a substituted or unsubstituted polycyclic aryl group.

According to an exemplary embodiment of the present specification, Ar11 and Ar12 are the same as or different from each other, and are each independently a substituted or unsubstituted polycyclic aryl group having 10 to 30 carbon atoms.

According to an exemplary embodiment of the present specification, Ar11 and Ar12 are the same as or different from each other, and are each independently a substituted or unsubstituted phenyl group; or a substituted or unsubstituted naphthyl group.

According to an exemplary embodiment of the present specification, Ar11 and Ar12 are the same as or different from each other, and are each independently a phenyl group substituted with an aryl group; or a substituted or unsubstituted naphthyl group.

According to an exemplary embodiment of the present specification, Ar11 and Ar12 are the same as or different from each other, and are each independently a phenyl group substituted with a 2-naphthyl group; a 1-naphthyl group; or a 2-naphthyl group.

According to an exemplary embodiment of the present specification, G1 to G8 are all hydrogen.

According to an exemplary embodiment of the present specification, at least one of G1 to G8 is a substituted or unsubstituted alkyl group, and the others are hydrogen.

According to an exemplary embodiment of the present specification, at least one of G1 to G8 is an alkyl group, and the others are hydrogen.

According to an exemplary embodiment of the present specification, G1, G2, and G4 to G8 are hydrogen.

According to an exemplary embodiment of the present specification, G3 is an alkyl group.

According to an exemplary embodiment of the present specification, G3 is a methyl group, an ethyl group, a propyl group, or a butyl group.

According to an exemplary embodiment of the present specification, G3 is a methyl group, an ethyl group, a propyl group, or a butyl group.

According to an exemplary embodiment of the present specification, G3 is a methyl group.

According to an exemplary embodiment of the present specification, Chemical Formula A-2 is represented by the following compound.

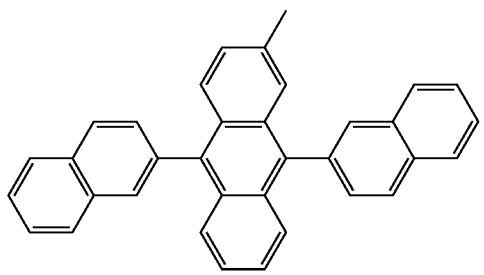

-continued

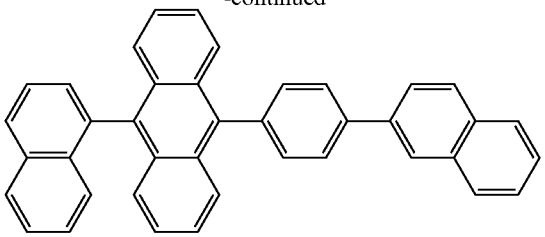

According to an exemplary embodiment of the present specification, the organic material layer includes a light emitting layer, and the light emitting layer includes the compound represented by Chemical Formula A-1 as a dopant of the light emitting layer, and includes the compound represented by Chemical Formula A-2 as a host of the light emitting layer.

In an exemplary embodiment of the present application, the organic material layer is an electron transport layer, and the organic light emitting device further includes one or two or more layers selected from the group consisting of a hole injection layer, a hole transport layer, a light emitting layer, an electron injection layer, an electron blocking layer, and a hole blocking layer.

In an exemplary embodiment of the present application, the organic electronic device includes: a first electrode; a second electrode provided to face the first electrode; a light emitting layer provided between the first electrode and the second electrode; and two or more organic material layers provided between the light emitting layer and the first electrode, or between the light emitting layer and the second electrode, in which at least one of the two or more organic material layers includes the compound. In an exemplary embodiment of the present application, as the two or more organic material layers, two or more may be selected from the group consisting of an electron transport layer, an electron injection layer, a layer which transports and injects electrons simultaneously, and a hole blocking layer.

In an exemplary embodiment of the present application, the organic material layer includes two or more electron transport layers, and at least one of the two or more electron transport layers includes the compound. Specifically, in an exemplary embodiment of the present specification, the compound may also be included in one layer of the two or more electron transport layers, and may be included in each of the two or more electron transport layers.

In addition, in an exemplary embodiment of the present application, when the compound is included in each of the two or more electron transport layers, the other materials except for the compound may be the same as or different from each other.

In an exemplary embodiment of the present application, the organic material layer further includes a hole injection layer or a hole transport layer, which includes a compound including an arylamino group, a carbazolyl group, or a benzocarbazolyl group, in addition to the organic material layer including the compound.

In another exemplary embodiment, the organic electronic device may be an organic electronic device having a structure (normal type) in which a positive electrode, one or more organic material layers, and a negative electrode are sequentially stacked on a substrate.

In still another exemplary embodiment, the organic electronic device may be an organic electronic device having a reverse direction structure (inverted type) in which a negative electrode, one or more organic material layers, and a positive electrode are sequentially stacked on a substrate.

For example, the structure of the organic electronic device according to an exemplary embodiment of the present application is exemplified in FIGS. 1 to 3.

FIG. 1 exemplifies a structure of an organic electronic device in which a substrate 1, a positive electrode 2, a light emitting layer 3, and a negative electrode 4 are sequentially stacked. In the structure as described above, the compound may be included in the light emitting layer 3.

FIG. 2 exemplifies a structure of an organic electronic device in which a substrate 1, a positive electrode 2, a hole injection layer 5, a hole transport layer 6, a light emitting layer 3, an electron transport layer 7, and a negative electrode 4 are sequentially stacked. In the structure as described above, the compound may be included in one or more layers of the hole injection layer 5, the hole transport layer 6, the light emitting layer 3, and the electron transport layer 7.

FIG. 3 exemplifies a structure of an organic electronic device including a substrate 1, a positive electrode 2, and a negative electrode 4, and including two units including hole injection layers 5a and 5b, hole transport layers 6a and 6b, light emitting layers 3a and 3b, and electron transport layers 7a and 7b between the positive electrode and the negative electrode, in which a charge generation layer 8 is provided between the units. In the structure as described above, the compound may be included in one or more layers of the hole injection layer, the hole transport layer, the light emitting layer, the electron transport layer, and the charge generation layer.

The organic electronic device of the present application may be manufactured by the materials and methods known in the art, except that one or more layers of the organic material layers include the compound of the present application, that is, the compound.

When the organic electronic device includes a plurality of organic material layers, the organic material layers may be formed of the same material or different materials.

The organic electronic device of the present application may be manufactured by the materials and methods known in the art, except that one or more layers of the organic material layers include the compound, that is, the compound represented by Chemical Formula 1.

For example, the organic electronic device of the present application may be manufactured by sequentially stacking a first electrode, an organic material layer, and a second electrode on a substrate. In this case, the organic electronic device may be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation. In addition to the method as described above, an organic electronic device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic electronic device is manufactured. Here, the solution application method means spin coating, dip coating, doctor blading, inkjet printing, screen printing, a spray method, roll coating, and the like, but is not limited thereto.

In an exemplary embodiment of the present application, the first electrode is a positive electrode, and the second electrode is a negative electrode.

In another exemplary embodiment, the first electrode is a negative electrode, and the second electrode is a positive electrode.

The organic light emitting device may have, for example, the following stacking structure, but the stacking structure is not limited thereto.

(1) Positive electrode/Hole transport layer/Light emitting layer/Negative electrode (2) Positive electrode/Hole injection layer/Hole transport layer/Light emitting layer/Negative electrode (3) Positive electrode/Hole injection layer/Hole buffer layer/Hole transport layer/Light emitting layer/Negative electrode (4) Positive electrode/Hole transport layer/Light emitting layer/Electron transport layer/Negative electrode (5) Positive electrode/Hole transport layer/Light emitting layer/Electron transport layer/Electron injection layer/Negative electrode (6) Positive electrode/Hole injection layer/Hole transport layer/Light emitting layer/Electron transport layer/Negative electrode (7) Positive electrode/Hole injection layer/Hole transport layer/Light emitting layer/Electron transport layer/Electron injection layer/Negative electrode (8) Positive electrode/Hole injection layer/Hole buffer layer/Hole transport layer/Light emitting layer/Electron transport layer/Negative electrode (9) Positive electrode/Hole injection layer/Hole buffer layer/Hole transport layer/Light emitting layer/Electron transport layer/Electron injection layer/Negative electrode

(10) Positive electrode/Hole transport layer/Electron blocking layer/Light emitting layer/Electron transport layer/Negative electrode

(11) Positive electrode/Hole transport layer/Electron blocking layer/Light emitting layer/Electron transport layer/Electron injection layer/Negative electrode

(12) Positive electrode/Hole injection layer/Hole transport layer/Electron blocking layer/Light emitting layer/Electron transport layer/Negative electrode

(13) Positive electrode/Hole injection layer/Hole transport layer/Electron blocking layer/Light emitting layer/Electron transport layer/Electron injection layer/Negative electrode

(14) Positive electrode/Hole transport layer/Light emitting layer/Hole blocking layer/Electron transport layer/Negative electrode

(15) Positive electrode/Hole transport layer/Light emitting layer/Hole blocking layer/Electron transport layer/Electron injection layer/Negative electrode

(16) Positive electrode/Hole injection layer/Hole transport layer/Light emitting layer/Hole blocking layer/Electron transport layer/Negative electrode

(17) Positive electrode/Hole injection layer/Hole transport layer/Light emitting layer/Hole blocking layer/Electron transport layer/Electron injection layer/Negative electrode As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly [3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection layer is a layer which injects holes from an electrode, and a hole injection material is preferably a compound which has a capability of transporting holes, and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and a hole transport material is suitably a material which may receive holes transported from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a Spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a compound, a dibenzofuran derivative, a ladder-type furan compound, a pyrimidine derivative, and the like, but the examples are not limited thereto.

The electron transport layer is a layer which receives electrons from an electron injection layer and transports the electrons to a light emitting layer, and an electron transport material is suitably a material which may receive electrons well from a negative electrode and transfer the electrons to a light emitting layer, and has a large mobility for electrons. Specific examples thereof include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the material to be used.

MODE FOR INVENTION

Hereinafter, the present specification will be described in detail with reference to Examples in order to specifically explain the present specification. However, the Examples according to the present specification may be modified in various forms, and it is not interpreted that the scope of the present application is limited to the Examples described in detail below. The Examples of the present application are provided for more completely explaining the present specification to the person with ordinary skill in the art.

<Preparation Example 1> Synthesis of Following Compound 1

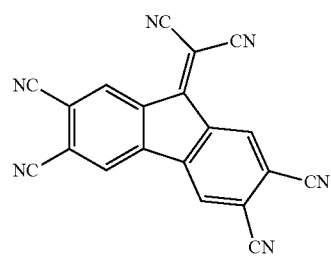 [SMILES: N#CC(C#N)=C1c2cc(C#N)c(C#N)cc2-c2cc(C#N)c(C#N)cc21]

Step 1) Synthesis of Following Compound 1-1

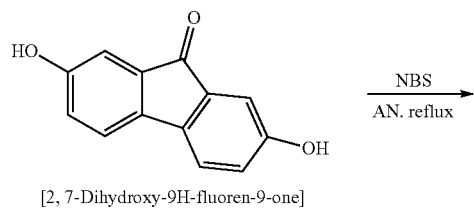

2,7-Dihydroxy-9H-fluoren-9-one (15.00 g, 70.69 mmol) and N-bromosuccinimide (37.75 g, 212.06 mmol) were completely dissolved in 200 ml of acetonitrile in a 500 ml round bottom flask, and then the resulting solution was heated and stirred for 2 hours. After the reaction was terminated, the temperature was lowered to normal temperature, and the precipitate was filtered. The obtained residue was diluted with tetrahydrofuran, and washed with water and a sodium thiosulfate aqueous solution. The organic solvent layer was collected, moisture was removed over anhydrous magnesium sulfate, and the residue was filtered and then concentrated under reduced pressure. The concentrated solution was recrystallized with a small amount of tetrahydrofuran and acetonitrile to prepare Compound 1-1 (17.00 g, yield: 65.00%).

MS[M+H]$^+$=368

Step 2) Synthesis of Following Compound 1-2

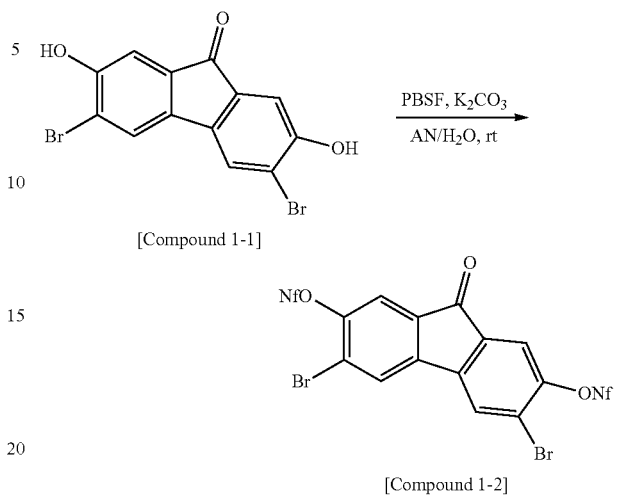

Compound 1-1 (18.40 g, 49.73 mmol) was completely dissolved in 250 ml of acetonitrile in a 1,000 ml round bottom flask at normal temperature, and then an aqueous solution (30 ml) of potassium carbonate (20.60 g) was added thereto. Perfluorosulfonyl fluoride (19.65 ml, 109.41 mmol) was added to the reaction solution, and then the resulting solution was stirred at normal temperature for 30 minutes. After the reaction was terminated, a residue obtained by concentrating the resulting product under reduced pressure was diluted with tetrahydrofuran, and washed with water and brine. The organic solvent layer was collected, moisture was removed over anhydrous magnesium sulfate, and the residue was filtered and then concentrated under reduced pressure. The concentrated solution was purified with a silica gel column chromatography (Hex:EA=50:1) to prepare Compound 1-2 (34.50 g, yield: 74.26%).

MS[M+H]$^+$=932

Step 3) Synthesis of Following Compound 1-3

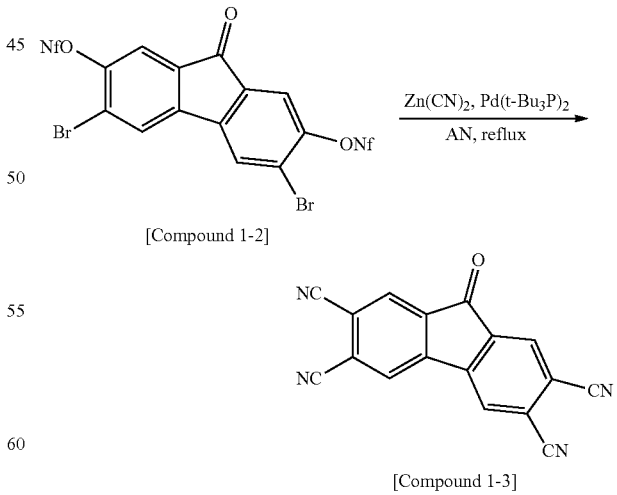

Compound 1-2 (10.00 g, 10.70 mmol) and zinc cyanide (5.03 g, 42.82 mmol) were completely dissolved in 150 ml of acetonitrile in a 500 ml round bottom flask, and then the resulting solution was heated and stirred. Bistritert-butylphosphine palladium (2.19 g, 4.28 mmol) was added to the reaction solution, and then the resulting solution was heated and stirred for 2 hours. After the reaction was terminated, the temperature was lowered to normal temperature, filtration was performed, and the organic solvent layer was collected and concentrated under reduced pressure. The concentrated solution was purified with a silica gel column chromatography (Hex:EA=4:1) to prepare Compound 1-3 (1.82 g, yield: 60.69%).

MS[M+H]$^+$=281

Step 4) Synthesis of Following Compound 1

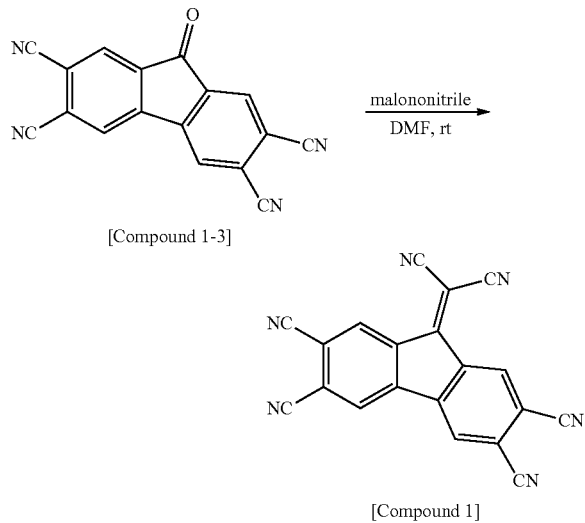

[Compound 1-3]

[Compound 1]

Compound 1-3 (3.70 g, 13.20 mmol) was completely dissolved in 50 ml of N,N-dimethylformamide in a 250 ml round bottom flask, and then the resulting solution was stirred at normal temperature. Malononitrile (1.05 g, 15.84 mmol) was added to the reaction solution, and then the resulting solution was stirred at normal temperature for 1 hour. After the reaction was terminated, water was added thereto, and a precipitate produced by stirring the resulting solution for 10 minutes was filtered. The obtained residue was diluted with ethyl acetate, moisture was removed over anhydrous magnesium sulfate, and the residue was filtered and then concentrated under reduced pressure. The concentrated solution was purified with a silica gel column chromatography (Hex:EA=3:1) to prepare Compound 1 (1.95 g, yield: 45.00%).

MS[M+H]$^+$=329

<Preparation Example 2> Synthesis of Following Compound 2

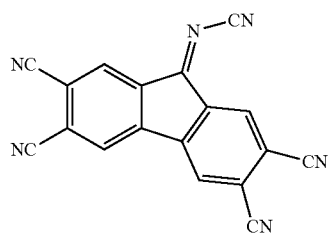 [SMILES: N#CN=C1c2cc(C#N)c(C#N)cc2-c2cc(C#N)c(C#N)cc21]

Step 1) Synthesis of Following Compound 2

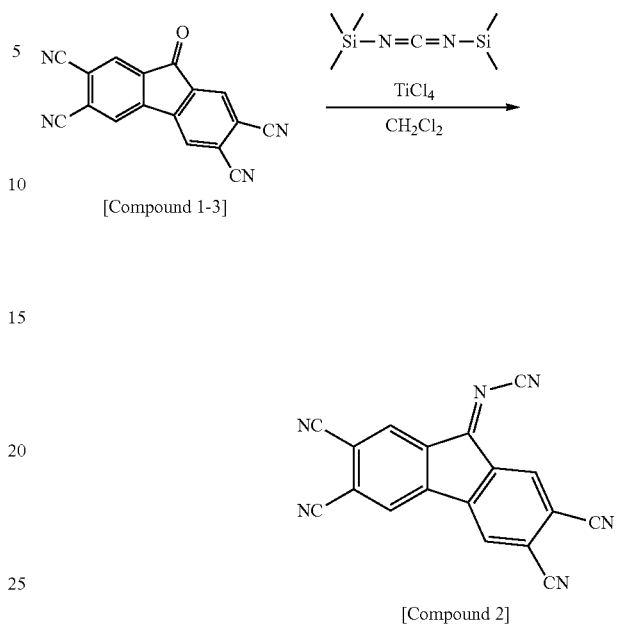

[Compound 1-3]

[Compound 2]

Compound 1-3 (2.50 g, 8.92 mmol) was completely dissolved in 30 ml of methylene chloride in a 250 ml round bottom flask, and then the resulting solution was stirred at normal temperature. Bistrimethylsilylcarbodiimide (3.33 g, 17.84 mmol) and titanium tetrachloride (5.08 g, 26.76 mmol) were added to the reaction solution, and then the resulting solution was heated and stirred for 4 hours. After the reaction was terminated, the reaction solution was diluted with methylene chloride and washed with water and brine. The organic solvent layer was collected, moisture was removed over anhydrous magnesium sulfate, and the residue was filtered and then concentrated under reduced pressure. The concentrated solution was purified with a silica gel column chromatography (Hex:EA=1:1) to prepare Compound 2 (1.41 g, yield: 51.95%).

MS[M+H]$^+$=305

<Preparation Example 3> Synthesis of Following Compound 3

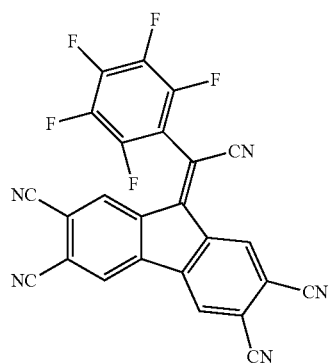 [SMILES: N#CC(=C1c2cc(C#N)c(C#N)cc2-c2cc(C#N)c(C#N)cc21)c1c(F)c(F)c(F)c(F)c1F]

Step 1) Synthesis of Following Compound 3

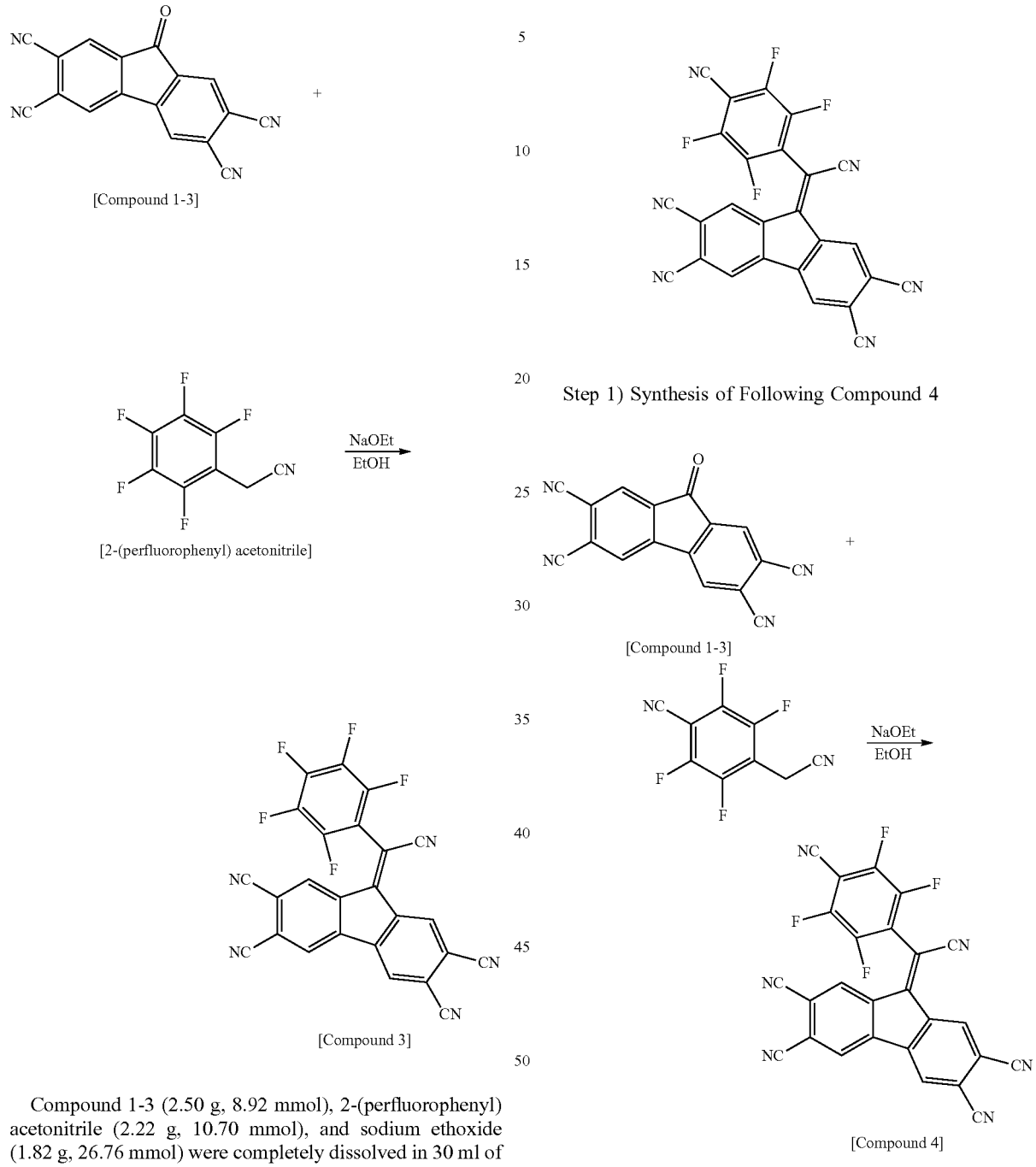

Compound 1-3 (2.50 g, 8.92 mmol), 2-(perfluorophenyl) acetonitrile (2.22 g, 10.70 mmol), and sodium ethoxide (1.82 g, 26.76 mmol) were completely dissolved in 30 ml of ethanol in a 250 ml round bottom flask, and then the resulting solution was heated and stirred. After the reaction was terminated, a residue obtained by concentrating the resulting product under reduced pressure was diluted with tetrahydrofuran, and washed with water and brine. The organic solvent layer was collected, moisture was removed over anhydrous magnesium sulfate, and the residue was filtered and then concentrated under reduced pressure. The concentrated solution was purified with a silica gel column chromatography (Hex:EA=1:1) to prepare Compound 3 (2.20 g, yield: 52.55%).

MS[M+H]$^+$=470

<Preparation Example 4> Synthesis of Following Compound 4

Step 1) Synthesis of Following Compound 4

4-(Cyanomethyl)-2,3,5,6-tetrafluorobenzonitrile

Compound 1-3 (2.50 g, 8.92 mmol), 4-(cyanomethyl)-2, 3,5,6-tetrafluorobenzonitrile (2.29 g, 10.70 mmol), and sodium ethoxide (1.82 g, 26.76 mmol) were completely dissolved in 30 ml of ethanol in a 250 ml round bottom flask, and then the resulting solution was heated and stirred. After the reaction was terminated, a residue obtained by concentrating the resulting product under reduced pressure was diluted with tetrahydrofuran, and washed with water and brine. The organic solvent layer was collected, moisture was removed over anhydrous magnesium sulfate, and the residue was filtered and then concentrated under reduced pressure. The concentrated solution was purified with a silica gel column chromatography (Hex:EA=1:1) to prepare Compound 4 (2.06 g, yield: 48.48%).

MS[M+H]$^+$=477

<Preparation Example 5> Synthesis of Following Compound 5

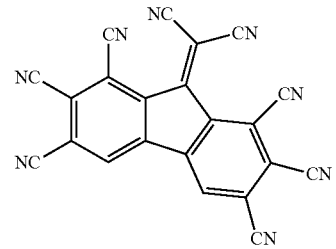 [SMILES: N#CC(C#N)=C1c2c(cc(C#N)c(C#N)c2C#N)-c2cc(C#N)c(C#N)c(C#N)c21]

Step 1) Synthesis of Following Compound 5-1

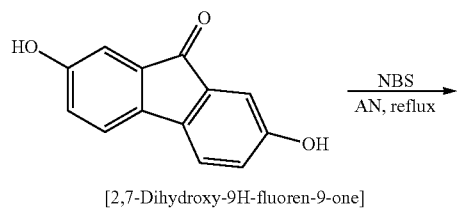

[2,7-Dihydroxy-9H-fluoren-9-one]

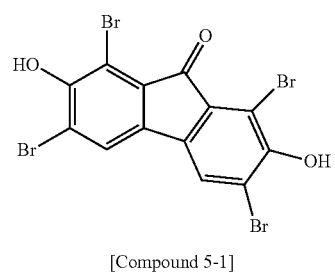

[Compound 5-1]

2,7-Dihydroxy-9H-fluoren-9-one (15.00 g, 70.69 mmol) and N-bromosuccinimide (75.49 g, 424.13 mmol) were completely dissolved in 200 ml of acetonitrile in a 500 ml round bottom flask, and then the resulting solution was heated and stirred for 2 hours. After the reaction was terminated, the temperature was lowered to normal temperature, and the precipitate was filtered. The obtained residue was diluted with tetrahydrofuran, and washed with water and a sodium thiosulfate aqueous solution. The organic solvent layer was collected, moisture was removed over anhydrous magnesium sulfate, and the residue was filtered and then concentrated under reduced pressure. The concentrated solution was purified with a silica gel column chromatography (Hex:EA=1:1) to prepare Compound 5-1 (11.20 g, yield: 30.02%).

MS[M+H]$^+$=524

Step 2) Synthesis of Following Compound 5-2

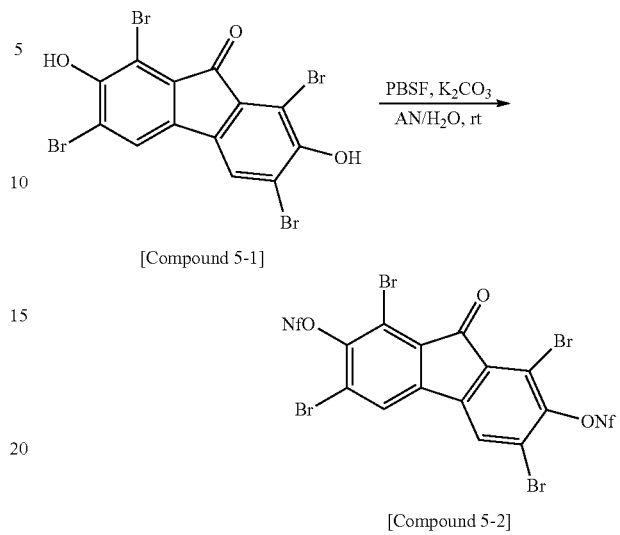

Compound 5-1 (11.20 g, 21.22 mmol) was completely dissolved in 150 ml of acetonitrile in a 500 ml round bottom flask at normal temperature, and then an aqueous solution (20 ml) of potassium carbonate (8.80 g) was added thereto. Perfluorosulfonyl fluoride (8.38 ml, 46.69 mmol) was added to the reaction solution, and then the resulting solution was stirred at normal temperature for 30 minutes. After the reaction was terminated, a residue obtained by concentrating the resulting product under reduced pressure was diluted with tetrahydrofuran, and washed with water and brine. The organic solvent layer was collected, moisture was removed over anhydrous magnesium sulfate, and the residue was filtered and then concentrated under reduced pressure. The concentrated solution was purified with a silica gel column chromatography (Hex:EA=50:1) to prepare Compound 5-2 (15.99 g, yield: 69.01%).

MS[M+H]$^+$=1088

Step 3) Synthesis of Following Compound 5-3

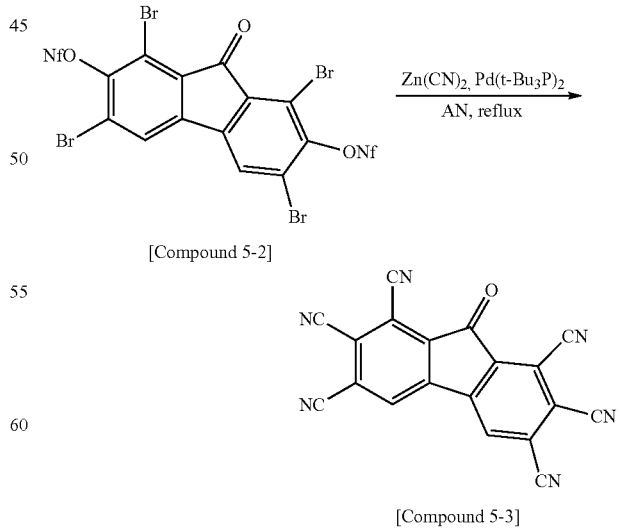

Compound 5-2 (15.99 g, 14.64 mmol) and zinc cyanide (6.88 g, 58.57 mmol) were completely dissolved in 200 ml of acetonitrile in a 500 ml round bottom flask, and then the resulting solution was heated and stirred. Bistritert-butylphosphine palladium (2.99 g, 5.86 mmol) was added to the reaction solution, and then the resulting solution was heated and stirred for 2 hours. After the reaction was terminated, the temperature was lowered to normal temperature, filtration was performed, and the organic solvent layer was collected and concentrated under reduced pressure. The concentrated solution was purified with a silica gel column chromatography (Hex:EA=4:1) to prepare Compound 5-3 (2.51 g, yield: 51.91%).

MS[M+H]$^+$=331

Step 4) Synthesis of Following Compound 5

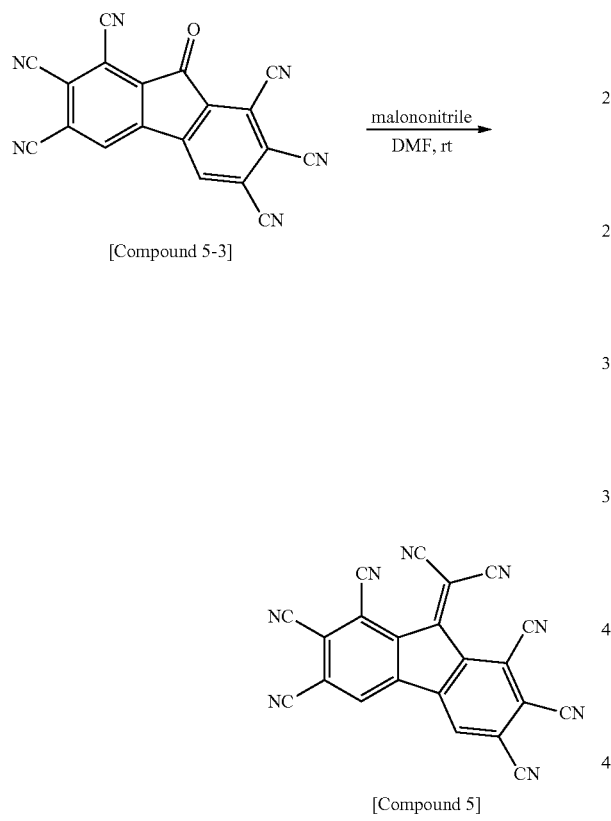

[Compound 5-3]

[Compound 5]

Compound 5-3 (2.50 g, 7.57 mmol) was completely dissolved in 20 ml of N,N-dimethylformamide in a 250 ml round bottom flask, and then the resulting solution was stirred at normal temperature. Malononitrile (0.60 g, 9.08 mmol) was added to the reaction solution, and then the resulting solution was stirred at normal temperature for 1 hour. After the reaction was terminated, water was added thereto, and a precipitate produced by stirring the resulting solution for 10 minutes was filtered. The obtained residue was diluted with ethyl acetate, moisture was removed over anhydrous magnesium sulfate, and the residue was filtered and then concentrated under reduced pressure. The concentrated solution was purified with a silica gel column chromatography (Hex:EA=3:1) to prepare Compound 5 (1.14 g, yield: 39.81%).

MS[M+H]$^+$=379

<Preparation Example 6> Synthesis of Following Compound 6

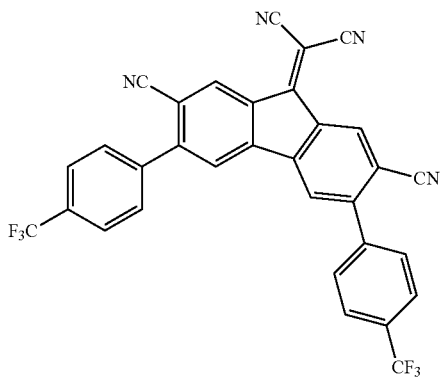 [SMILES: N#CC(C#N)=C1c2cc(C#N)c(-c3ccc(C(F)(F)F)cc3)cc2-c2cc(-c3ccc(C(F)(F)F)cc3)c(C#N)cc21]

Step 1) Synthesis of Following Compound 6-1

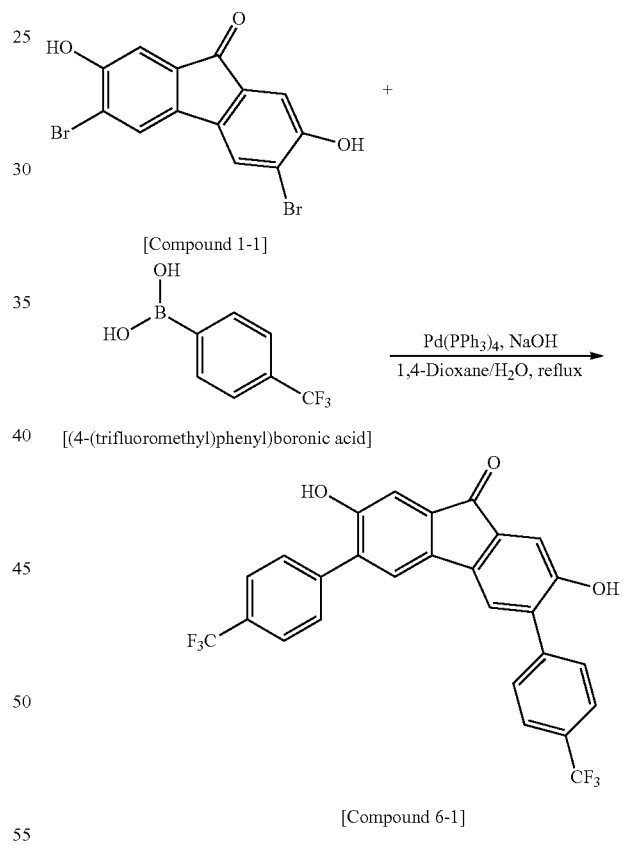

[Compound 1-1]

[(4-(trifluoromethyl)phenyl)boronic acid]

[Compound 6-1]

Compound 1-1 (10.00 g, 27.03 mmol) and (4-(trifluoromethyl)phenyl)boronic acid (12.32 g, 64.87 mmol) were completely dissolved in 80 ml of 1,4-dioxane in a 500 ml round bottom flask, and then an aqueous solution (30 ml) of sodium hydroxide (3.24 g, 81.09 mmol) was added thereto, and the resulting solution was heated and stirred. Tetrakis-triphenylphosphine palladium (0.94 g, 0.81 mmol) was added to the reaction solution, and then the resulting solution was heated and stirred for 18 hours. After the reaction was terminated, a residue obtained by concentrating the resulting product under reduced pressure was diluted with tetrahydrofuran, and washed with water and brine. The organic solvent layer was collected, moisture was removed over anhydrous magnesium sulfate, and the residue was filtered and then concentrated under reduced pressure. The concentrated solution was purified with a silica gel column chromatography (Hex:EA=1:1) to prepare Compound 6-1 (9.36 g, yield: 69.20%).

MS[M+H]⁺=501

Step 2) Synthesis of Following Compound 6-2

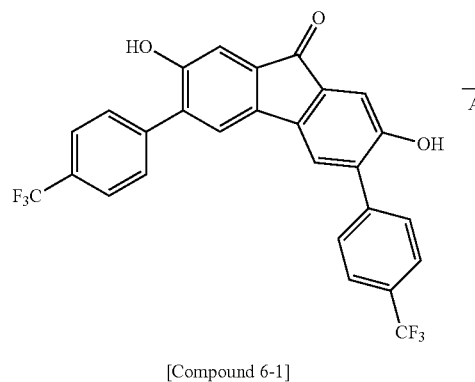
[Compound 6-1]

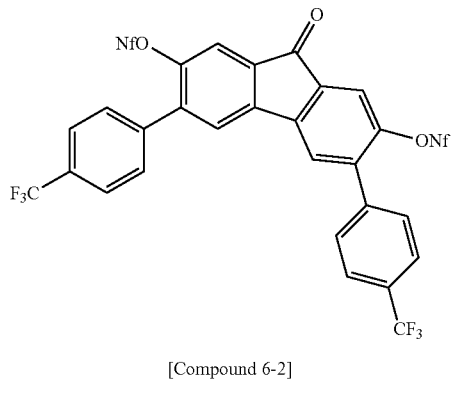
[Compound 6-2]

Compound 6-1 (10.00 g, 19.98 mmol) was completely dissolved in 100 ml of acetonitrile in a 500 ml round bottom flask at normal temperature, and then an aqueous solution (20 ml) of potassium carbonate (8.28 g, 59.94 mmol) was added thereto. Perfluorosulfonyl fluoride (7.90 ml, 43.97 mmol) was added to the reaction solution, and then the resulting solution was stirred at normal temperature for 30 minutes. After the reaction was terminated, a residue obtained by concentrating the resulting product under reduced pressure was diluted with tetrahydrofuran, and washed with water and brine. The organic solvent layer was collected, moisture was removed over anhydrous magnesium sulfate, and the residue was filtered and then concentrated under reduced pressure. The concentrated solution was purified with a silica gel column chromatography (Hex:EA=40:1) to prepare Compound 6-2 (12.20 g, yield: 57.36%).

MS[M+H]⁺=1064

Step 3) Synthesis of Following Compound 6-3

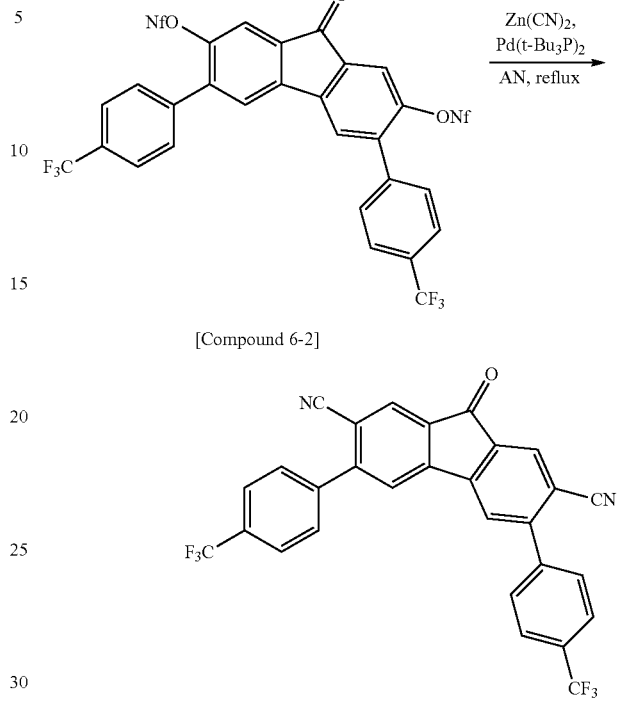
[Compound 6-2]

[Compound 6-3]

Compound 6-2 (10.00 g, 9.39 mmol) and zinc cyanide (4.41 g, 37.57 mmol) were completely dissolved in 150 ml of acetonitrile in a 500 ml round bottom flask, and then the resulting solution was heated and stirred. Bistritert-butylphosphine palladium (1.92 g, 3.76 mmol) was added to the reaction solution, and then the resulting solution was heated and stirred for 2 hours. After the reaction was terminated, the temperature was lowered to normal temperature, filtration was performed, and the organic solvent layer was collected and concentrated under reduced pressure. The concentrated solution was purified with a silica gel column chromatography (Hex:EA=4:1) to prepare Compound 6-3 (2.84 g, yield: 58.34%).

MS[M+H]⁺=519

Step 4) Synthesis of Following Compound 6

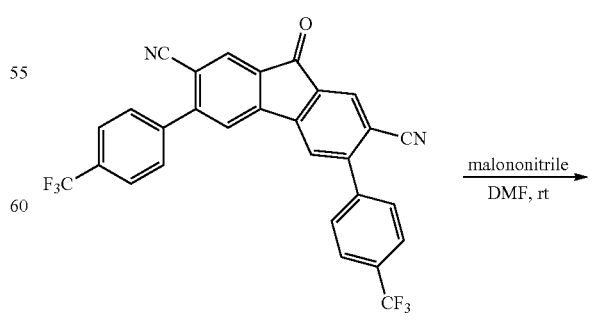
[Compound 6-3]

-continued

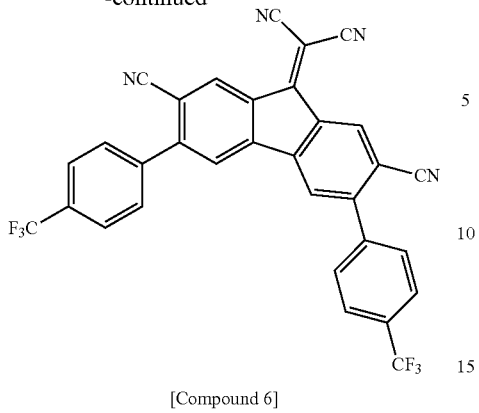

[Compound 6]

Compound 6-3 (2.50 g, 4.82 mmol) was completely dissolved in 15 ml of N,N-dimethylformamide in a 100 ml round bottom flask, and then the resulting solution was stirred at normal temperature. Malononitrile (0.38 g, 5.79 mmol) was added to the reaction solution, and then the resulting solution was stirred at normal temperature for 1 hour. After the reaction was terminated, water was added thereto, and a precipitate produced by stirring the resulting solution for 10 minutes was filtered. The obtained residue was diluted with ethyl acetate, moisture was removed over anhydrous magnesium sulfate, and the residue was filtered and then concentrated under reduced pressure. The concentrated solution was purified with a silica gel column chromatography (Hex:EA=3:1) to prepare Compound 6 (1.22 g, yield: 44.68%).

MS[M+H]$^+$=567

<Preparation Example 7> Synthesis of Following Compound 7

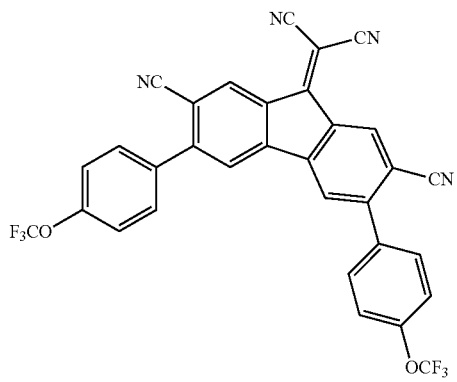

Step 1) Synthesis of Following Compound 7-1

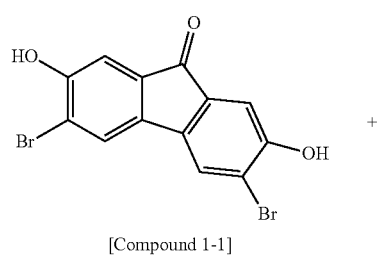

[Compound 1-1]

+

-continued

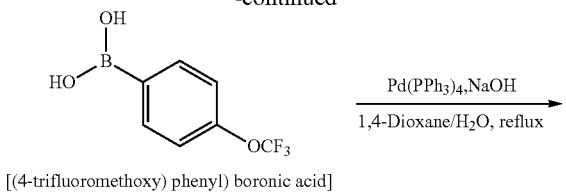

[(4-trifluoromethoxy) phenyl) boronic acid]

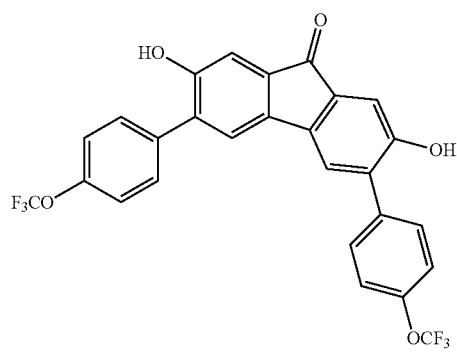

[Compound 7-1]

Compound 1-1 (10.00 g, 27.03 mmol) and (4-(trifluoromethoxy)phenyl)boronic acid (13.36 g, 64.87 mmol) were completely dissolved in 80 ml of 1,4-dioxane in a 500 ml round bottom flask, and then an aqueous solution (30 ml) of sodium hydroxide (3.24 g, 81.09 mmol) was added thereto, and the resulting solution was heated and stirred. Tetrakis-triphenylphosphine palladium (0.94 g, 0.81 mmol) was added to the reaction solution, and then the resulting solution was heated and stirred for 18 hours. After the reaction was terminated, a residue obtained by concentrating the resulting product under reduced pressure was diluted with tetrahydrofuran, and washed with water and brine. The organic solvent layer was collected, moisture was removed over anhydrous magnesium sulfate, and the residue was filtered and then concentrated under reduced pressure. The concentrated solution was purified with a silica gel column chromatography (Hex:EA=1:1) to prepare Compound 7-1 (10.05 g, yield: 69.84%).

MS[M+H]$^+$=533

Step 2) Synthesis of Following Compound 7-2

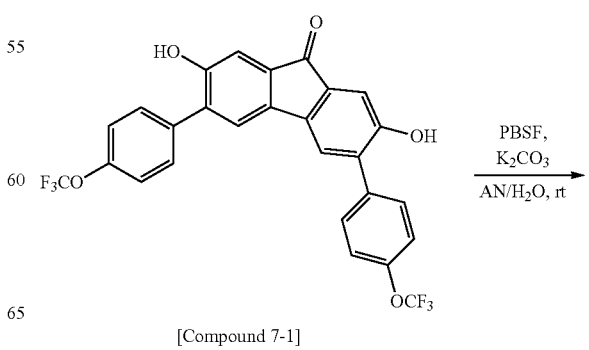

[Compound 7-1]

-continued

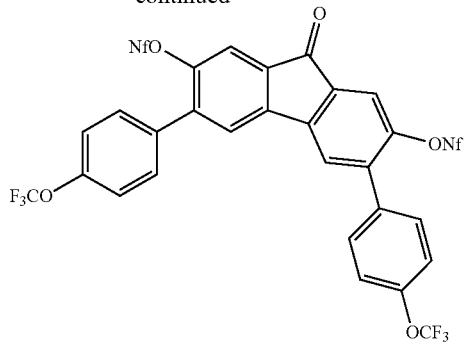

[Compound 7-2]

Compound 7-1 (10.00 g, 18.78 mmol) was completely dissolved in 100 ml of acetonitrile in a 500 ml round bottom flask at normal temperature, and then an aqueous solution (20 ml) of potassium carbonate (7.79 g, 56.34 mmol) was added thereto. Perfluorosulfonyl fluoride (7.42 ml, 41.32 mmol) was added to the reaction solution, and then the resulting solution was stirred at normal temperature for 30 minutes. After the reaction was terminated, a residue obtained by concentrating the resulting product under reduced pressure was diluted with tetrahydrofuran, and washed with water and brine. The organic solvent layer was collected, moisture was removed over anhydrous magnesium sulfate, and the residue was filtered and then concentrated under reduced pressure. The concentrated solution was purified with a silica gel column chromatography (Hex:EA=40:1) to prepare Compound 7-2 (13.20 g, yield: 64.13%).

MS[M+H]$^+$=1096

Step 3) Synthesis of Following Compound 7-3

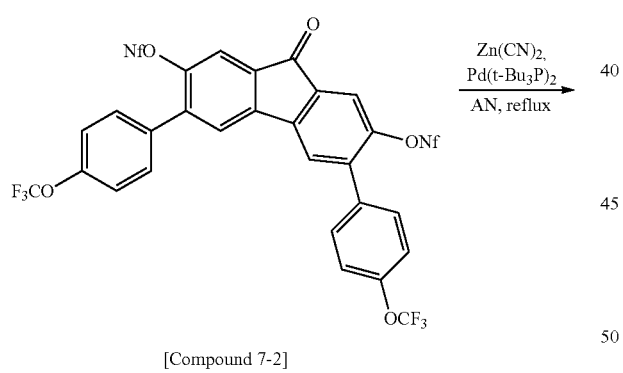

Compound 7-2 (10.00 g, 9.12 mmol) and zinc cyanide (4.29 g, 36.50 mmol) were completely dissolved in 150 ml of acetonitrile in a 500 ml round bottom flask, and then the resulting solution was heated and stirred. Bistritert-butylphosphine palladium (1.86 g, 3.65 mmol) was added to the reaction solution, and then the resulting solution was heated and stirred for 2 hours. After the reaction was terminated, the temperature was lowered to normal temperature, filtration was performed, and the organic solvent layer was collected and concentrated under reduced pressure. The concentrated solution was purified with a silica gel column chromatography (Hex:EA=4:1) to prepare Compound 7-3 (2.76 g, yield: 54.98%).

MS[M+H]$^+$=551

Step 4) Synthesis of Following Compound 7

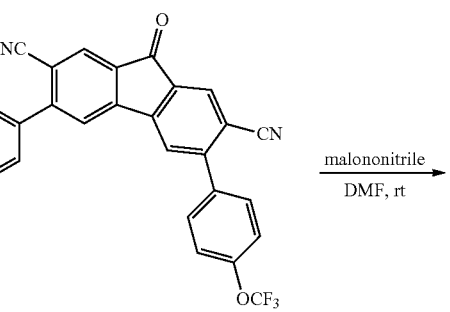

[Compound 7-3]

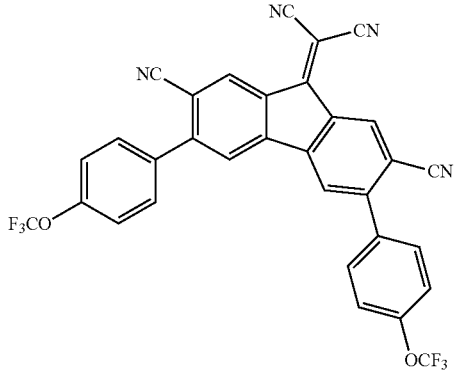 [SMILES: N#CC(C#N)=C1c2cc(C#N)c(-c3ccc(OC(F)(F)F)cc3)cc2-c2cc(-c3ccc(OC(F)(F)F)cc3)c(C#N)cc21]

[Compound 7]

Compound 7-3 (2.50 g, 4.54 mmol) was completely dissolved in 15 ml of N,N-dimethylformamide in a 100 ml round bottom flask, and then the resulting solution was stirred at normal temperature. Malononitrile (0.36 g, 5.45 mmol) was added to the reaction solution, and then the resulting solution was stirred at normal temperature for 1 hour. After the reaction was terminated, water was added thereto, and a precipitate produced by stirring the resulting solution for 10 minutes was filtered. The obtained residue was diluted with ethyl acetate, moisture was removed over anhydrous magnesium sulfate, and the residue was filtered and then concentrated under reduced pressure. The concentrated solution was purified with a silica gel column chromatography (Hex:EA=3:1) to prepare Compound 7 (1.35 g, yield: 49.69%).

MS[M+H]$^+$=599

DEVICE APPLICATION EXAMPLES

Experimental Example 1-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator. NPB of the following Chemical Formula was formed to have a thickness of 100 Å on the transparent ITO electrode, which was thus prepared, in which the resulting electrode was doped with Compound 1 at a doping concentration of 25 wt %, and NPB was subsequently formed to have a thickness of 600 Å as a hole transport layer.

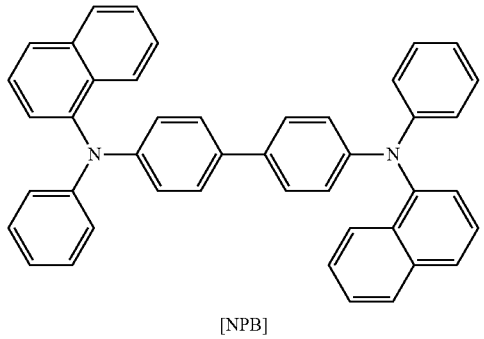

[NPB]

Subsequently, MADN of the following Chemical Formula as a host and ED of the following Chemical Formula as a dopant were vacuum deposited so as to have a weight ratio of 40:2 on the hole transport layer, thereby forming a light emitting layer.

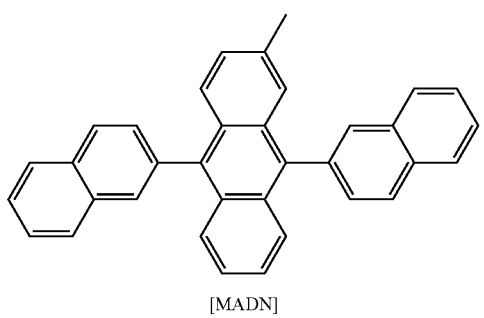

[MADN]

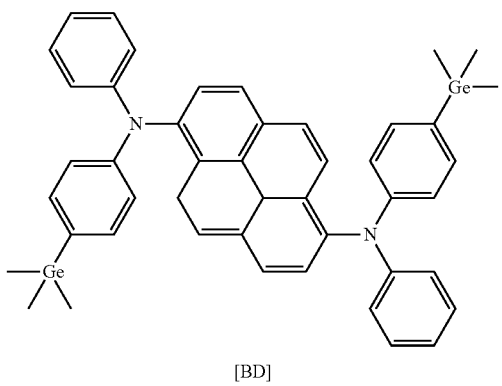

[BD]

Subsequently, Alq$_3$ of the following Chemical Formula was vacuum deposited to have a thickness of 300 Å on the light emitting layer, thereby forming an electron transport layer.

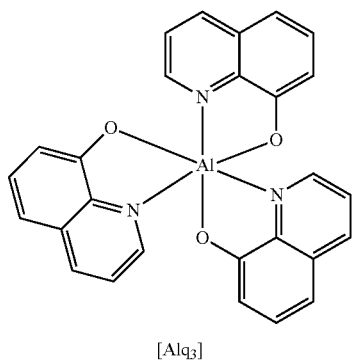

[Alq$_3$]

Lithium fluoride (LiF) and aluminum were sequentially deposited to have a thickness of 10 Å and 800 Å, respectively, on the electron transport layer, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic electronic device.

Experimental Example 1-2

An organic electronic device was manufactured in the same manner as in Experimental Example 1-1, except that Compound 2 was used instead of Compound 1 in Experimental Example 1-1.

Experimental Example 1-3

An organic electronic device was manufactured in the same manner as in Experimental Example 1-1, except that Compound 3 was used instead of Compound 1 in Experimental Example 1-1.

Experimental Example 1-4

An organic electronic device was manufactured in the same manner as in Experimental Example 1-1, except that Compound 4 was used instead of Compound 1 in Experimental Example 1-1.

Experimental Example 1-5

An organic electronic device was manufactured in the same manner as in Experimental Example 1-1, except that Compound 5 was used instead of Compound 1 in Experimental Example 1-1.

Experimental Example 1-6

An organic electronic device was manufactured in the same manner as in Experimental Example 1-1, except that Compound 6 was used instead of Compound 1 in Experimental Example 1-1.

Experimental Example 1-7

An organic electronic device was manufactured in the same manner as in Experimental Example 1-1, except that Compound 7 was used instead of Compound 1 in Experimental Example 1-1.

Comparative Example 1-1

An organic electronic device was manufactured in the same manner as in Experimental Example 1-1, except that the following compound HAT-CN was used instead of Compound 1 in Experimental Example 1-1.

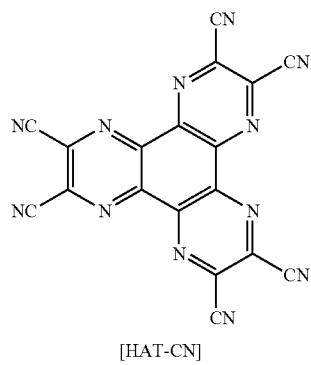 [SMILES: N#Cc1nc2c3nc(C#N)c(C#N)nc3c3nc(C#N)c(C#N)nc3c2nc1C#N]

[HAT-CN]

Comparative Example 1-2

An organic electronic device was manufactured in the same manner as in Experimental Example 1-1, except a hole injection layer was formed without any doping instead of Compound 1 in Experimental Example 1-1.

Comparative Example 1-3

An organic electronic device was manufactured in the same manner as in Experimental Example 1-1, except that the following Compound A was used instead of Compound 1 in Experimental Example 1-1.

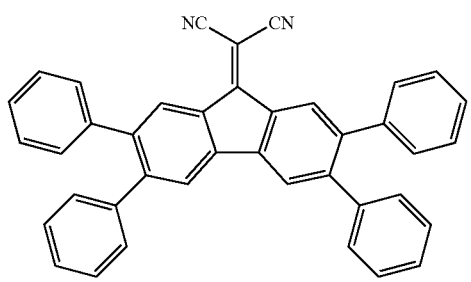

[Compound A]

Comparative Example 1-4

An organic electronic device was manufactured in the same manner as in Experimental Example 1-1, except that the following Compound B was used instead of Compound 1 in Experimental Example 1-1.

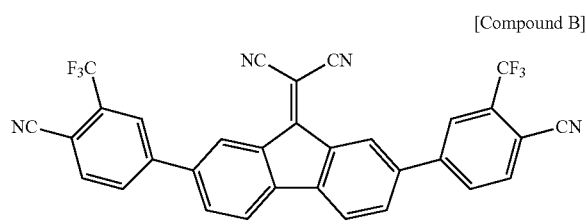 [SMILES: N#CC(C#N)=C1c2cc(-c3ccc(C#N)c(C(F)(F)F)c3)ccc2-c2ccc(-c3ccc(C#N)c(C(F)(F)F)c3)cc21]

[Compound B]

The driving voltages, current efficiencies, and color coordinates of the organic electronic devices manufactured in Experimental Examples 1-1 to 1-7 and Comparative Examples 1-1 to 1-4 are shown in the following Table 1.

TABLE 1

| | Doping Material for hole injection layer | Voltage (V@10 mA/cm$^2$) | Efficiency (cd/A@10 mA/cm$^2$) | Color coordinate (x, y) |
|---|---|---|---|---|
| Experimental Example 1-1 | Compound 1 | 3.82 | 5.41 | (0.136, 0.125) |
| Experimental Example 1-2 | Compound 2 | 3.86 | 5.41 | (0.136, 0.127) |
| Experimental Example 1-3 | Compound 3 | 3.84 | 5.48 | (0.136, 0.125) |
| Experimental Example 1-4 | Compound 4 | 3.81 | 5.41 | (0.137, 0.125) |
| Experimental Example 1-5 | Compound 5 | 3.85 | 5.47 | (0.138, 0.126) |
| Experimental Example 1-6 | Compound 6 | 3.82 | 5.46 | (0.136, 0.125) |
| Experimental Example 1-7 | Compound 7 | 3.86 | 5.40 | (0.137, 0.125) |
| Comparative Example 1-1 | HAT-CN | 4.13 | 5.01 | (0.136, 0.127) |
| Comparative Example 1-2 | — | 7.52 | 2.13 | (0.137, 0.126) |
| Comparative Example 1-3 | Compound A | 5.45 | 3.62 | (0.135, 0.125) |
| Comparative Example 1-4 | Compound B | 5.27 | 3.48 | (0.136, 0.127) |

Experimental Example 2-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator. Compound 1 was formed to have a thickness of 40 Å as a hole injection layer on the transparent ITO electrode, which was thus prepared, and NPB was subsequently formed to have a thickness of 800 Å as a hole transport layer. Subsequently, CBP of the following Chemical Formula being a host was doped with Ir(ppy)$_3$ of the following Chemical Formula as a dopant at a doping concentration of 10 wt %, thereby forming a yellow light emitting layer to have a thickness of 300 Å on the hole transport layer.

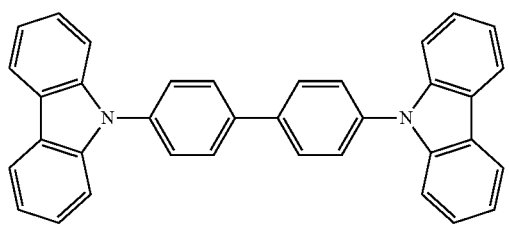

[CBP]

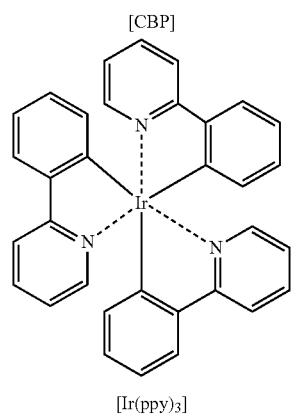

[Ir(ppy)$_3$]

Subsequently, BCP of the following Chemical Formula was vacuum deposited to have a thickness of 50 Å on the light emitting layer, thereby forming a hole blocking layer.

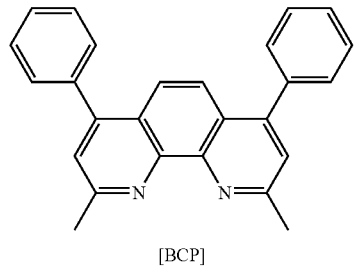

[BCP]

Subsequently, Alq$_3$ of the following Chemical Formula was vacuum deposited to have a thickness of 150 Å on the hole blocking layer, thereby forming an electron transport layer, and lithium fluoride (LiF) and aluminum were sequentially deposited to have a thickness of 5 Å and 1,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic electronic device.

Experimental Example 2-2

An organic electronic device was manufactured in the same manner as in Experimental Example 2-1, except that Compound 2 was used instead of Compound 1 in Experimental Example 2-1.

Experimental Example 2-3

An organic electronic device was manufactured in the same manner as in Experimental Example 2-1, except that Compound 3 was used instead of Compound 1 in Experimental Example 2-1.

Experimental Example 2-4

An organic electronic device was manufactured in the same manner as in Experimental Example 2-1, except that Compound 4 was used instead of Compound 1 in Experimental Example 2-1.

Experimental Example 2-5

An organic electronic device was manufactured in the same manner as in Experimental Example 2-1, except that Compound 5 was used instead of Compound 1 in Experimental Example 2-1.

Experimental Example 2-6

An organic electronic device was manufactured in the same manner as in Experimental Example 2-1, except that Compound 6 was used instead of Compound 1 in Experimental Example 2-1.

Experimental Example 2-7

An organic electronic device was manufactured in the same manner as in Experimental Example 2-1, except that Compound 7 was used instead of Compound 1 in Experimental Example 2-1.

Comparative Example 2-1

An organic electronic device was manufactured in the same manner as in Experimental Example 2-1, except that HAT-CN was used instead of Compound 1 in Experimental Example 2-1.

Comparative Example 2-2

An organic electronic device was manufactured in the same manner as in Experimental Example 2-1, except that the hole injection layer was omitted in Experimental Example 2-1.

Comparative Example 2-3

An organic electronic device was manufactured in the same manner as in Experimental Example 2-1, except that Compound C was used instead of Compound 1 in Experimental Example 2-1.

[Compound C]

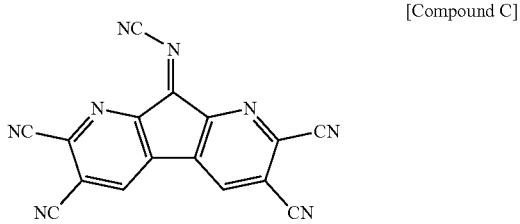 [SMILES: N#CN=C1c2nc(C#N)c(C#N)cc2-c2cc(C#N)c(C#N)nc21]

Comparative Example 2-4

An organic electronic device was manufactured in the same manner as in Experimental Example 2-1, except that Compound D was used instead of Compound 1 in Experimental Example 2-1.

[Compound D]

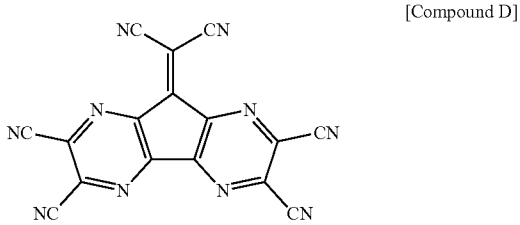 [SMILES: N#CC(C#N)=C1c2nc(C#N)c(C#N)nc2-c2nc(C#N)c(C#N)nc21]

The driving voltages, current efficiencies, and color coordinates of the organic electronic devices manufactured in Experimental Examples 2-1 to 2-7 and Comparative Examples 2-1 to 2-4 are shown in the following Table 2.

TABLE 2

| | Material for hole injection layer | Voltage (V@10 mA/cm$^2$) | Efficiency (cd/A@10 mA/cm$^2$) | Color coordinate (x, y) |
|---|---|---|---|---|
| Experimental Example 2-1 | Compound 1 | 4.02 | 6.55 | (0.320, 0.611) |
| Experimental Example 2-2 | Compound 2 | 4.04 | 6.52 | (0.321, 0.611) |
| Experimental Example 2-3 | Compound 3 | 4.02 | 6.56 | (0.320, 0.612) |
| Experimental Example 2-4 | Compound 4 | 4.06 | 6.51 | (0.320, 0.611) |
| Experimental Example 2-5 | Compound 5 | 4.01 | 6.54 | (0.322, 0.610) |
| Experimental Example 2-6 | Compound 6 | 4.00 | 6.52 | (0.319, 0.611) |
| Experimental Example 2-7 | Compound 7 | 4.08 | 6.56 | (0.321, 0.610) |
| Comparative Example 2-1 | HAT-CN | 4.13 | 5.87 | (0.320, 0.611) |
| Comparative Example 2-2 | — | 8.52 | 2.13 | (0.318, 0.613) |
| Comparative Example 2-3 | Compound C | 4.21 | 5.62 | (0.320, 0.611) |
| Comparative Example 2-4 | Compound D | 4.28 | 5.58 | (0.321, 0.610) |

Experimental Example 3-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

HAT-CN was thermally vacuum deposited to have a thickness of 50 Å on the transparent ITO electrode, which was thus prepared, thereby forming a hole injection layer, and NPB was subsequently vacuum deposited to have a thickness of 1,750 Å, thereby forming Hole Transport Layer 1. Subsequently, the following compound HTL 2 was vacuum deposited to have a film thickness of 150 Å on Hole Transport Layer 1, thereby forming Hole Transport Layer 2.

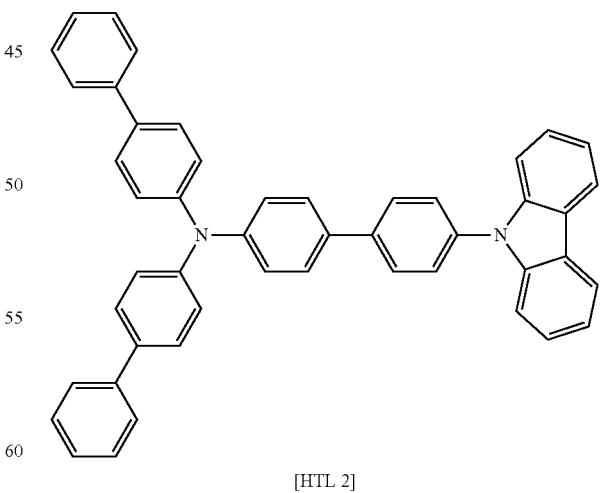

[HTL 2]

Subsequently, the following BH and BD were vacuum deposited at a weight ratio of 25:1 to have a film thickness of 250 Å on Hole Transport Layer 2, thereby forming a blue light emitting layer.

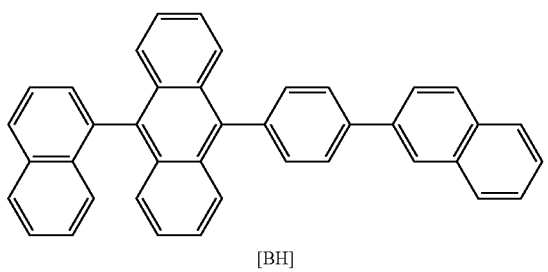

[BH]

Subsequently, the following compound ETL 1 was vacuum deposited to have a thickness of 200 Å on the blue light emitting layer, thereby forming Electron Transport Layer 1.

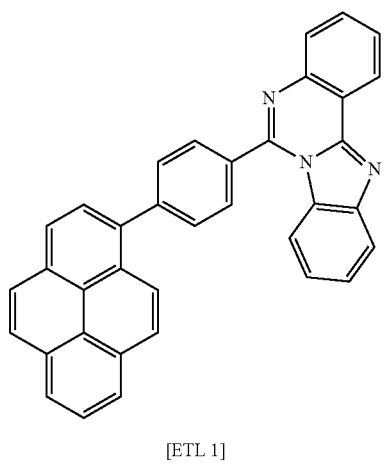 [SMILES: c1cc2ccc3ccc(-c4ccc(-c5nc6ccccc6c6nc7ccccc7n56)cc4)c4ccc(c1)c2c34]

[ETL 1]

Subsequently, the following compound N-type charge generation layer and the following compound lithium quinolate (LiQ) were vacuum deposited at a weight ratio of 50:1 on Electron Transport Layer 1, thereby forming an N-type charge generation layer having a thickness of 110 Å.

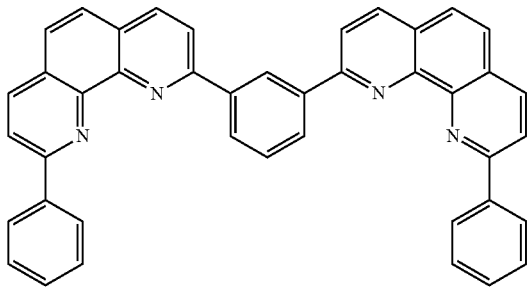

[N-Type Charge Generation Layer]

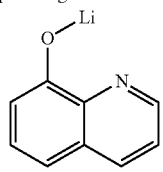

[LiQ]

Subsequently, Compound 1 was thermally vacuum deposited to have a thickness of 50 Å on the N-type charge generation layer, thereby forming a P-type charge generation layer, and the following compound HTL 3 being a material for transporting holes was vacuum deposited to have a thickness of 650 Å, thereby forming Hole Transport Layer 3.

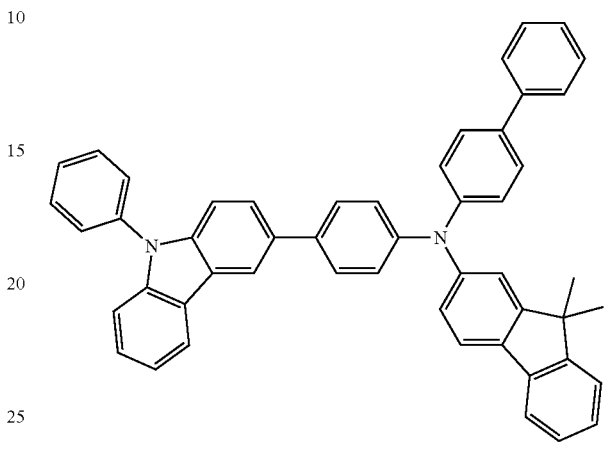

[HTL 3]

Subsequently, the following compound HTL 4 was vacuum deposited to have a film thickness of 150 Å on Hole Transport Layer 3, thereby forming an electron blocking layer.

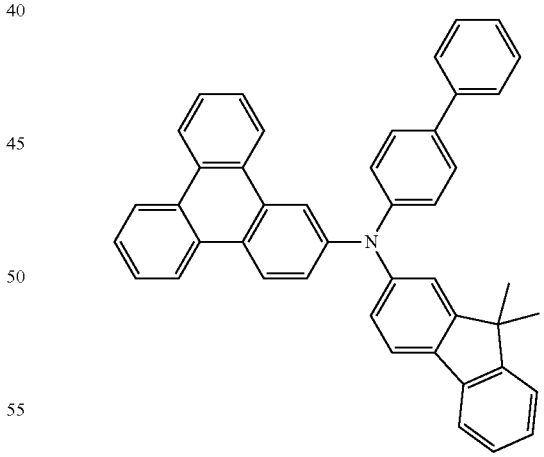

[HTL 4]

Subsequently, the following YGH and YGD were vacuum deposited at a weight ratio of 25:3 to have a film thickness of 250 Å on the electron blocking layer, thereby forming a green light emitting layer.

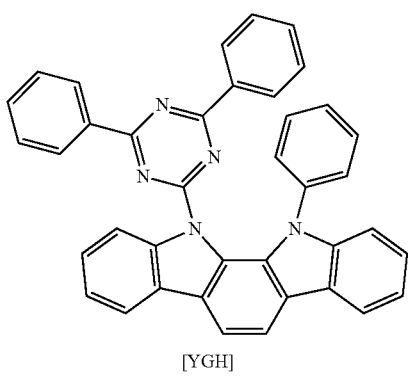

[YGH]

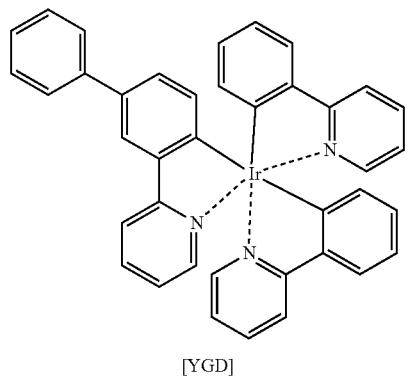

[YGD]

Subsequently, the following compound ETL 2 was vacuum deposited to have a thickness of 450 Å on the green light emitting layer, thereby forming Electron Transport Layer 2.

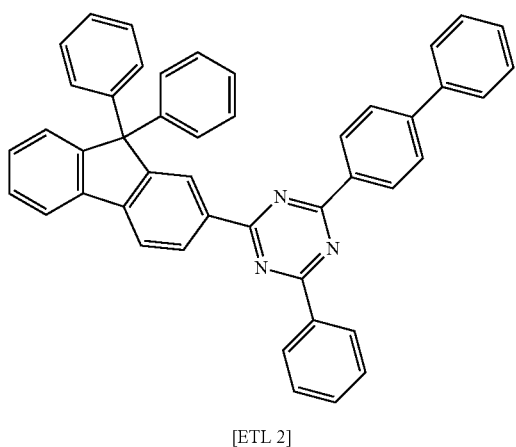 [SMILES: c1ccc(-c2ccc(-c3nc(-c4ccccc4)nc(-c4ccc5c(c4)C(c4ccccc4)(c4ccccc4)c4ccccc4-5)n3)cc2)cc1]

[ETL 2]

Lithium fluoride (LiF) and aluminum were sequentially deposited to have a thickness of 12 Å and 2,000 Å, respectively, on Electron Transport Layer 2, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic electronic device.

Experimental Example 3-2

An organic electronic device was manufactured in the same manner as in Experimental Example 3-1, except that Compound 2 was used instead of Compound 1 used in the P-type charge generation layer in Experimental Example 3-1.

Experimental Example 3-3

An organic electronic device was manufactured in the same manner as in Experimental Example 3-1, except that Compound 3 was used instead of Compound 1 used in the P-type charge generation layer in Experimental Example 3-1.

Experimental Example 3-4

An organic electronic device was manufactured in the same manner as in Experimental Example 3-1, except that Compound 4 was used instead of Compound 1 used in the P-type charge generation layer in Experimental Example 3-1.

Experimental Example 3-5

An organic electronic device was manufactured in the same manner as in Experimental Example 3-1, except that Compound 5 was used instead of Compound 1 used in the P-type charge generation layer in Experimental Example 3-1.

Experimental Example 3-6

An organic electronic device was manufactured in the same manner as in Experimental Example 3-1, except that Compound 6 was used instead of Compound 1 used in the P-type charge generation layer in Experimental Example 3-1.

Experimental Example 3-7

An organic electronic device was manufactured in the same manner as in Experimental Example 3-1, except that Compound 7 was used instead of Compound 1 used in the P-type charge generation layer in Experimental Example 3-1.

Comparative Example 3-1

An organic electronic device was manufactured in the same manner as in Experimental Example 3-1, except that HAT-CN was used instead of Compound 1 used in the P-type charge generation layer in Experimental Example 3-1.

Comparative Example 3-2

An organic electronic device was manufactured in the same manner as in Experimental Example 3-1, except that Compound A was used instead of Compound 1 used in the P-type charge generation layer in Experimental Example 3-1.

Comparative Example 3-3

An organic electronic device was manufactured in the same manner as in Experimental Example 3-1, except that Compound B was used instead of Compound 1 used in the P-type charge generation layer in Experimental Example 3-1.

The driving voltages, current efficiencies, and color coordinates of the organic electronic devices manufactured in Experimental Examples 3-1 to 3-7 and Comparative Examples 3-1 to 3-3 are shown in the following Table 3.

TABLE 3

| | Material for P-type charge generation layer | Voltage (V@10 mA/cm$^2$) | Efficiency (cd/A@10 mA/cm$^2$) | Color coordinate (x, y) |
|---|---|---|---|---|
| Experimental Example 3-1 | Compound 1 | 7.59 | 74.42 | (0.335, 0.410) |
| Experimental Example 3-2 | Compound 2 | 7.55 | 74.41 | (0.335, 0.408) |
| Experimental Example 3-3 | Compound 3 | 7.51 | 74.38 | (0.385, 0.409) |
| Experimental Example 3-4 | Compound 4 | 7.52 | 74.51 | (0.333, 0.410) |
| Experimental Example 3-5 | Compound 5 | 7.53 | 74.48 | (0.334, 0.411) |
| Experimental Example 3-6 | Compound 6 | 7.48 | 74.48 | (0.335, 0.410) |
| Experimental Example 3-7 | Compound 7 | 7.55 | 74.37 | (0.336, 0.407) |
| Comparative Example 3-1 | HAT-CN | 8.10 | 69.41 | (0.335, 0.410) |
| Comparative Example 3-2 | Compound A | 10.30 | 57.42 | (0.338, 0.408) |
| Comparative Example 3-3 | Compound B | 9.12 | 62.15 | (0.334, 0.411) |

Experimental Example 4-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

HAT-CN was thermally vacuum deposited to have a thickness of 50 Å on the transparent ITO electrode, which was thus prepared, thereby forming a hole injection layer, and NPB was subsequently vacuum deposited to have a thickness of 1,750 Å, thereby forming Hole Transport Layer 1. Subsequently, Compound HTL 2 was vacuum deposited to have a film thickness of 150 Å on Hole Transport Layer 1, thereby forming Hole Transport Layer 2, and BH and BD were vacuum deposited at a weight ratio of 25:1 to have a film thickness of 250 Å thereon, thereby forming a blue light emitting layer. Subsequently, the compound ETL 1 was vacuum deposited to have a thickness of 200 Å on the blue light emitting layer, thereby forming Electron Transport Layer 1, and the compound N-type charge generation layer and the compound lithium quinolate (LiQ) were vacuum deposited at a weight ratio of 50:1 thereon, thereby forming an N-type charge generation layer having a thickness of 110 Å. Subsequently, HTL3 was formed to have a thickness of 100 Å, in which HTL3 was doped with Compound 1 at a doping concentration of 25 wt %, and the compound HTL 3 was vacuum deposited to have a thickness of 600 Å, thereby forming Hole Transport Layer 3. Subsequently, Compound HTL 4 was vacuum deposited to have a film thickness of 150 Å on Hole Transport Layer 3, thereby forming an electron blocking layer, and YGH and YGD were vacuum deposited at a weight ratio of 25:3 to have a film thickness of 250 Å thereon, thereby forming a green light emitting layer. Subsequently, the following compound ETL 2 was vacuum deposited to have a thickness of 450 Å on the green light emitting layer, thereby forming Electron Transport Layer 2, and lithium fluoride (LiF) and aluminum were sequentially deposited to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic electronic device.

Experimental Example 4-2

An organic electronic device was manufactured in the same manner as in Experimental Example 4-1, except that Compound 2 was used instead of Compound 1 used in the P-type charge generation layer in Experimental Example 4-1.

Experimental Example 4-3

An organic electronic device was manufactured in the same manner as in Experimental Example 4-1, except that Compound 3 was used instead of Compound 1 used in the P-type charge generation layer in Experimental Example 4-1.

Experimental Example 4-4

An organic electronic device was manufactured in the same manner as in Experimental Example 4-1, except that Compound 4 was used instead of Compound 1 used in the P-type charge generation layer in Experimental Example 4-1.

Experimental Example 4-5

An organic electronic device was manufactured in the same manner as in Experimental Example 4-1, except that Compound 5 was used instead of Compound 1 used in the P-type charge generation layer in Experimental Example 4-1.

Experimental Example 4-6

An organic electronic device was manufactured in the same manner as in Experimental Example 4-1, except that Compound 6 was used instead of Compound 1 used in the P-type charge generation layer in Experimental Example 4-1.

Experimental Example 4-7

An organic electronic device was manufactured in the same manner as in Experimental Example 4-1, except that Compound 7 was used instead of Compound 1 used in the P-type charge generation layer in Experimental Example 4-1.

Comparative Example 4-1

An organic electronic device was manufactured in the same manner as in Experimental Example 4-1, except that HAT-CN was used instead of Compound 1 used in the P-type charge generation layer in Experimental Example 4-1.

Comparative Example 4-2

An organic electronic device was manufactured in the same manner as in Experimental Example 4-1, except that Compound C was used instead of Compound 1 used in the P-type charge generation layer in Experimental Example 4-1.

Comparative Example 4-3

An organic electronic device was manufactured in the same manner as in Experimental Example 4-1, except that Compound D was used instead of Compound 1 used in the P-type charge generation layer in Experimental Example 4-1. The driving voltage, current efficiencies, and color coordinates of the organic electronic devices manufactured in Experimental Examples 4-1 to 4-7 and Comparative Examples 4-1 to 4-3 are shown in the following Table 4.

TABLE 4

| | Doping material for P-type charge generation layer | Voltage (V@10 mA/cm$^2$) | Efficiency (cd/A@10 mA/cm$^2$) | Color coordinate (x, y) |
|---|---|---|---|---|
| Experimental Example 4-1 | Compound 1 | 7.28 | 80.42 | (0.335, 0.410) |
| Experimental Example 4-2 | Compound 2 | 7.27 | 79.41 | (0.335, 0.410) |
| Experimental Example 4-3 | Compound 3 | 7.21 | 80.38 | (0.334, 0.409) |
| Experimental Example 4-4 | Compound 4 | 7.29 | 81.51 | (0.331, 0.411) |
| Experimental Example 4-5 | Compound 5 | 7.35 | 79.48 | (0.335, 0.48) |
| Experimental Example 4-6 | Compound 6 | 7.37 | 78.48 | (0.336, 0.410) |
| Experimental Example 4-7 | Compound 7 | 7.31 | 77.37 | (0.337, 0.409) |
| Comparative Example 4-1 | HAT-CN | 8.21 | 70.41 | (0.336, 0.411) |
| Comparative Example 4-2 | Compound C | 8.27 | 70.05 | (0.337, 0.412) |
| Comparative Example 4-3 | Compound D | 8.22 | 70.15 | (0.336, 0.408) |

Although the preferred exemplary embodiments of the present invention have been described above, the present invention is not limited thereto, and various modifications can be made and carried out within the scope of the claims and the detailed description of the invention, and also fall within the scope of the invention.

The invention claimed is:
1. An organic electronic device comprising:
a first electrode;
a second electrode provided to face the first electrode; and
one or more organic material layers provided between the first electrode and the second electrode,
wherein the one or more organic material layers comprise at least one of a hole injection layer or a hole transport layer, and the hole injection layer or the hole transport layer comprise a compound represented by the following Chemical Formula 1:

[Chemical Formula 1]

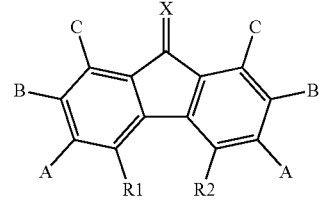

in Chemical Formula 1,
X is represented by any one of the following (a) to (d), (a)

(b)
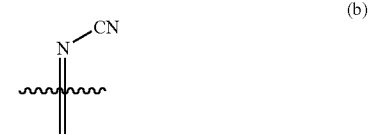

(c)
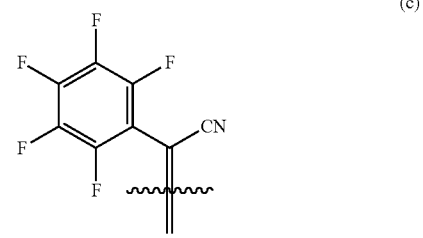

(d)
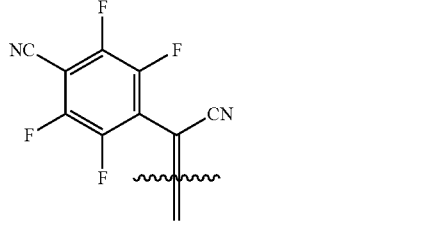

A and B are the same as or different from each other, and are each independently a cyano group; a fluoroalkyl group; a fluoroalkoxy group; a substituted or unsubstituted aryl group; or a substituted or unsubstituted heteroaryl group,
at least one of A or B is a cyano group; a fluoroalkyl group; or a fluoroalkoxy group,
when X is represented by formulas (a) or (b), at least one of A or B is a fluoroalkoxy group, or an aryl group substituted with a fluoroalkoxy group,
C is hydrogen; deuterium; a cyano group; a fluoroalkyl group; a fluoroalkoxy group; a substituted or unsubstituted aryl group; or a substituted or unsubstituted heteroaryl group, and R1 and R2 are the same as or different from each other, and are each independently hydrogen; deuterium; a halogen group; a cyano group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

2. The organic electronic device of claim 1, wherein A and B are the same as or different from each other, and are each independently —CN, —$C_nF_{2n+1}$, or —O—$C_nF_{2n+1}$, and n is 1 or 2.

3. The organic electronic device of claim 1, wherein the compound represented by Chemical Formula 1 is selected from the following structural formulae:

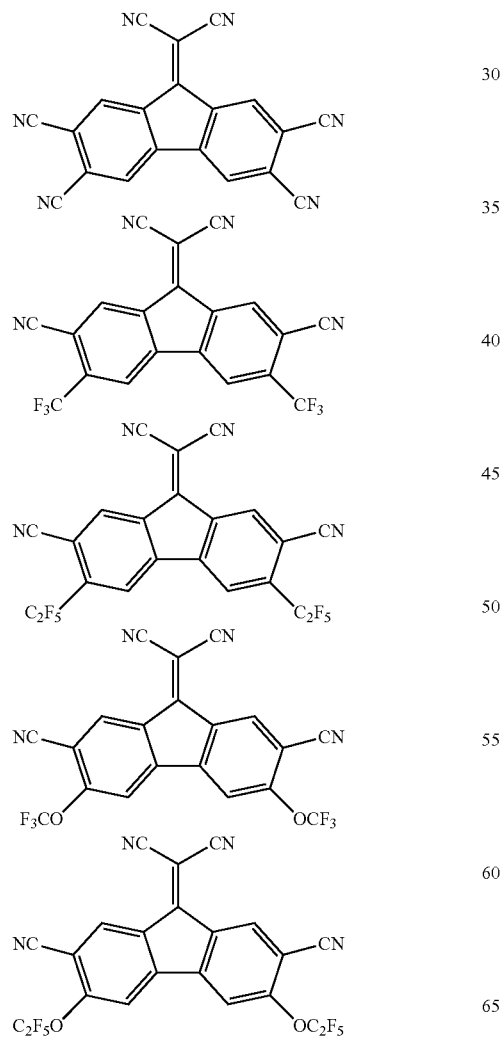

-continued

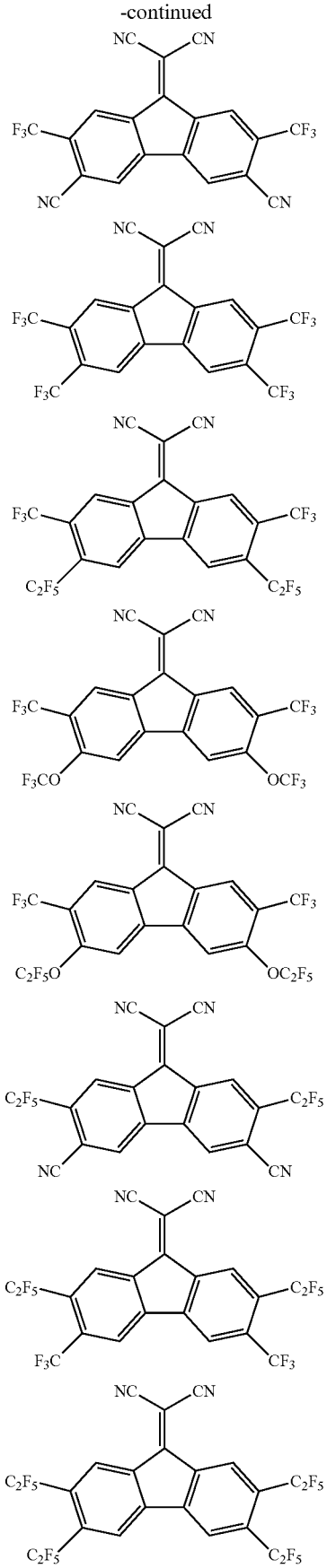

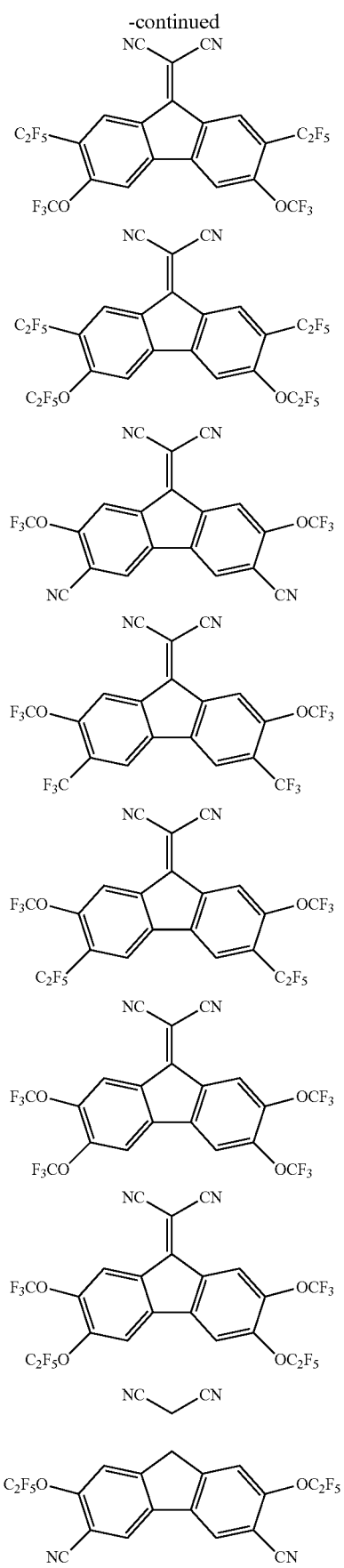
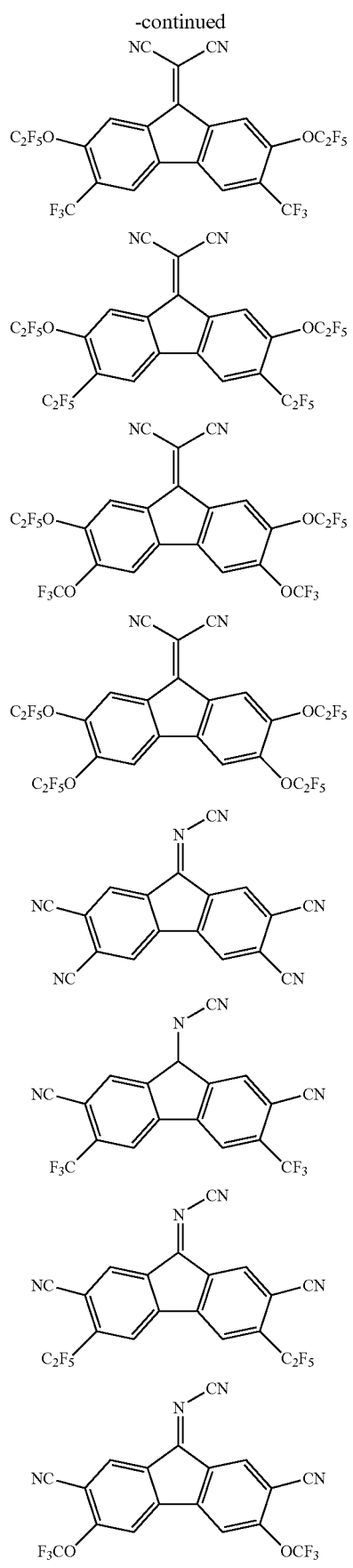

105
-continued
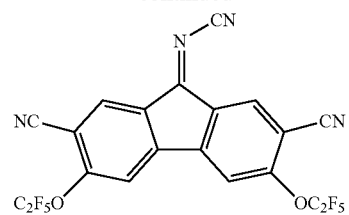
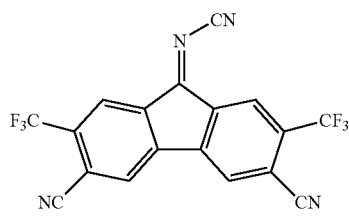
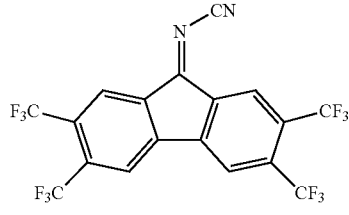
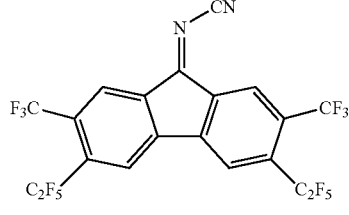
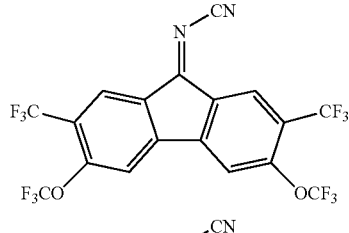
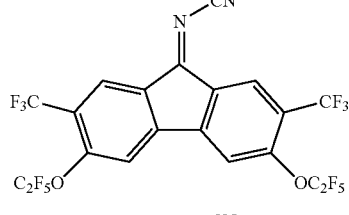
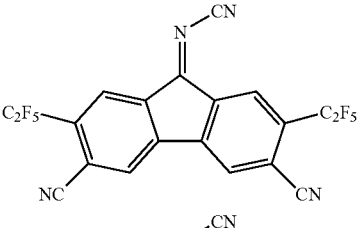
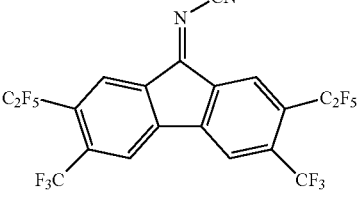
106
-continued
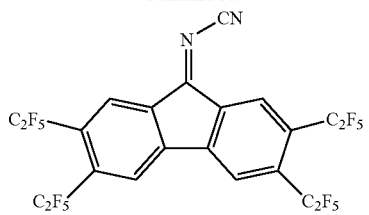
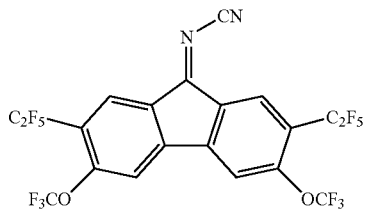
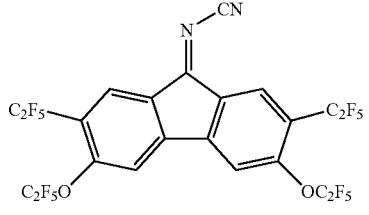
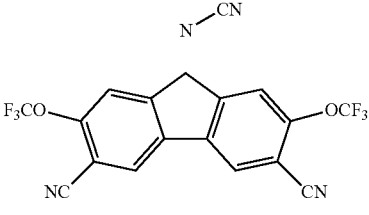
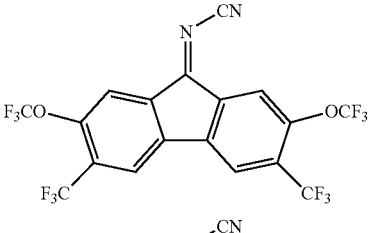
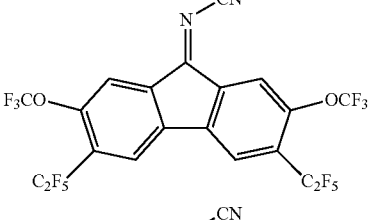
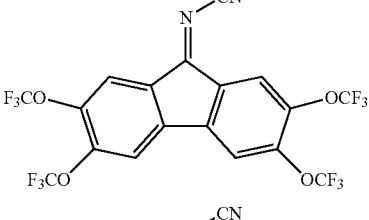
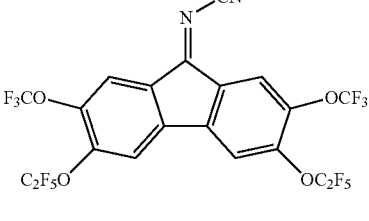

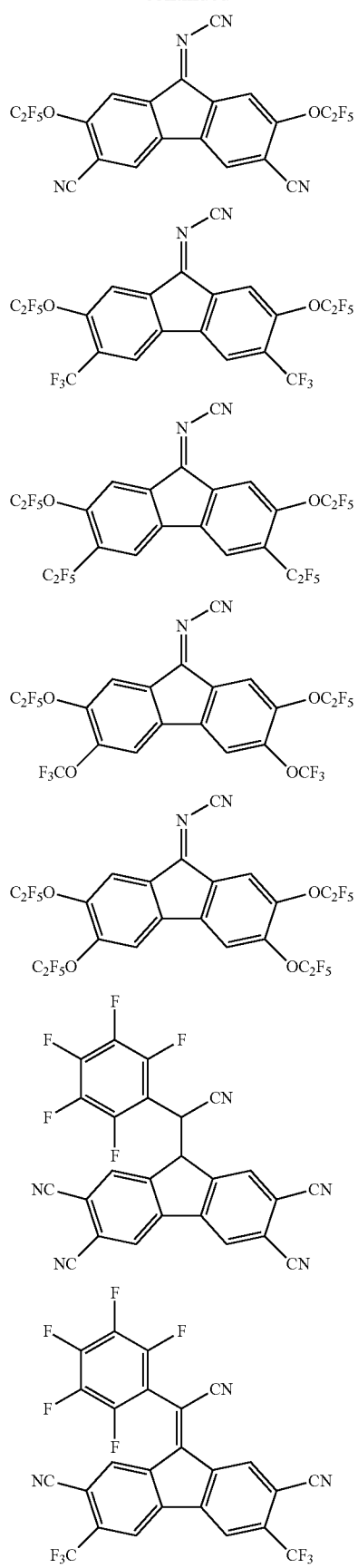
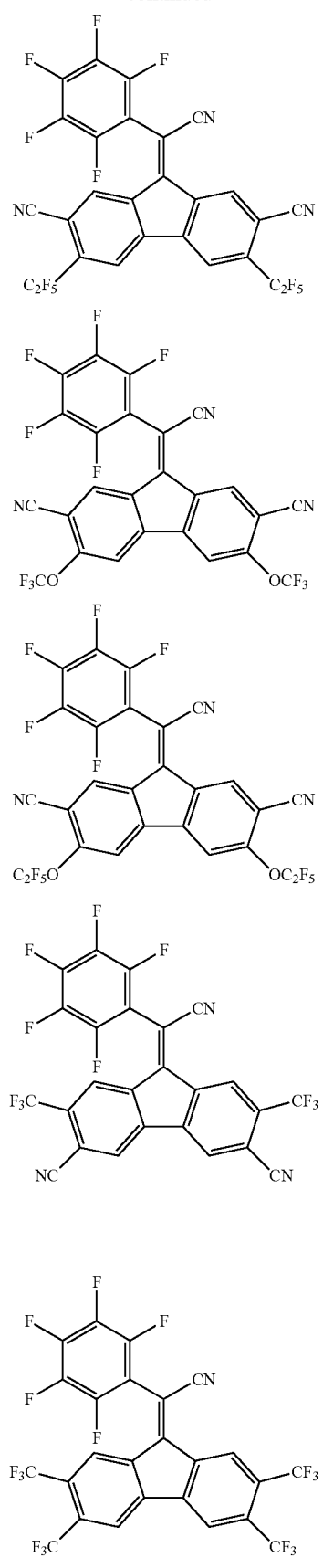

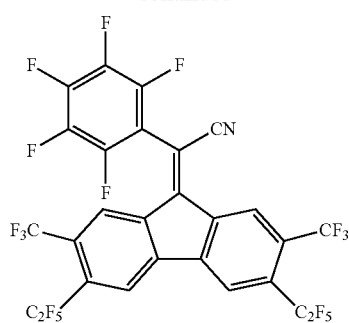
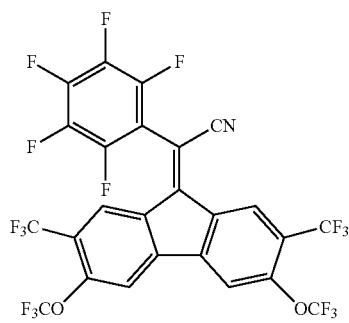
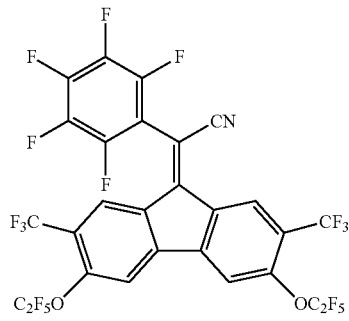
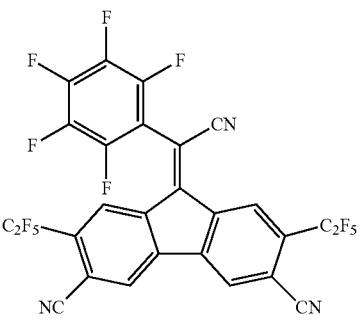
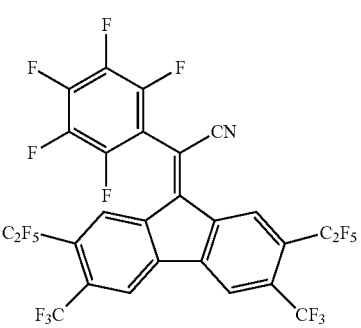
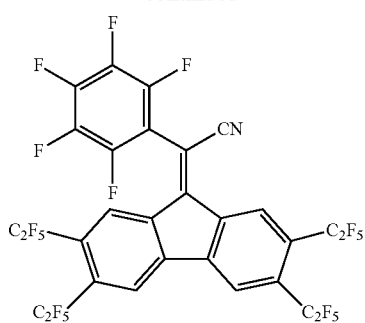
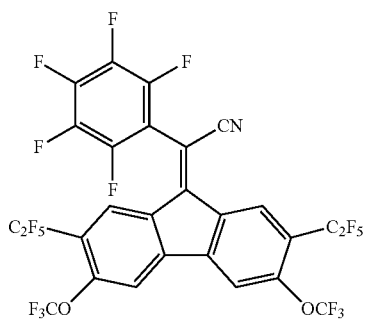
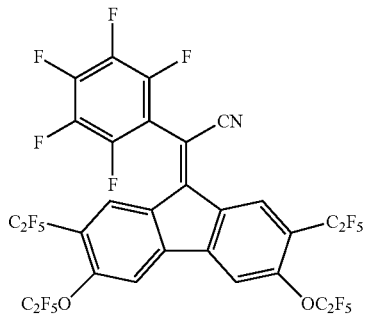
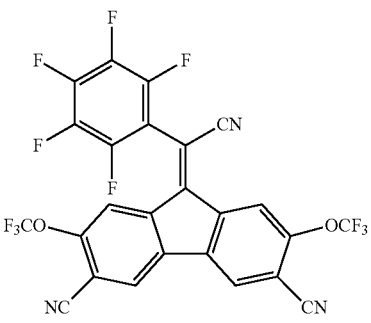
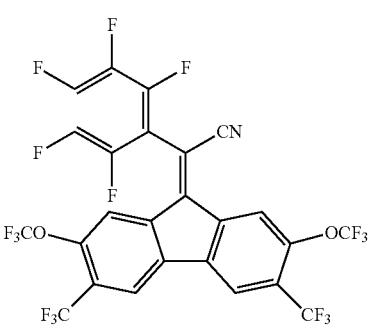

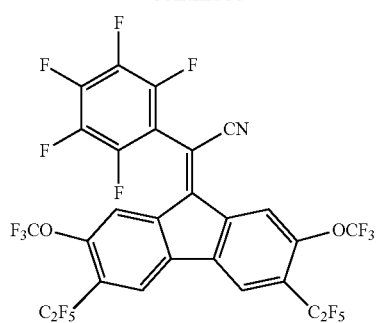
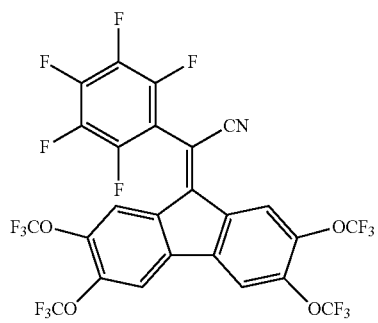
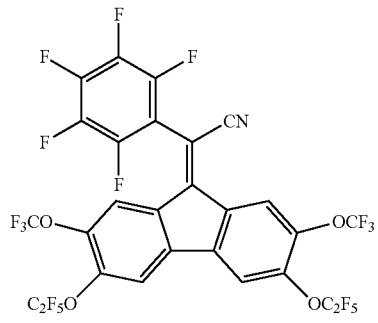
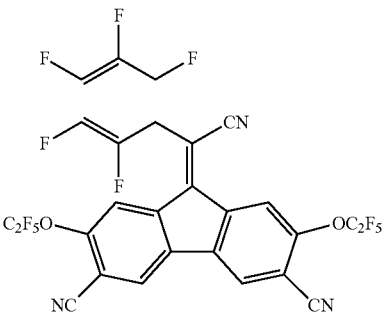
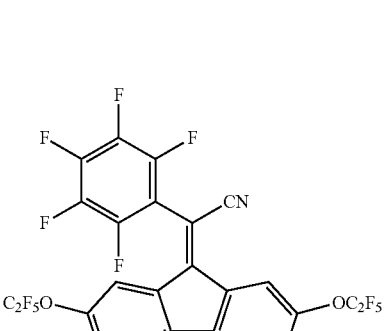
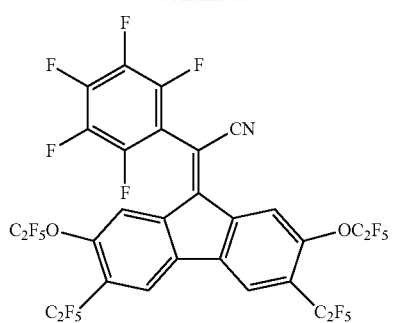
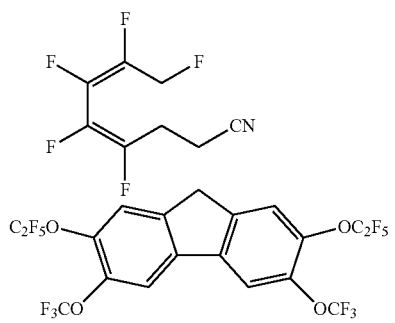
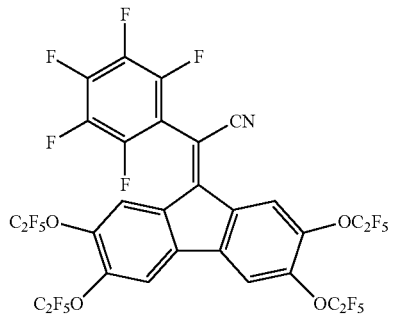
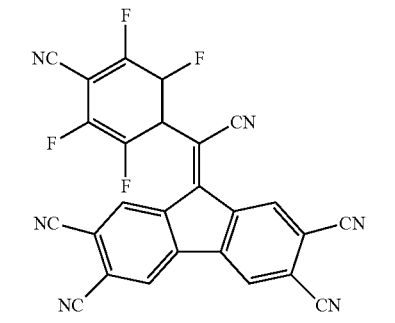
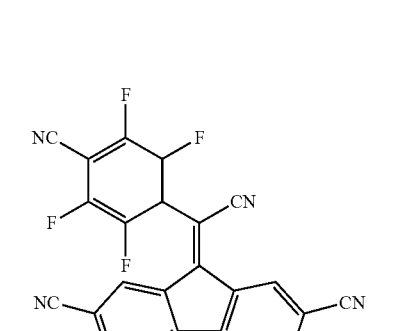

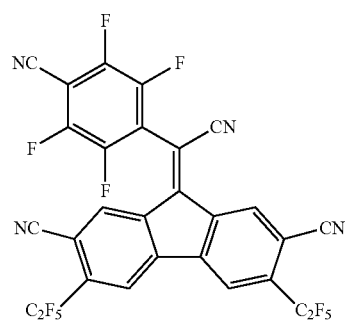
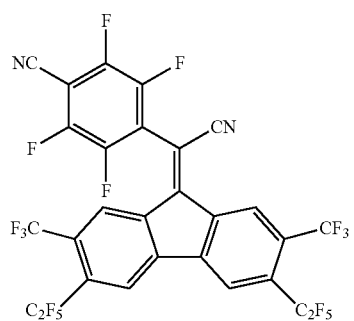
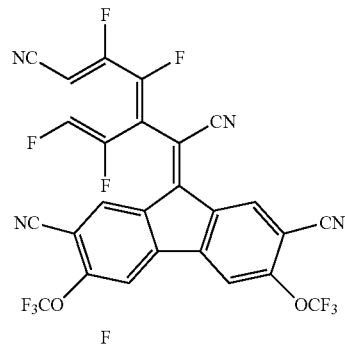
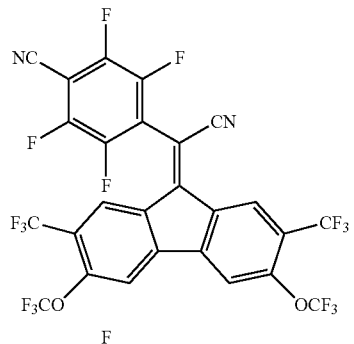
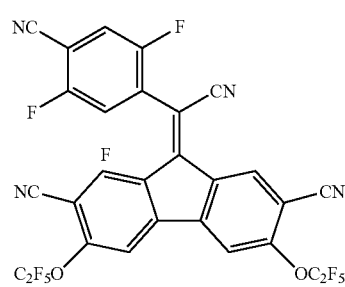
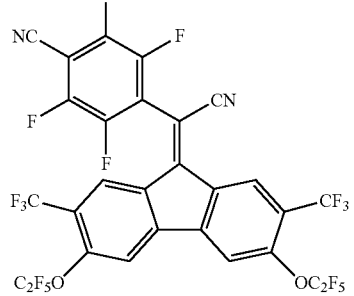
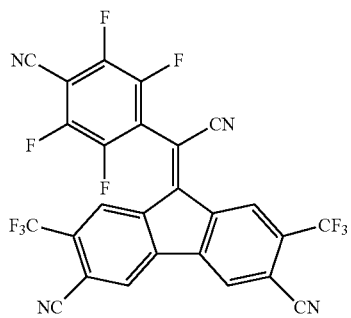
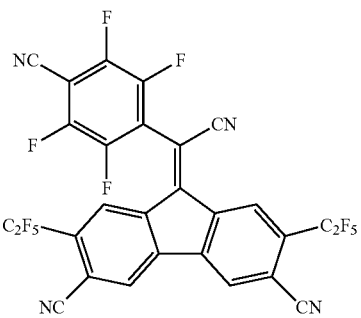
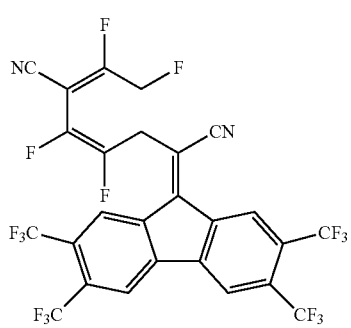
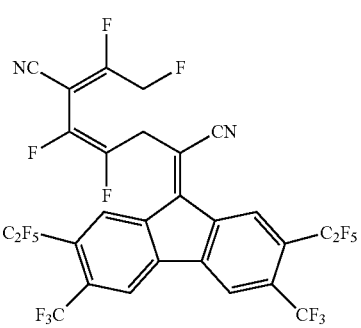

115
-continued
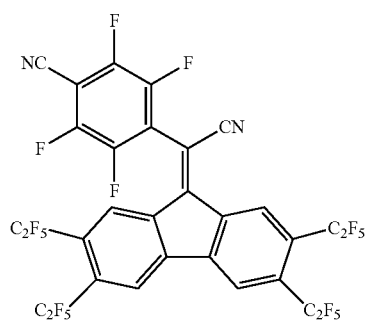
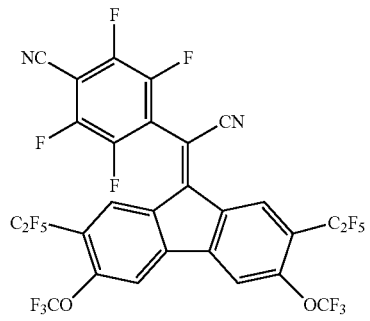
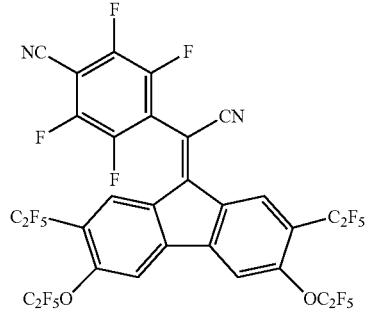
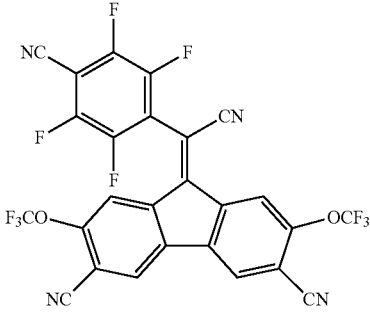
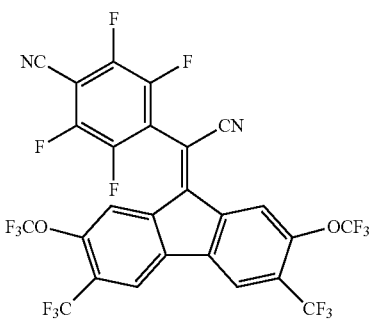
116
-continued
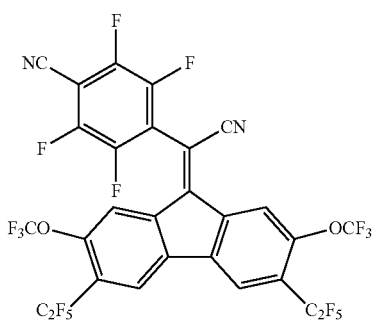
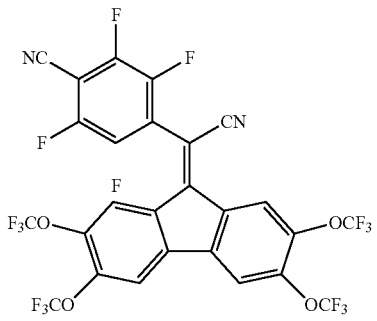
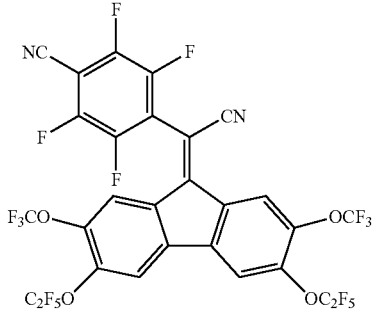
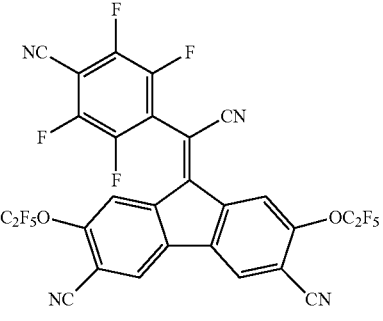
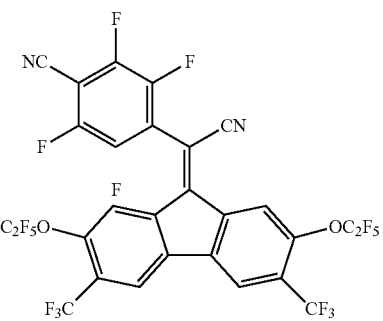

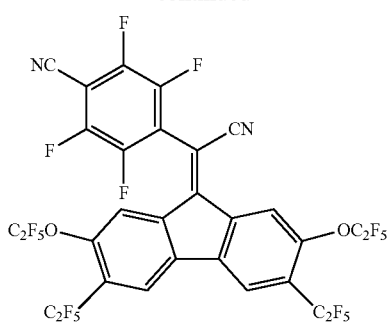
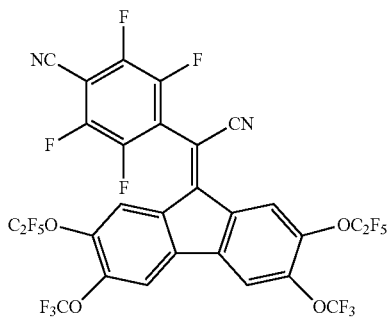
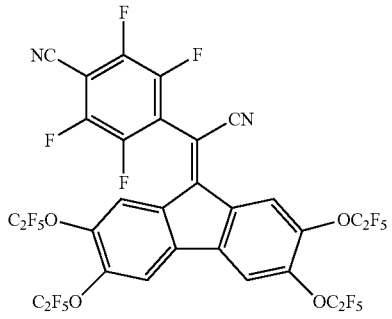
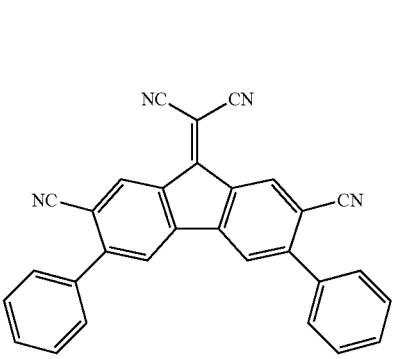
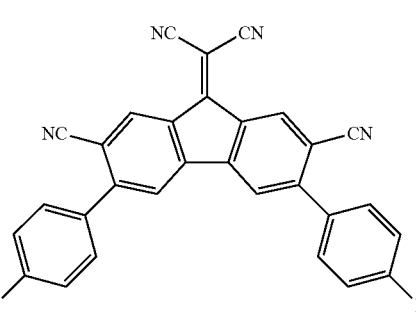
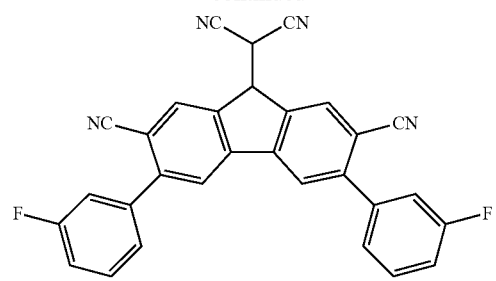
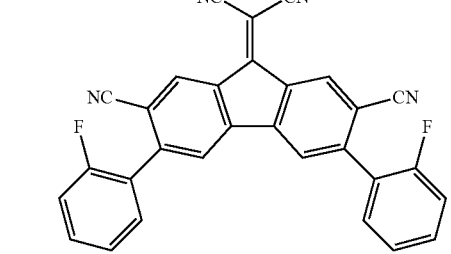
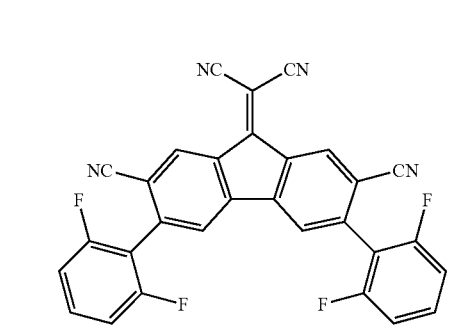
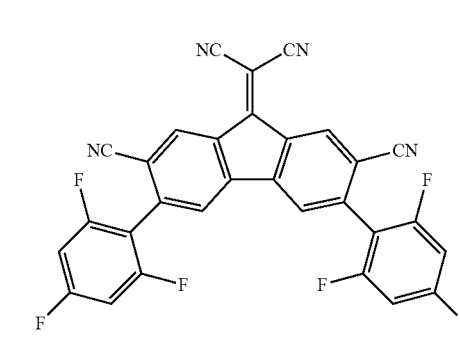
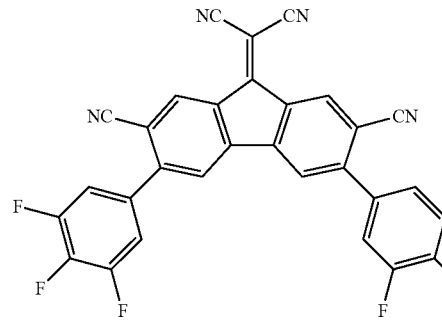

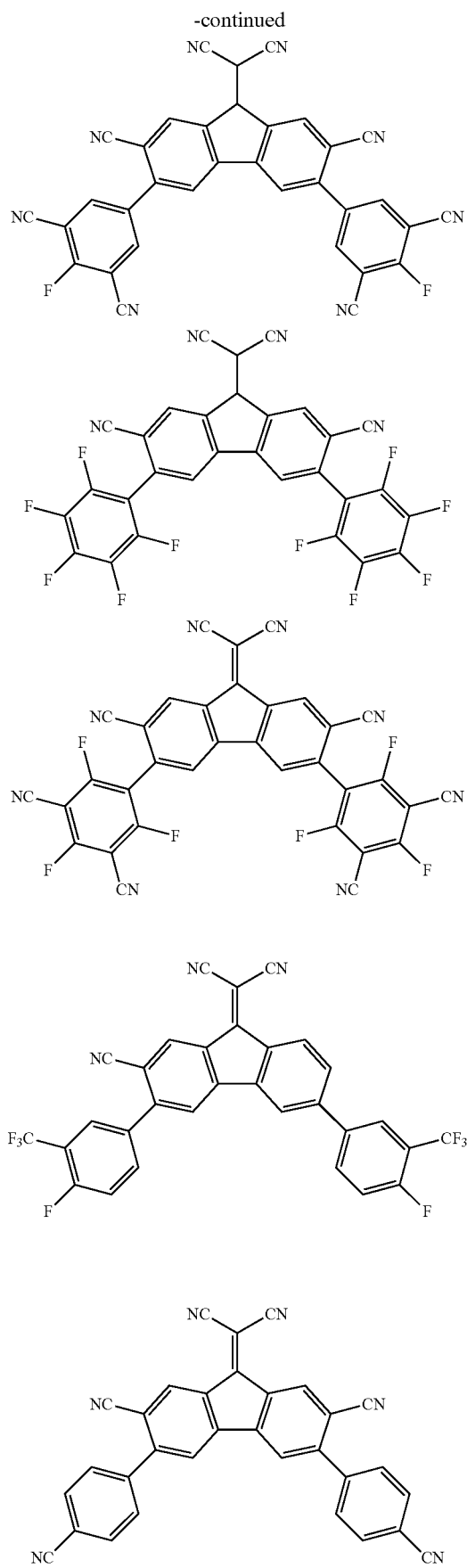

121
-continued
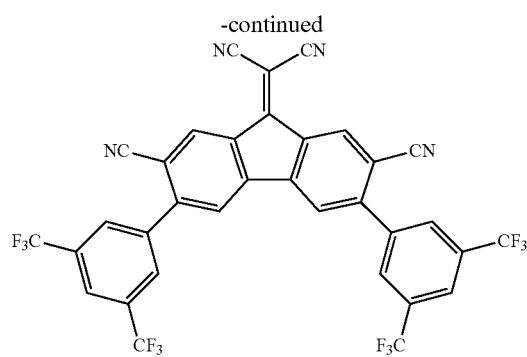
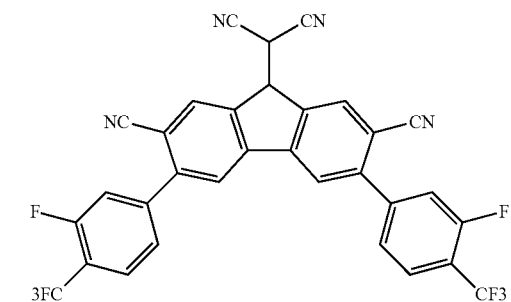
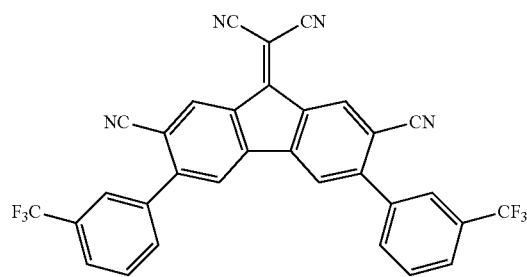
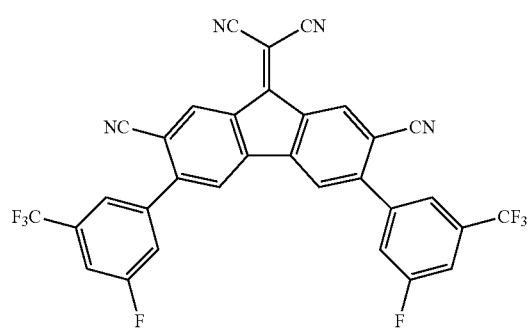
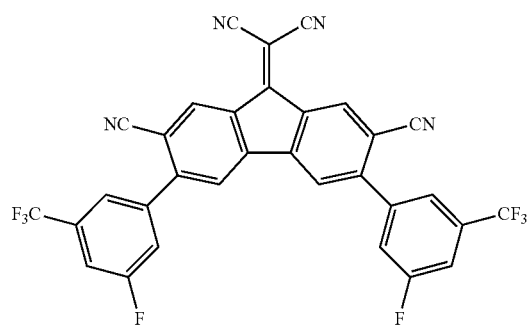
122
-continued
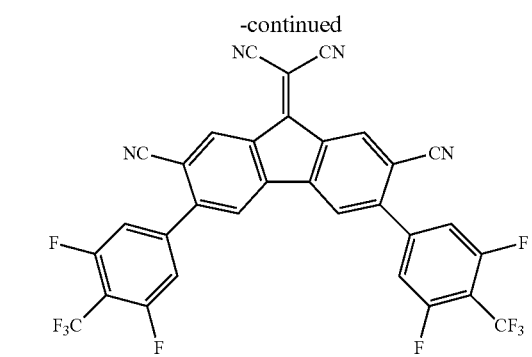
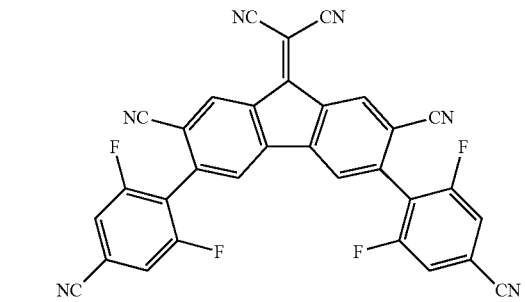
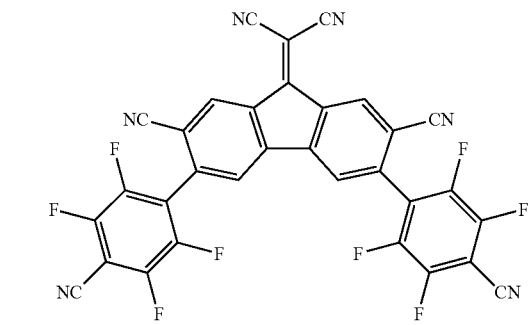
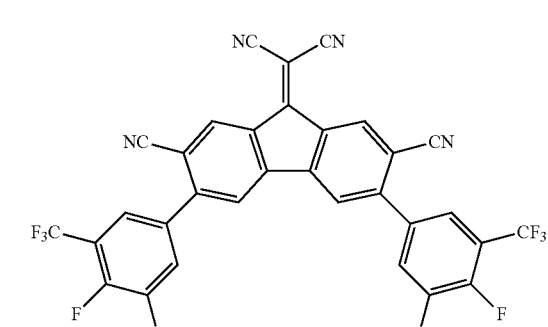
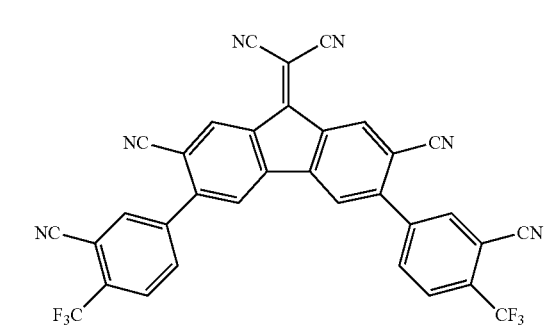

123
-continued
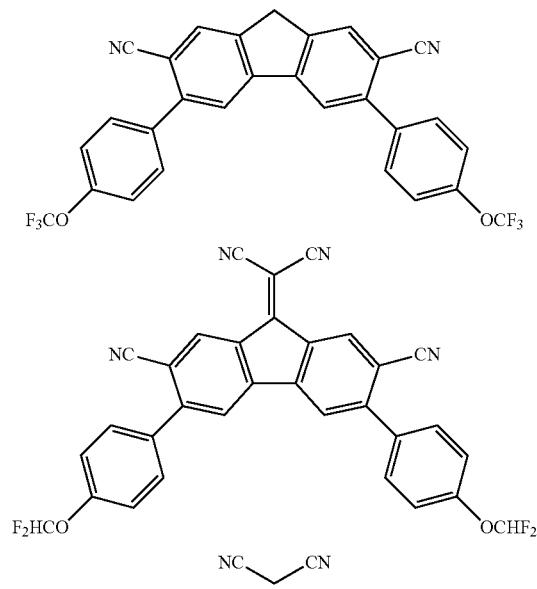
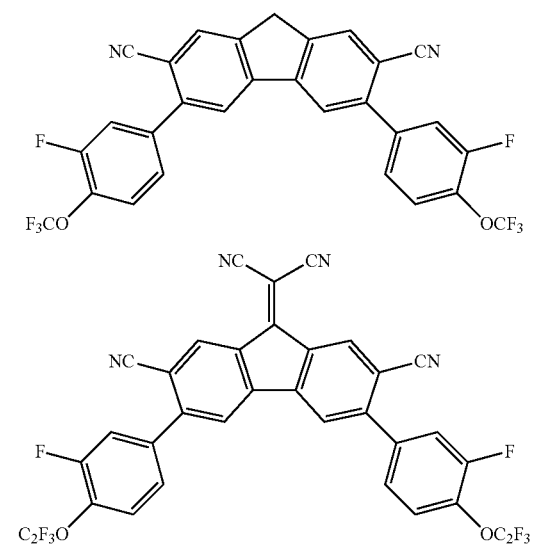
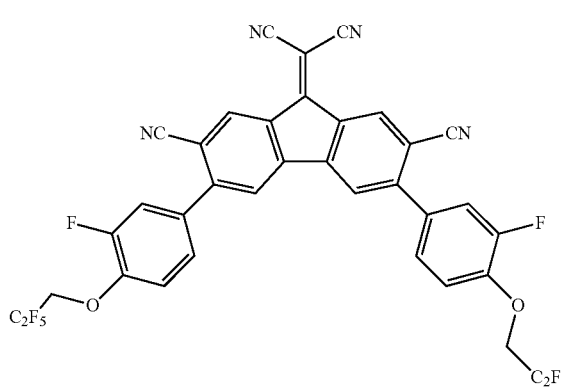
124
-continued
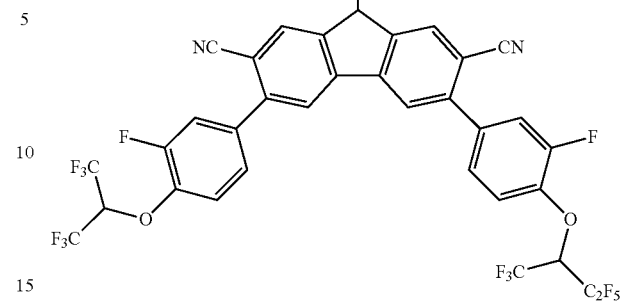
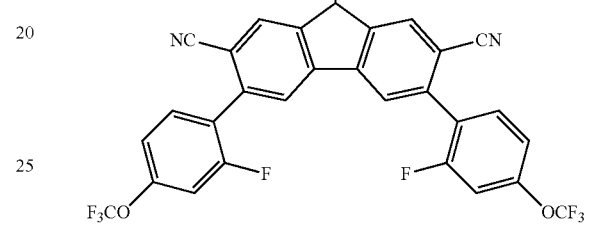
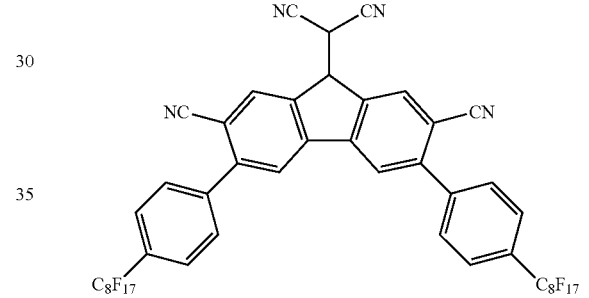
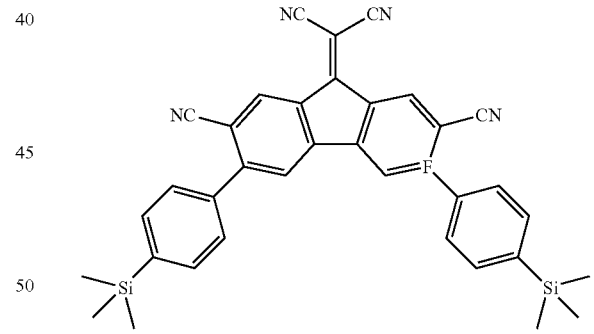
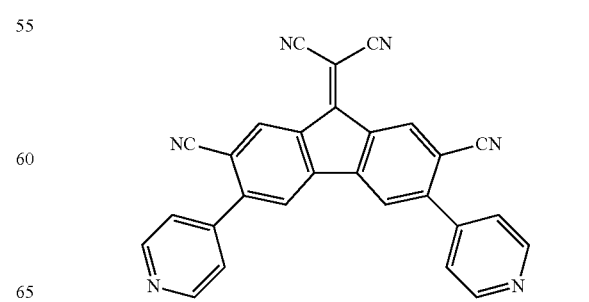

125
-continued
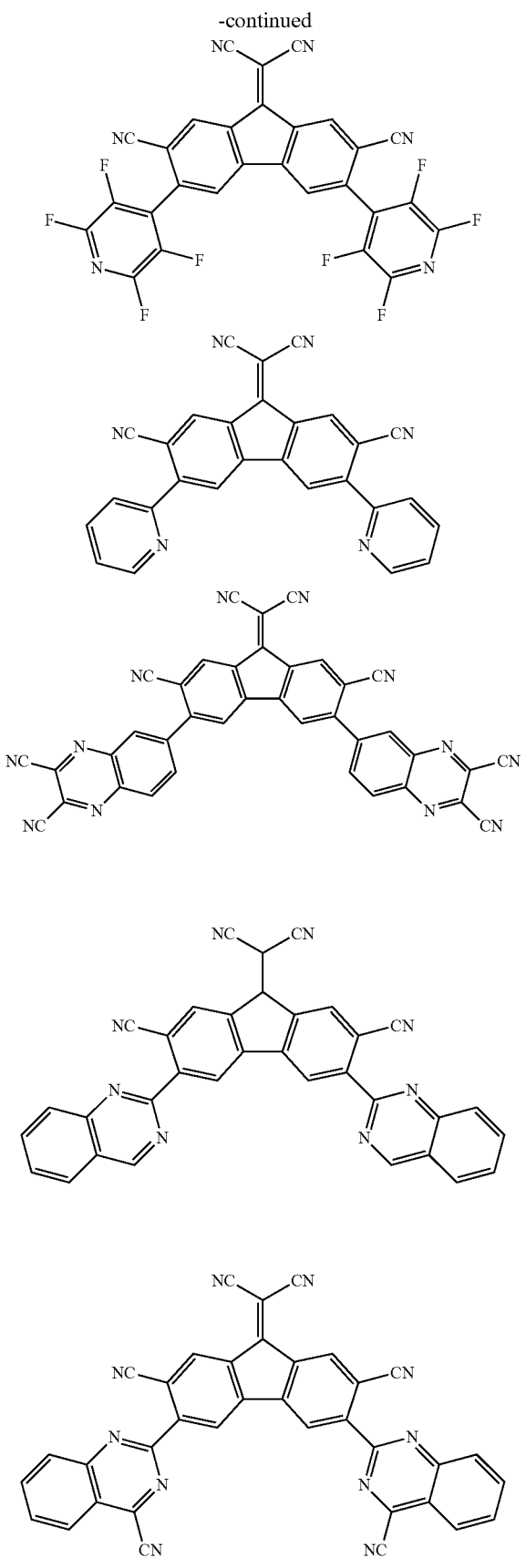
126
-continued
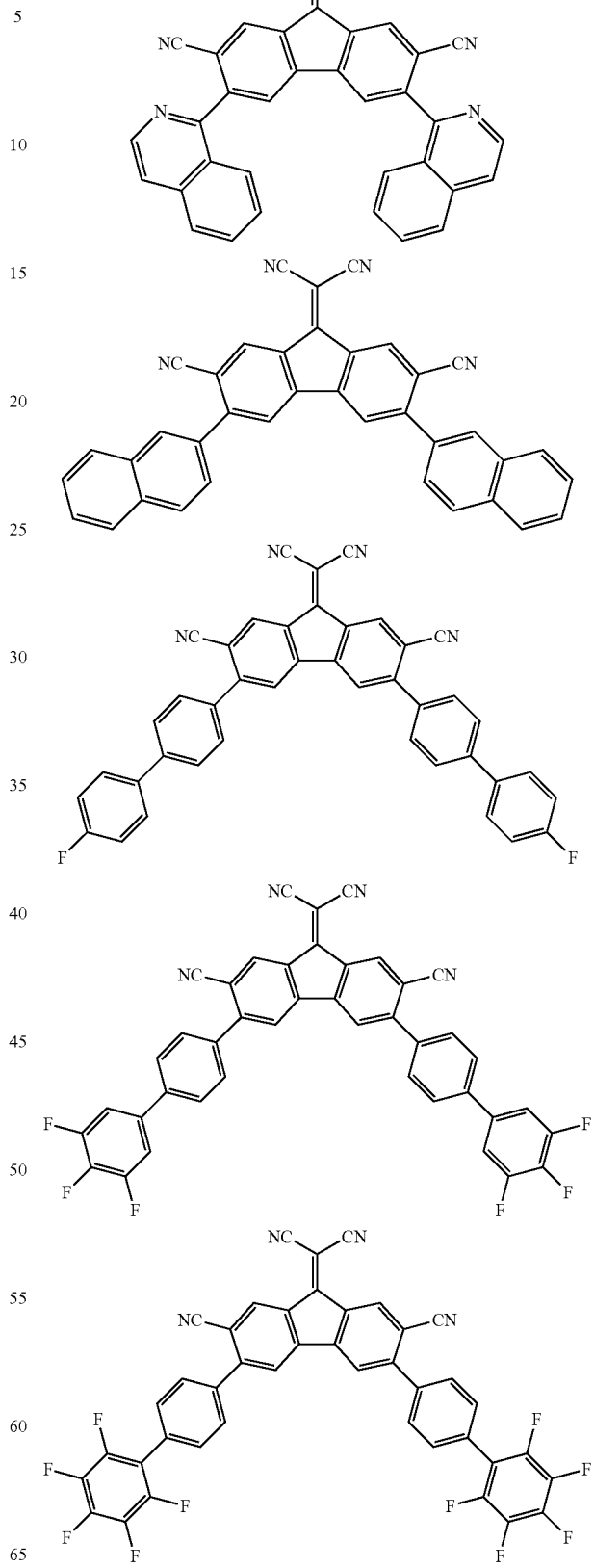

127
-continued
128
-continued
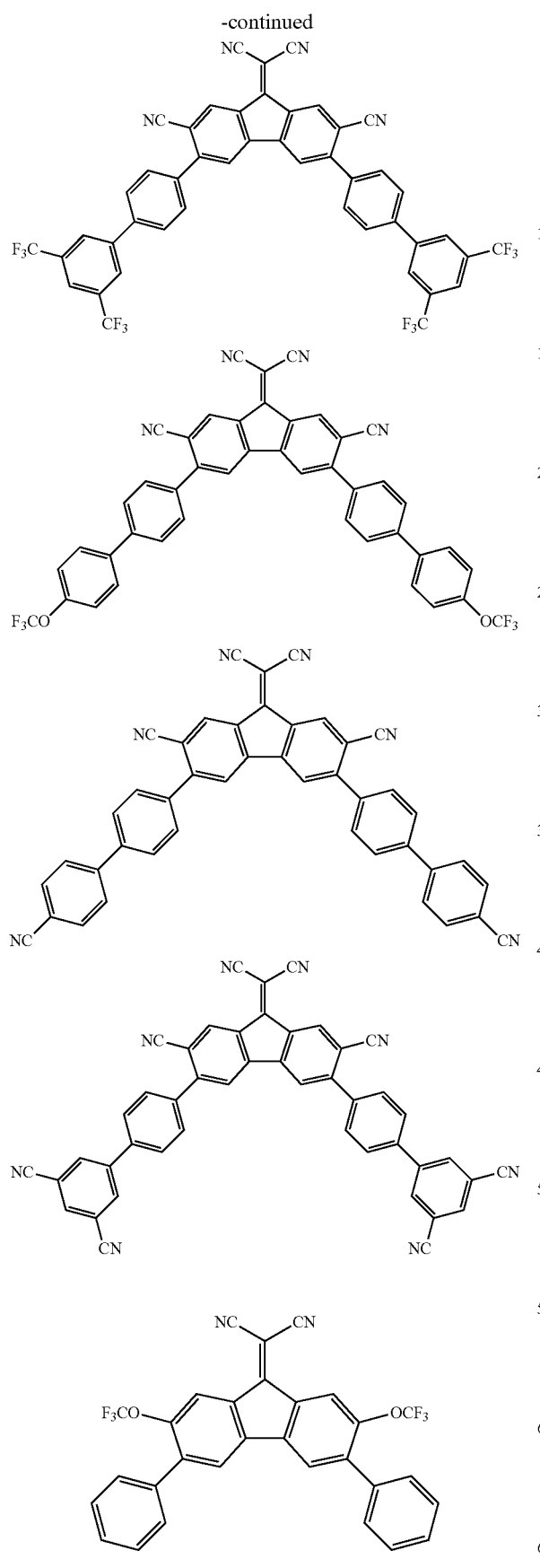
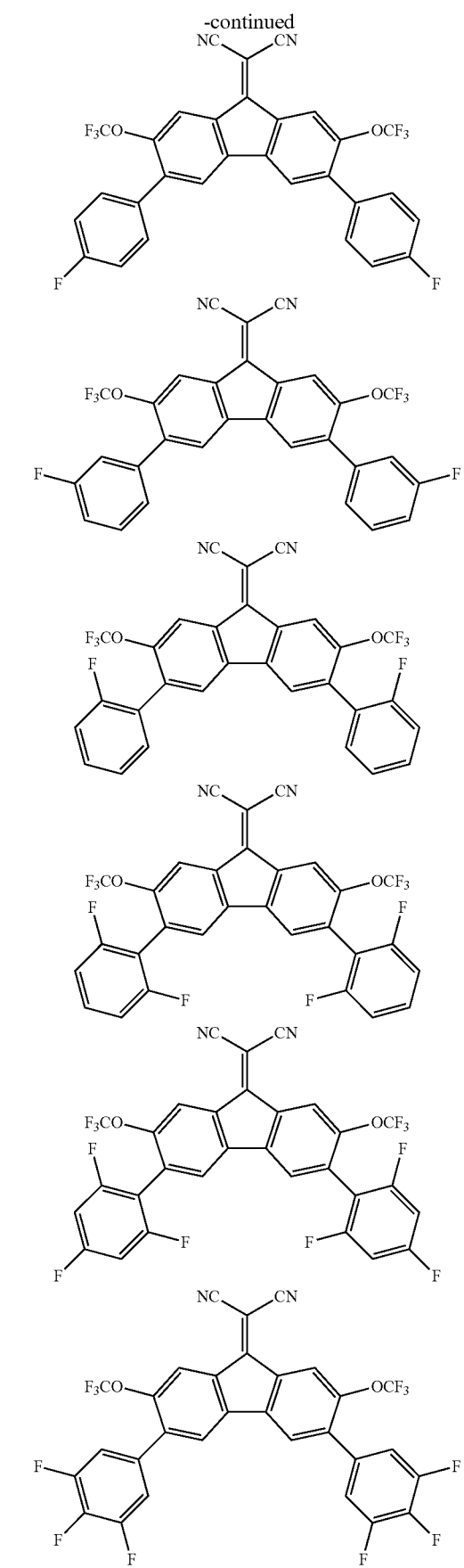

129
-continued
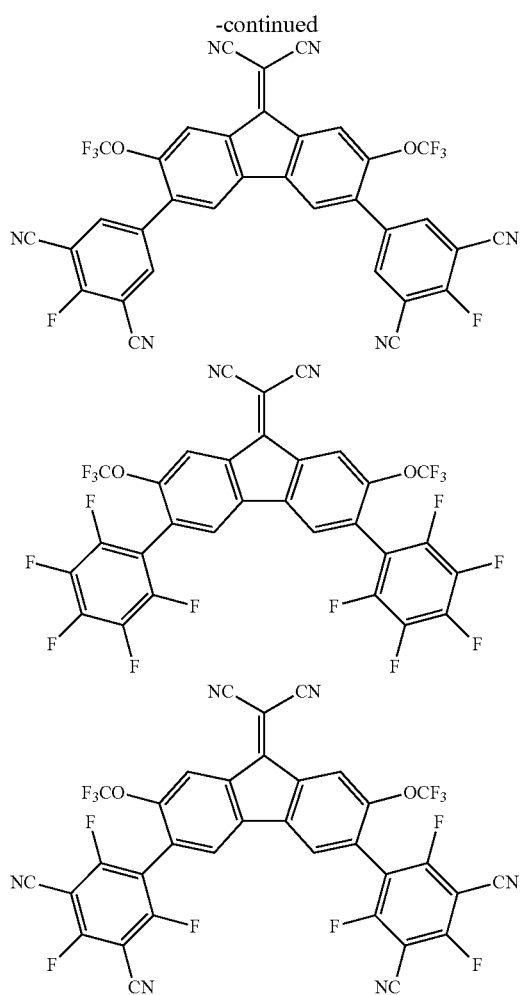
130
-continued
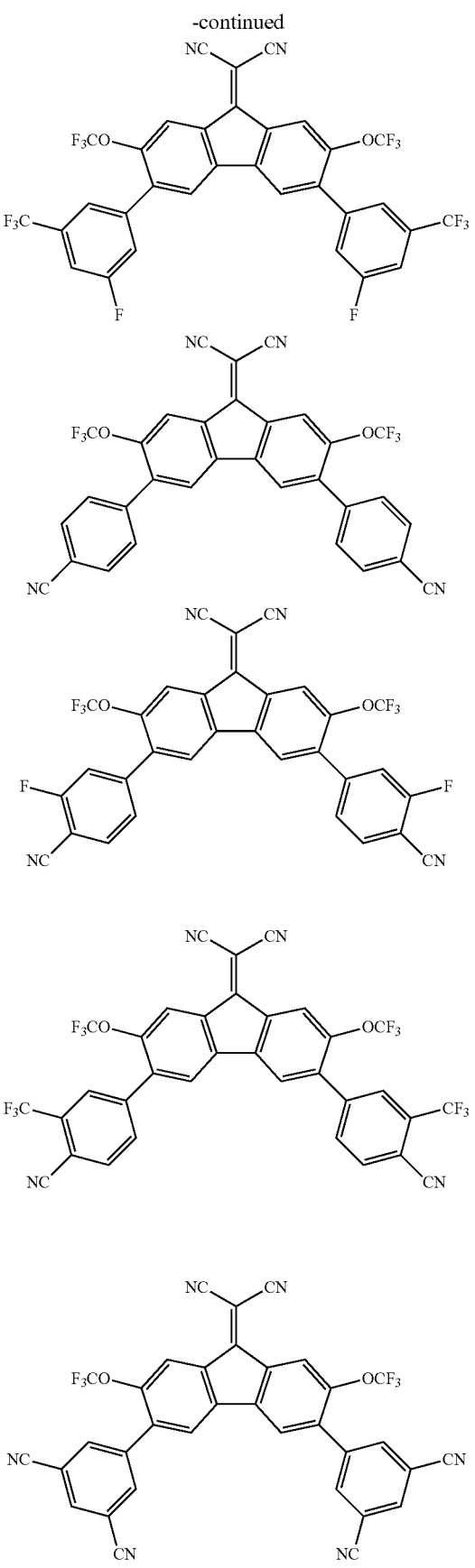

131
-continued
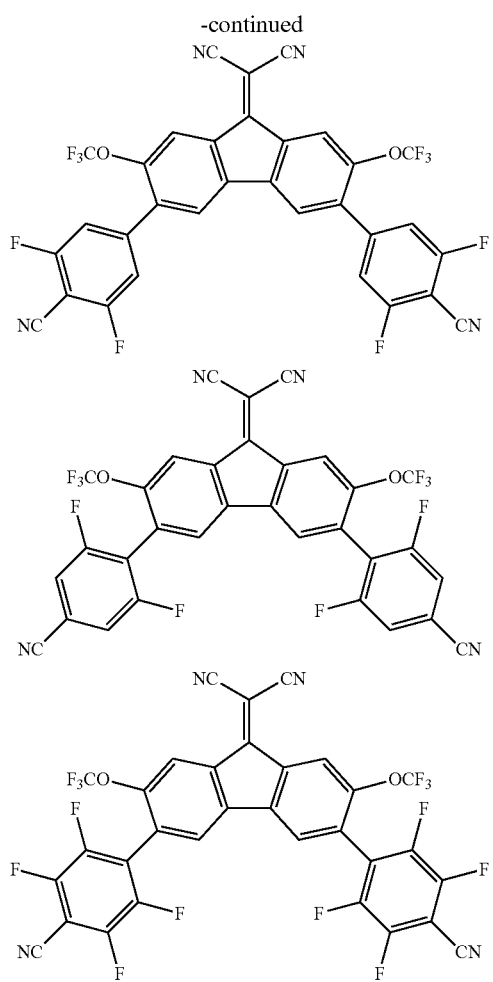
132
-continued
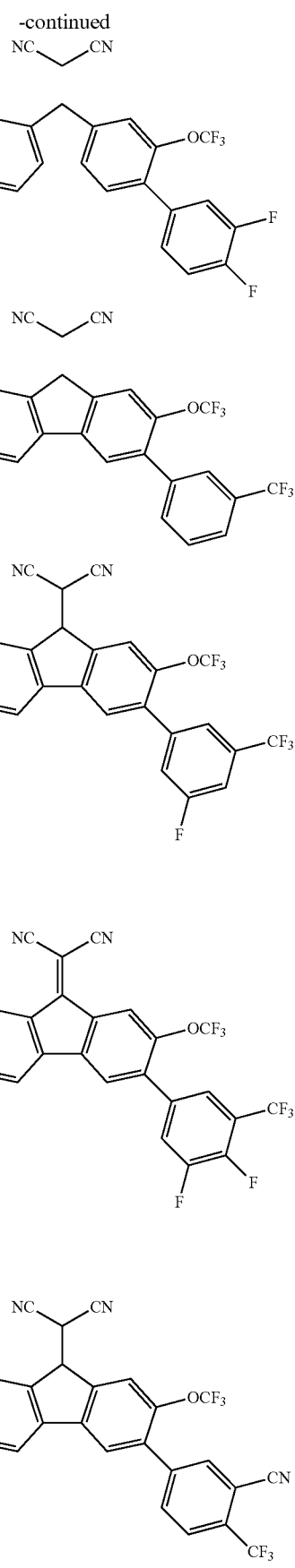
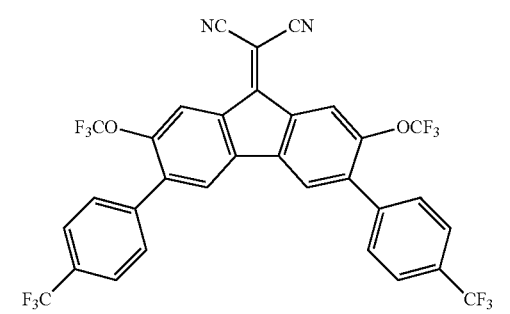
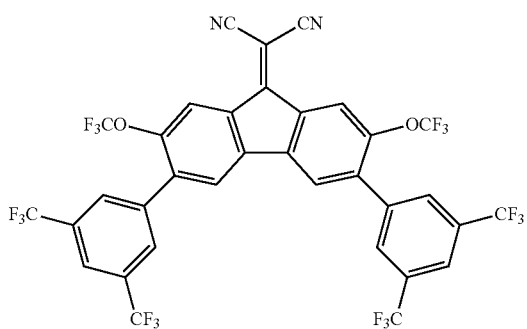

133
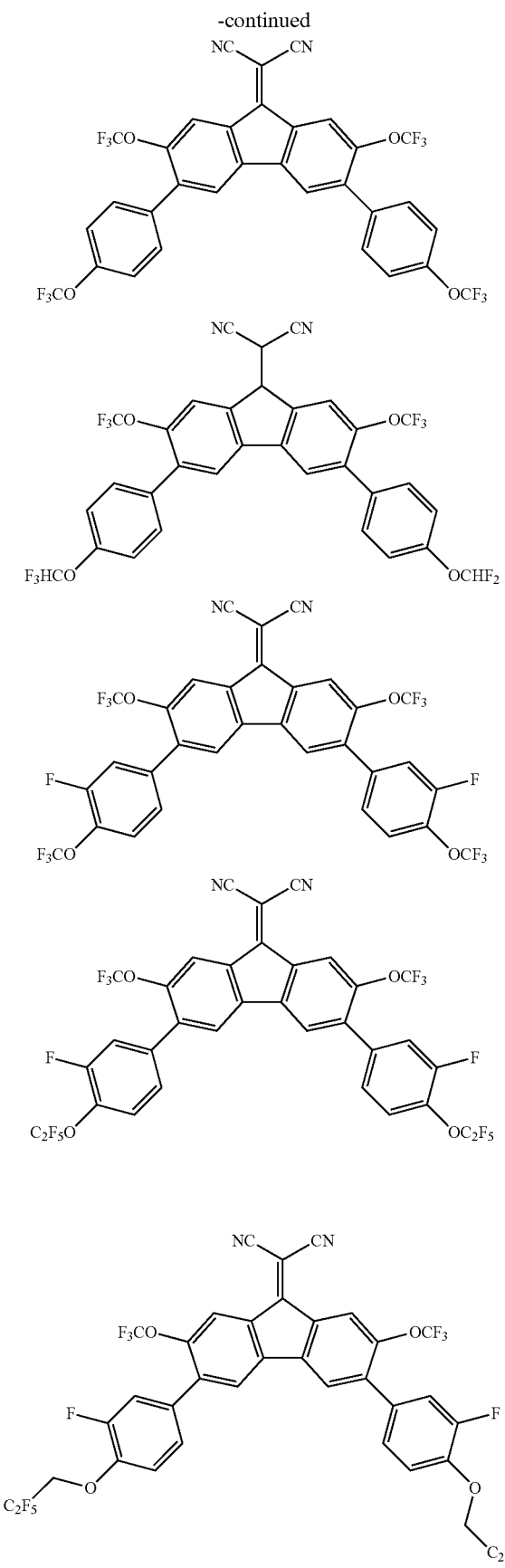
134
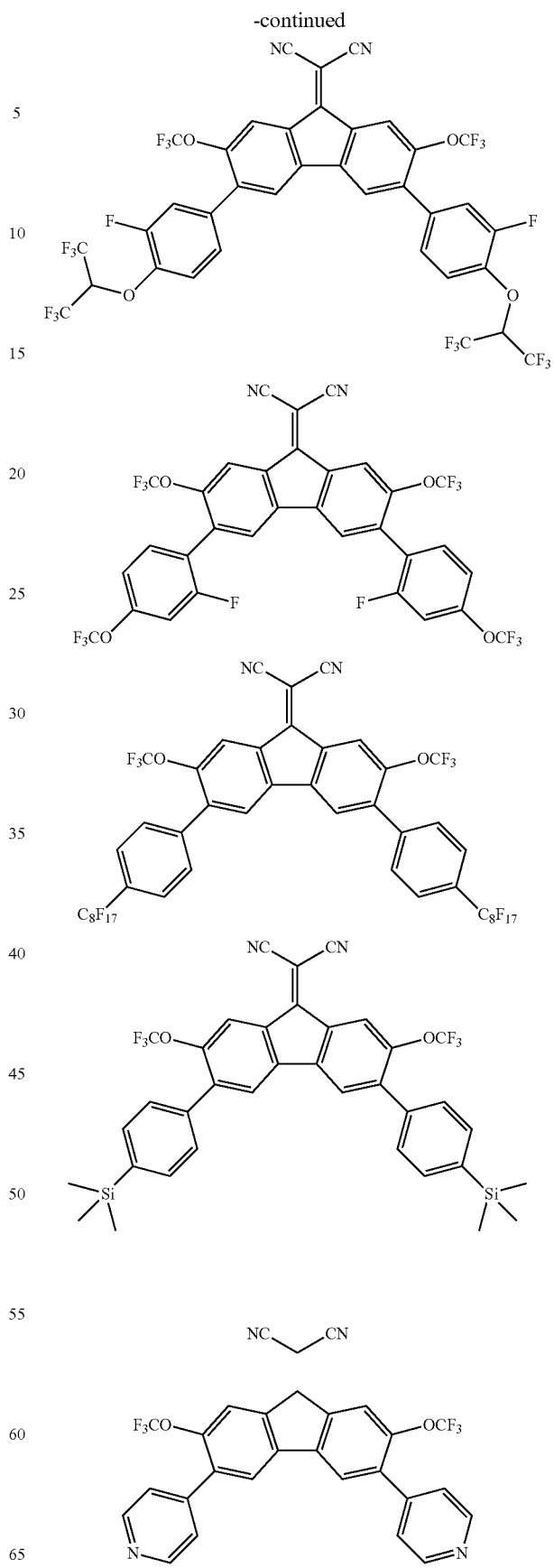

135
-continued
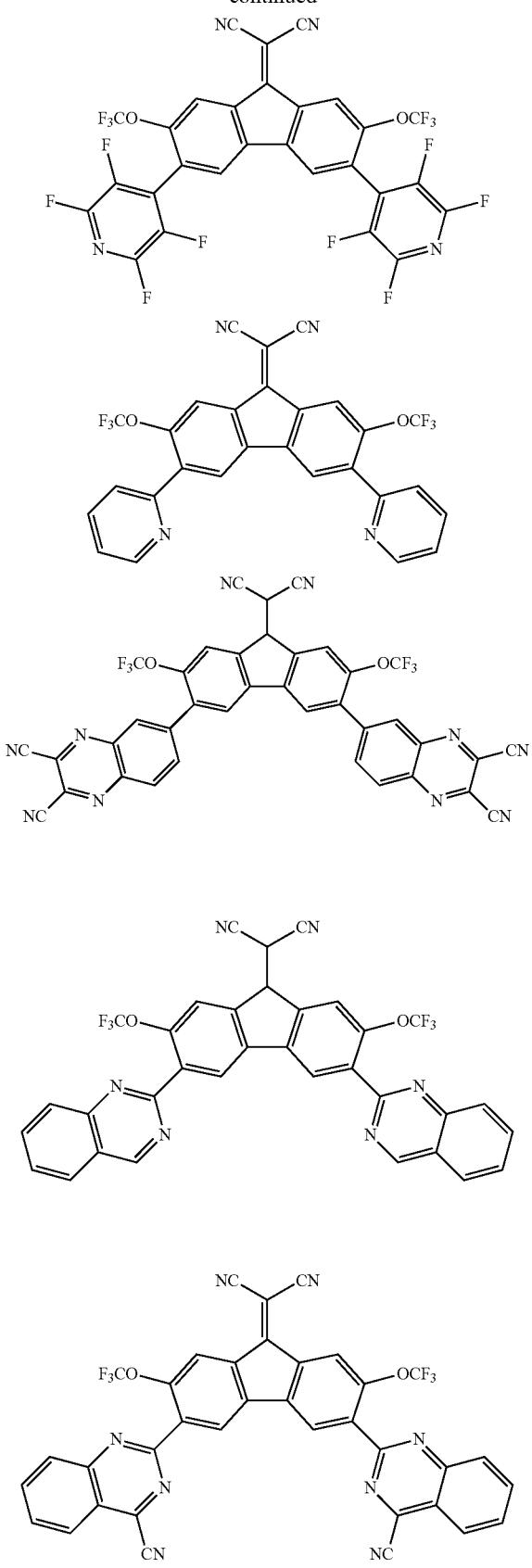
136
-continued
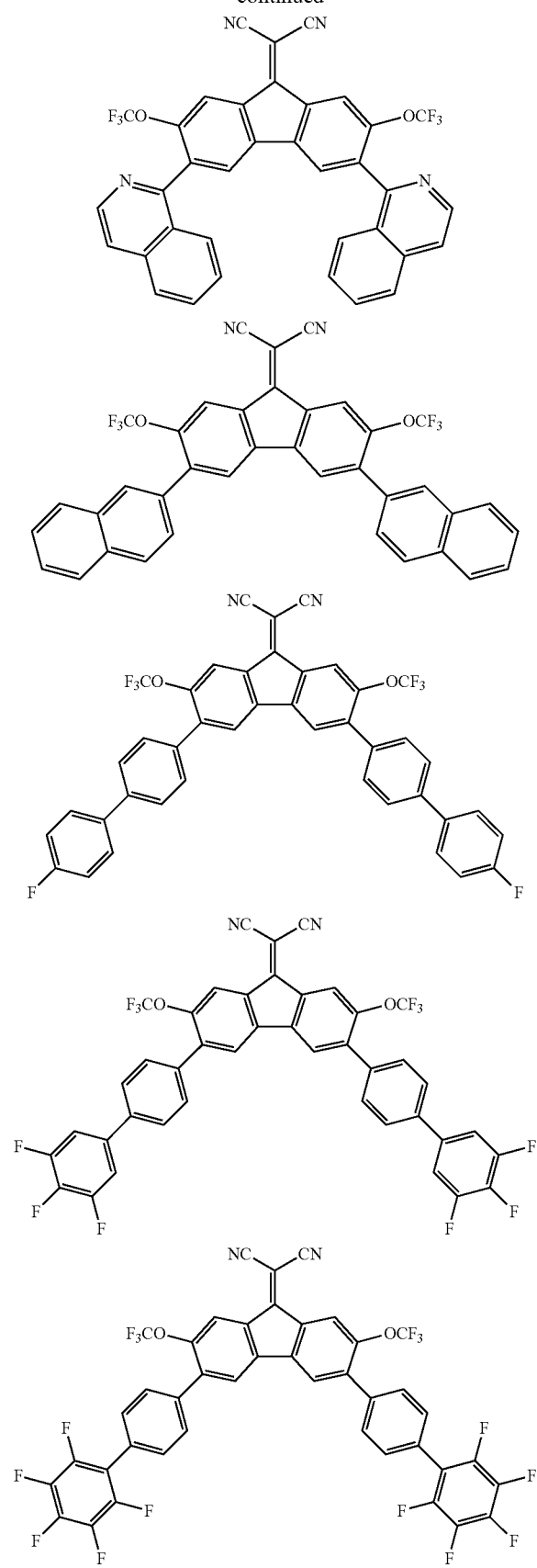

137
-continued
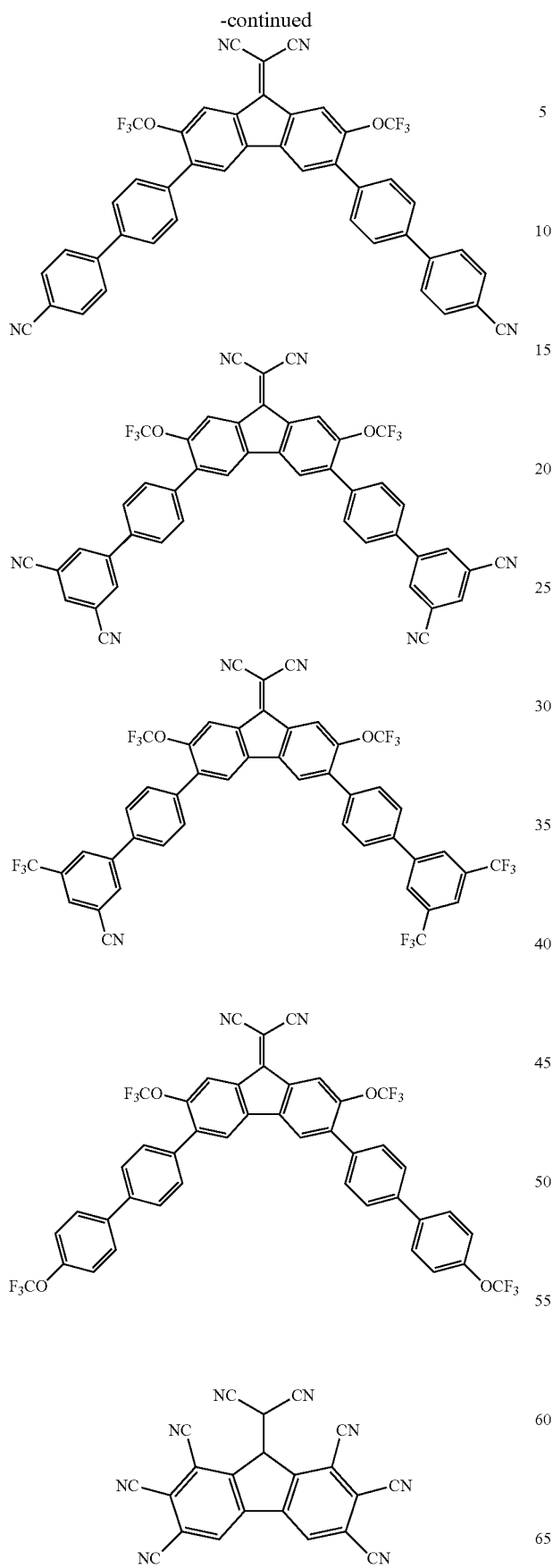
138
-continued
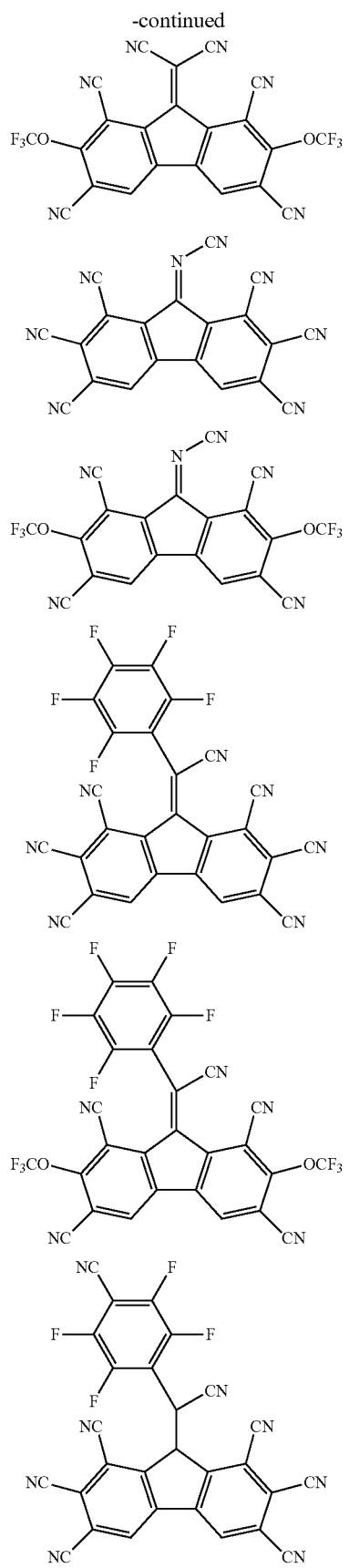

139
-continued
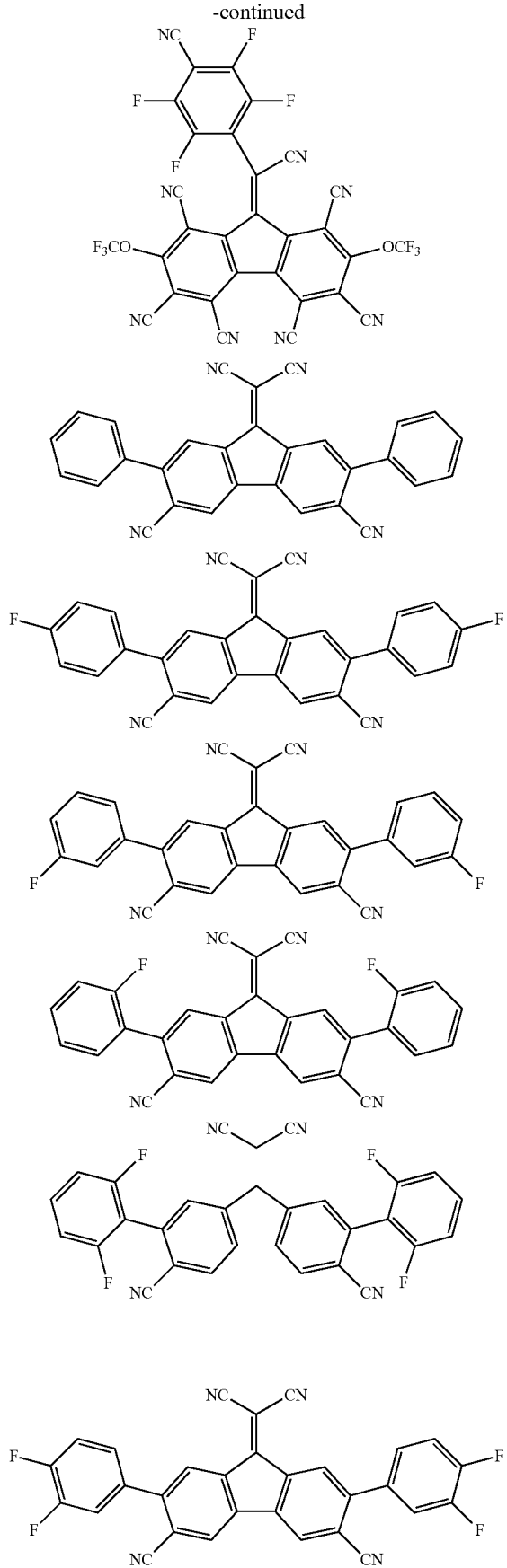
140
-continued
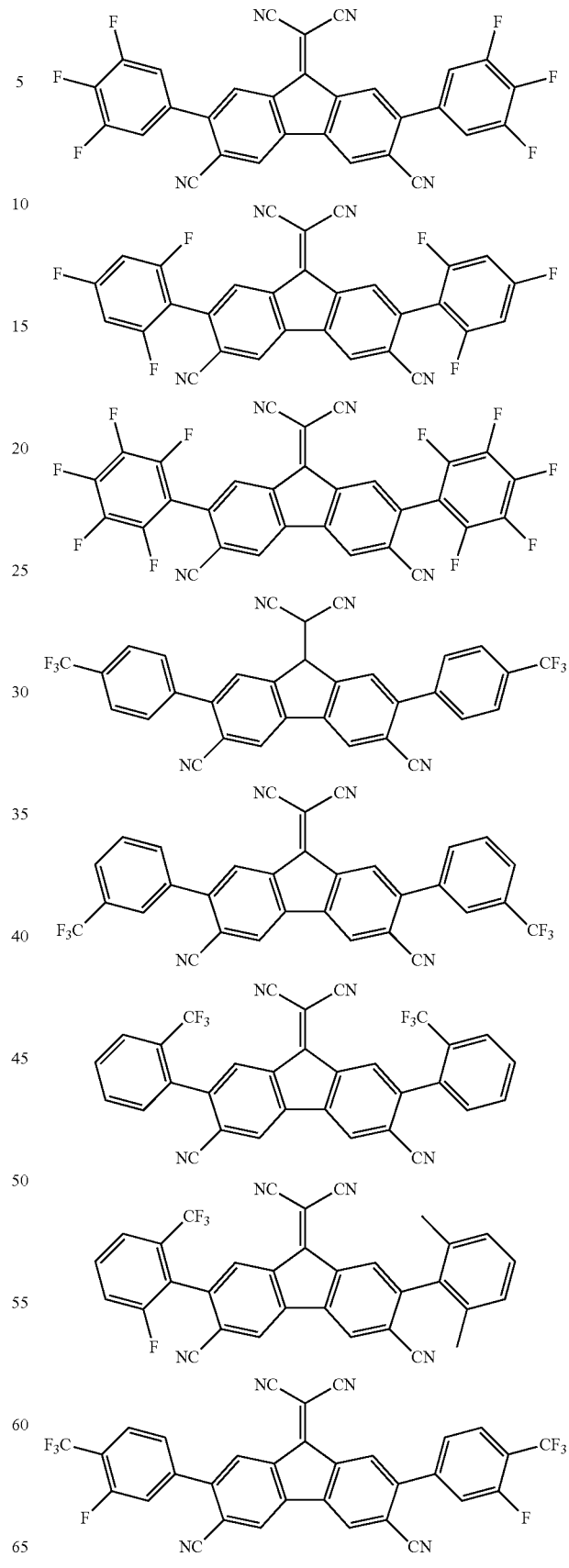

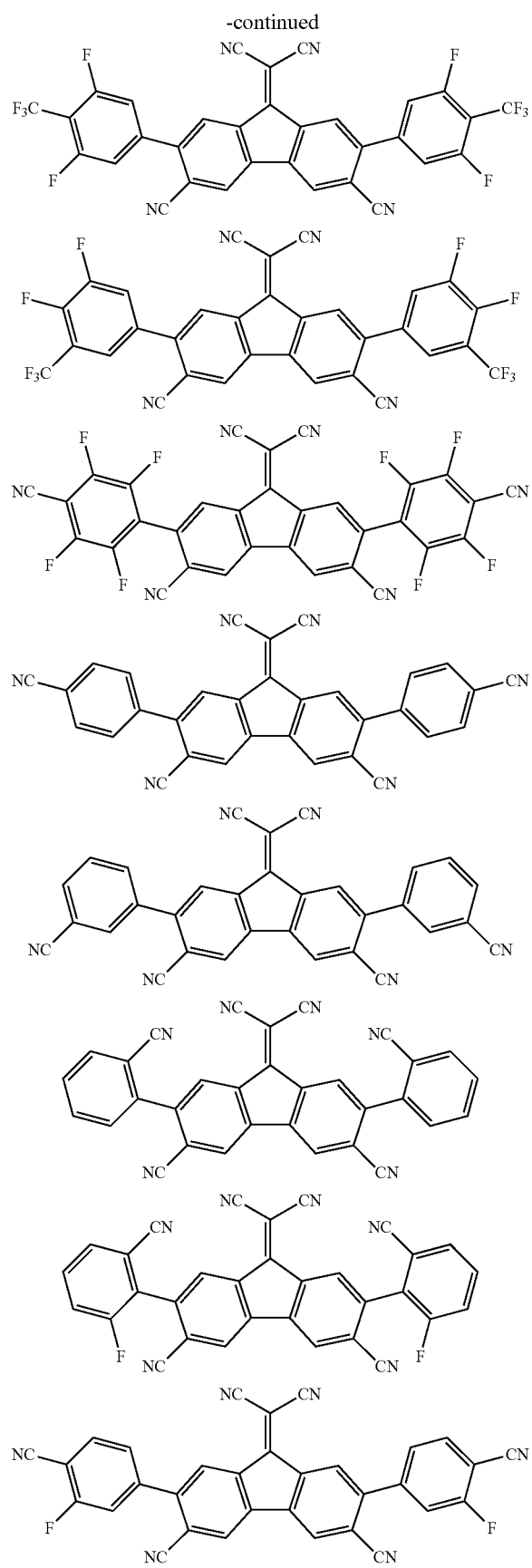
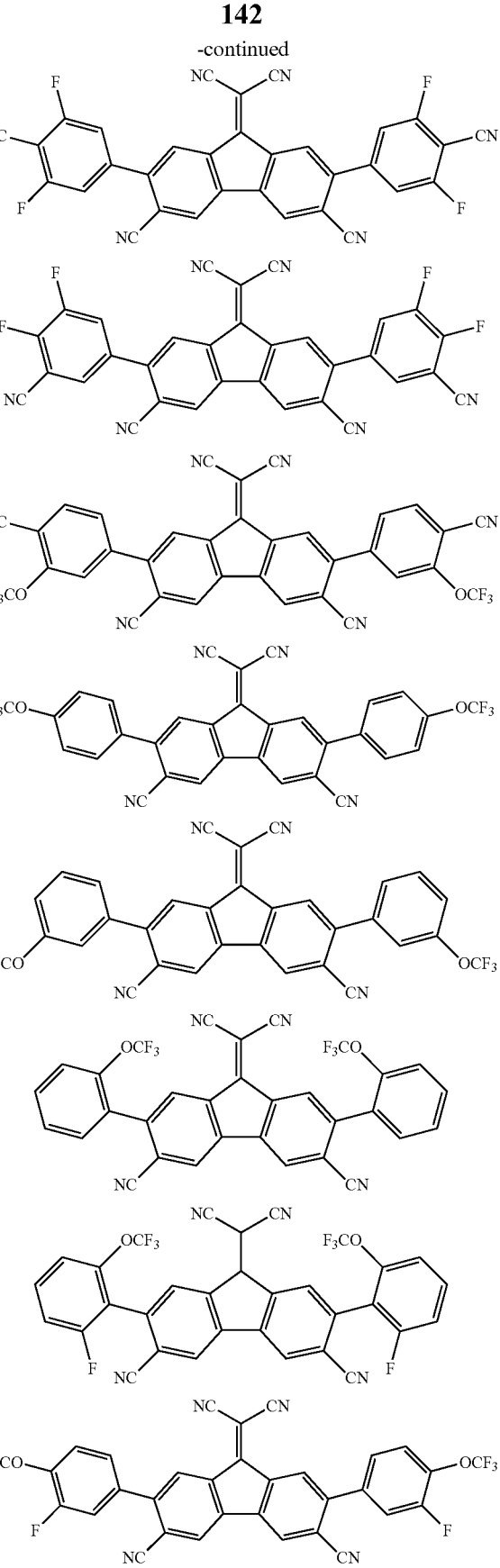

-continued
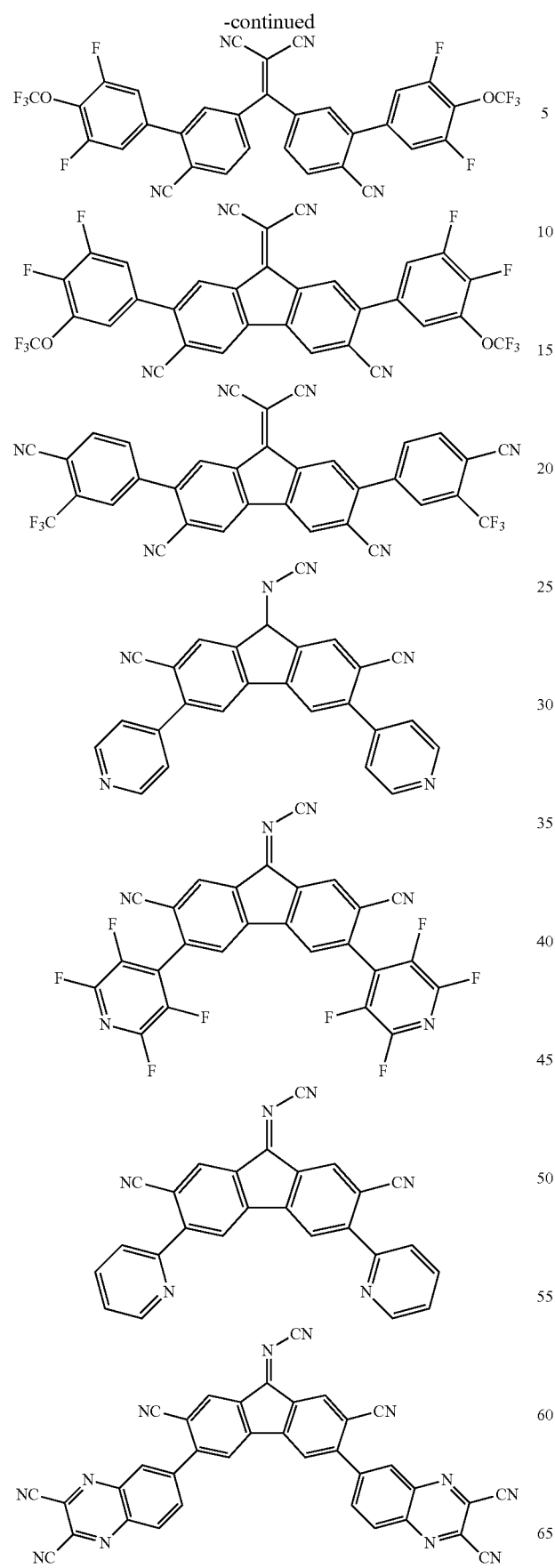
-continued
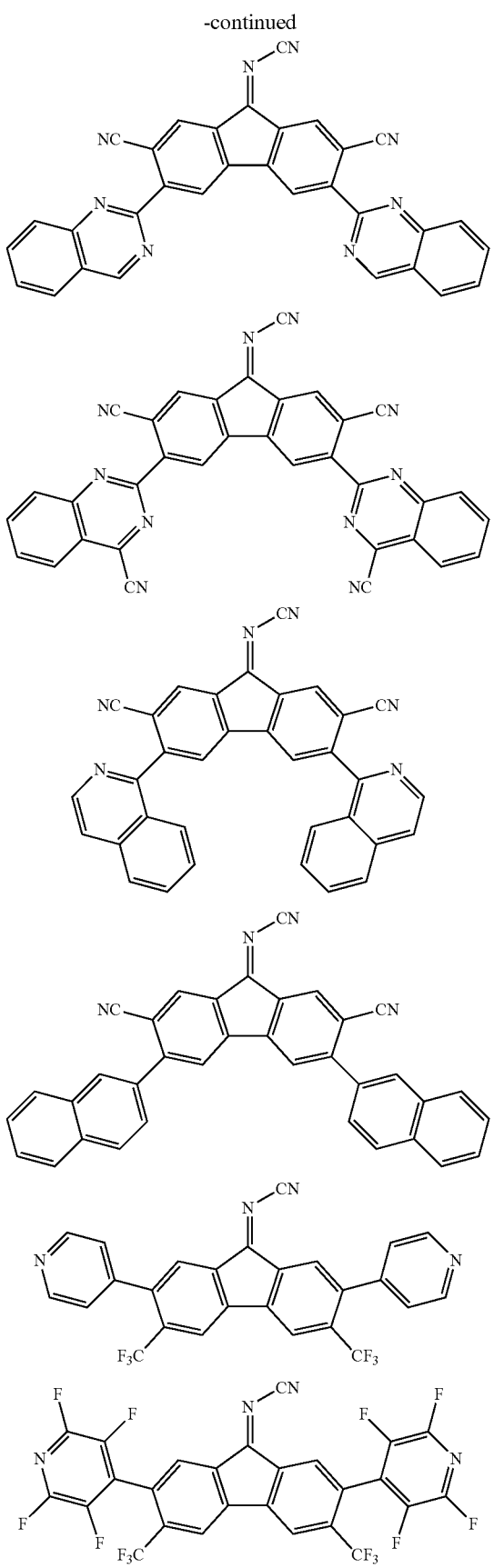

145
-continued
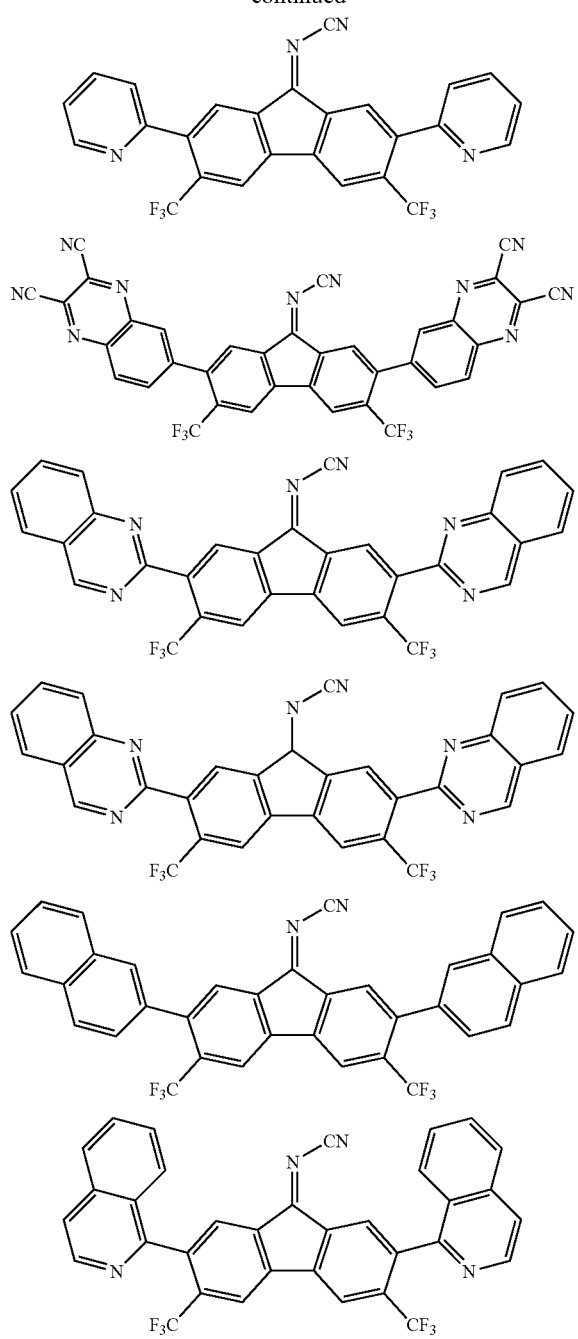
146
-continued
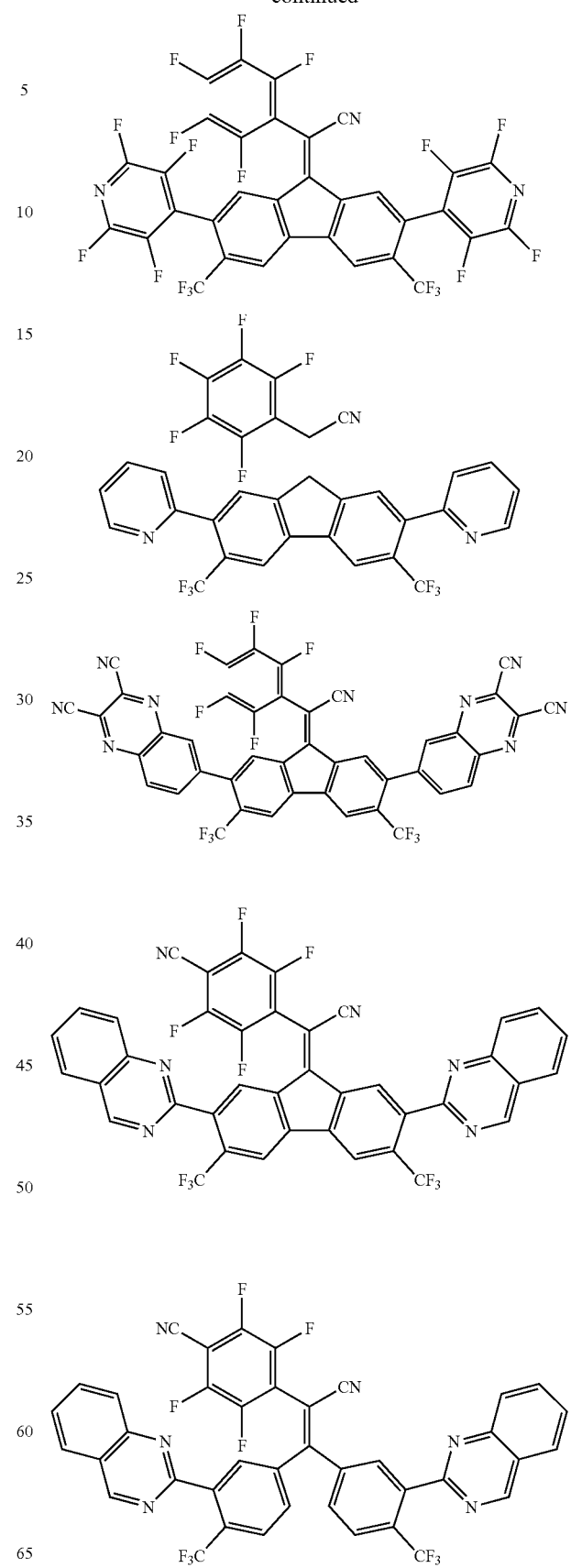

-continued

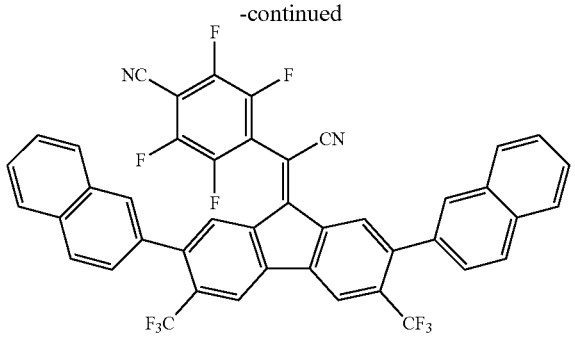

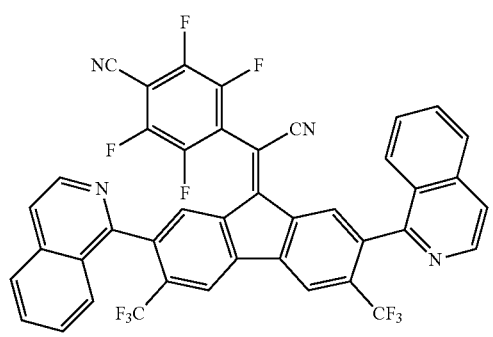

4. The organic electronic device of claim 1, wherein the one or more organic material layers comprise a hole injection layer, and the hole injection layer is formed of the compound alone or formed of the compound subjected to doping.

5. The organic electronic device of claim 1, wherein the one or more organic material layers comprise a doped hole transport layer, and the doped hole transport layer is formed of a hole transport material doped with the compound.

6. The organic electronic device of claim 1, wherein a first stack which emits light of a first color and a second stack which emits light of a second color are formed between the first electrode and the second electrode, and a charge generation layer which adjust charges so as to establish a charge balance is formed between the first stack and the second stack,
   the charge generation layer is composed of an N-type charge generation layer disposed adjacently to the first stack and a P-type charge generation layer disposed adjacently to the second stack, and
   the one or more organic material layers constitute the P-type charge generation layer, and the P-type charge generation layer is formed of the compound alone or formed of the compound subjected to doping.

7. The organic electronic device of claim 1, wherein a first stack which emits light of a first color and a second stack which emits light of a second color are formed between the first electrode and the second electrode, and a charge generation layer which adjust charges so as to establish a charge balance is formed between the first stack and the second stack,
   the charge generation layer is composed of an N-type charge generation layer disposed adjacently to the first stack and a P-type charge generation layer disposed adjacently to the second stack, and
   the one or more organic material layers constitute the P-type charge generation layer, and the P-type charge generation layer is formed of a hole transport material doped with the compound.

8. The organic electronic device of claim 1, further comprising:
   one or two or more layers selected from a group consisting of a light emitting layer, an electron transport layer, an electron injection layer, an electron blocking layer, and a hole blocking layer.

9. The organic electronic device of claim 1, wherein the organic electronic device is selected from a group consisting of an organic light emitting device, an organic solar cell, an organic photoconductor (OPC), and an organic transistor.

10. The organic electronic device of claim 1, wherein the one or more organic material layers comprise a light emitting layer, and the light emitting layer comprises a compound represented by the following Chemical Formula A-1:

[Chemical Formula A-1]

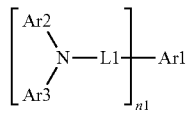

in Chemical Formula A-1, n1 is an integer of 1 or more,

Ar1 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L1 is a direct bond; a substituted or unsubstituted arylene group; or a substituted or unsubstituted heteroarylene group, Ar2 and Ar3 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or optionally combine with each other to form a substituted or unsubstituted ring, and when n1 is 2 or more, two or more structures in the parenthesis are the same as or different from each other.

11. The organic electronic device of claim 10, wherein L1 is a direct bond, Ar1 is a divalent pyrene group, Ar2 and Ar3 are the same as or different from each other, and are each independently an aryl group which is unsubstituted or substituted with a germanium group substituted with an alkyl group, and n1 is 2.

12. The organic electronic device of claim 1, wherein the one or more organic material layers comprise a light emitting layer, and the light emitting layer comprises a compound represented by the following Chemical Formula A-2:

[Chemical Formula A-2]

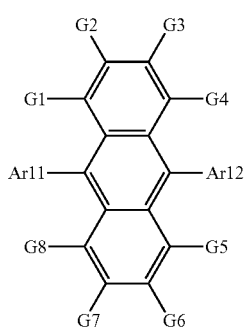

in Chemical Formula A-2,
Ar11 and Ar12 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted alkyl group; a substituted or unsubstituted monocyclic aryl group; or a substituted or unsubstituted polycyclic aryl group.

13. The organic electronic device of claim 12, wherein Ar11 and Ar12 are the same as or different from each other, and are each independently a phenyl group substituted with a 2-naphthyl group; a 1-naphthyl group; or a 2-naphthyl group, and G1 to G8 are all hydrogen, or at least one of G1 to G8 is an alkyl group, and the others are hydrogen.

14. The organic electronic device of claim 10, wherein the light emitting layer further comprises a compound represented by the following Chemical Formula A-2:

[Chemical Formula A-2]

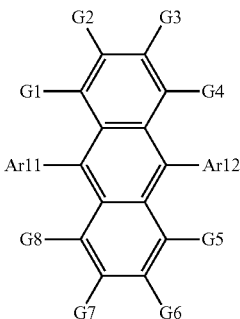

in Chemical Formula A-2,
Ar11 and Ar12 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted alkyl group; a substituted or unsubstituted monocyclic aryl group; or a substituted or unsubstituted polycyclic aryl group.

* * * * *